United States Patent
Higuchi et al.

(10) Patent No.: US 11,667,628 B2
(45) Date of Patent: *Jun. 6, 2023

(54) COMPOUNDS FOR IMAGING TAU PROTEINS THAT ACCUMULATE IN BRAIN

(71) Applicant: National Institutes for Quantum and Radiological Science and Technology, Chiba (JP)

(72) Inventors: Makoto Higuchi, Chiba (JP); Tetsuya Suhara, Chiba (JP); Masahiro Maruyama, Chiba (JP); Meiei Cho, Chiba (JP); Hitoshi Shimada, Chiba (JP)

(73) Assignee: NATIONAL INSTITUTES FOR QUANTUM AND RADIOLOGICAL SCIENCE AND TECHNOLOGY, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/477,479

(22) Filed: Sep. 16, 2021

(65) Prior Publication Data

US 2022/0056020 A1 Feb. 24, 2022

Related U.S. Application Data

(63) Continuation of application No. 16/798,226, filed on Feb. 21, 2020, now abandoned, which is a
(Continued)

(51) Int. Cl.
*C07D 417/06* (2006.01)
*C07F 7/18* (2006.01)
(Continued)

(52) U.S. Cl.
CPC ........ *C07D 417/06* (2013.01); *A61K 49/0017* (2013.01); *A61K 49/0021* (2013.01);
(Continued)

(58) Field of Classification Search
CPC .. C07D 417/06; C07D 277/64; C07D 401/06; C07D 405/06; C07D 405/14; C07D 417/14; A61K 49/0021
(Continued)

(56) References Cited

U.S. PATENT DOCUMENTS 3,833,863 A 9/1974 Wedster et al.
5,130,228 A 7/1992 Wade et al.
(Continued)

FOREIGN PATENT DOCUMENTS

AU 2017204357 B2 8/2017
CN 1791592 A 6/2006
(Continued)

OTHER PUBLICATIONS

Braak, Heiko, et al., "Staging of Alzheimer disease-associated neurofibrillary pathology using paraffin sections and immunocytochemistry," Acta Neuropathol (2006), vol. 112, pp. 389-404.
(Continued)

*Primary Examiner* — Michael G. Hartley
*Assistant Examiner* — Sean R Donohue
(74) *Attorney, Agent, or Firm* — Foley & Lardner LLP

(57) ABSTRACT

The present invention provides a compound represented by the following formula (I), a pharmaceutically acceptable salt thereof, or a solvate thereof:

[Formula 1]

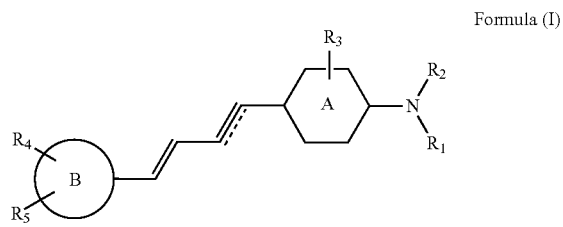

Formula (I)

wherein:
$R_1$ and $R_2$ are each separately selected from the group consisting of hydrogen, alkyl, alkenyl, acyl, and hydroxyalkyl;
$R_3$ is hydrogen or halogen;
ring A is a benzene ring or a pyridine ring;
ring B is selected from the group consisting of the following formulas (i), (ii), (iii), and (iv):

[Formula 2]

(Continued)

in the formula (ii), $R_a$ is alkyl;

$R_4$ and $R_5$ are each separately selected from the group consisting of hydrogen, hydroxy, alkoxy, haloalkoxy, halohydroxyalkoxy, and aminoalkyl; and

[Formula 3]

$$\equiv\equiv\equiv$$

represents a double bond or a triple bond. The above compound can be used as a molecular probe for imaging tau proteins that accumulate in the brain.

26 Claims, 8 Drawing Sheets

Related U.S. Application Data continuation of application No. 14/346,914, filed as application No. PCT/JP2012/083286 on Dec. 21, 2012, now Pat. No. 10,604,516.

(51) Int. Cl.

| | |
|---|---|
| *C07D 401/06* | (2006.01) |
| *C07D 405/06* | (2006.01) |
| *C07D 417/14* | (2006.01) |
| *C07D 277/64* | (2006.01) |
| *A61K 49/00* | (2006.01) |
| *C07D 401/14* | (2006.01) |
| *C07D 405/14* | (2006.01) |

(52) U.S. Cl.

CPC ......... *C07D 277/64* (2013.01); *C07D 401/06* (2013.01); *C07D 401/14* (2013.01); *C07D 405/06* (2013.01); *C07D 405/14* (2013.01); *C07D 417/14* (2013.01); *C07F 7/1804* (2013.01)

(58) Field of Classification Search

USPC .......................................................... 424/9.6

See application file for complete search history.

(56) References Cited

U.S. PATENT DOCUMENTS

| | | | |
|---|---|---|---|
| 5,264,329 | A | 11/1993 | Wade et al. |
| 7,060,697 | B2 | 6/2006 | Marsilje et al. |
| 7,910,579 | B2 | 3/2011 | Kudo et al. |
| 9,750,816 | B2 | 9/2017 | Bradner et al. |
| 9,770,512 | B2 | 9/2017 | Bradner et al. |
| 9,808,542 | B2 | 11/2017 | Walji et al. |
| 9,821,068 | B2 | 11/2017 | Bradner et al. |
| 10,125,114 | B2 | 11/2018 | Bradner et al. |
| 10,308,871 | B2 | 6/2019 | Yano |
| 10,464,925 | B2 | 11/2019 | Bradner et al. |
| 10,604,516 | B2 | 3/2020 | Higuchi et al. |
| 10,669,253 | B2 | 6/2020 | Bradner et al. |
| 10,730,870 | B2 | 8/2020 | Crew et al. |
| 10,772,962 | B2 | 9/2020 | Qian et al. |
| 10,849,980 | B2 | 12/2020 | Bradner et al. |
| 2006/0018825 | A1 | 1/2006 | Kudo et al. |
| 2009/0028787 | A1 | 1/2009 | Gravenfors et al. |
| 2009/0257949 | A1 | 10/2009 | Hefti et al. |
| 2010/0239496 | A1* | 9/2010 | Gangadharmath ..... A61P 25/28 424/1.65 |
| 2011/0130305 | A1 | 6/2011 | Patton et al. |
| 2012/0214994 | A1* | 8/2012 | Chi ..................... C07D 471/04 546/281.1 |
| 2014/0147428 | A1* | 5/2014 | Shchepinov ........... A61K 45/06 424/94.1 |
| 2015/0197498 | A1 | 7/2015 | Song et al. |
| 2017/0189566 | A1 | 7/2017 | Tu et al. |
| 2017/0233655 | A1 | 8/2017 | Saito |
| 2017/0362507 | A1 | 12/2017 | Okabe |
| 2018/0125821 | A1 | 5/2018 | Crew et al. |
| 2020/0085793 | A1 | 3/2020 | Crew et al. |

FOREIGN PATENT DOCUMENTS

| | | |
|---|---|---|
| CN | 1867552 A | 11/2006 |
| CN | 102639135 A | 8/2012 |
| CN | 107207459 A | 9/2017 |
| EP | 1 655 287 A1 | 5/2006 |
| EP | 2 397 139 A1 | 12/2011 |
| JP | S48-74796 A | 10/1973 |
| JP | S55-53333 A | 4/1980 |
| JP | S61-275836 A | 12/1986 |
| JP | H03-144569 A | 6/1991 |
| JP | 2007-106755 A | 4/2007 |
| JP | 2009-519239 A | 5/2009 |
| JP | 2011-512354 A | 4/2011 |
| JP | 2011-516866 A | 5/2011 |
| JP | 2012-102106 A | 5/2012 |
| TW | 201722957 A | 7/2017 |
| TW | 201722958 A | 7/2017 |
| WO | WO-2005/016888 A1 | 2/2005 |
| WO | WO-2007/034282 A2 | 3/2007 |
| WO | WO-2008/078424 A1 | 7/2008 |
| WO | WO-2010/011964 A2 | 1/2010 |
| WO | WO-2010/024769 A1 | 3/2010 |
| WO | WO-2010/087315 A1 | 8/2010 |
| WO | WO-2011/045415 A2 | 4/2011 |
| WO | WO-2011/065980 A2 | 6/2011 |
| WO | WO-2011/119565 A1 | 9/2011 |
| WO | WO-2015/188368 | 12/2015 |
| WO | WO-2016/105518 A1 | 6/2016 |
| WO | WO-2016/149668 A1 | 9/2016 |
| WO | WO-2017/007612 A1 | 1/2017 |
| WO | WO-2017/030814 A1 | 2/2017 |
| WO | WO-2018/011073 A1 | 1/2018 |
| WO | WO-2018/017370 A1 | 1/2018 |
| WO | WO-2018/102067 A2 | 6/2018 |
| WO | WO-2018/119448 A1 | 6/2018 |
| WO | WO-2019/014429 A1 | 1/2019 |
| WO | WO-2019/214681 A1 | 11/2019 |
| WO | WO-2020/006264 A1 | 1/2020 |
| WO | WO-2020/041331 A1 | 2/2020 |
| WO | WO-2021/011913 A1 | 1/2021 |

OTHER PUBLICATIONS

Braak, Heiko, et al., "Staging of Alzheimer's Disease-Related Neurofibrillary Changes," Neurobiology of Aging, vol. 16, No. 3, (1995), pp. 271-284.

Braymer, Joseph J., et al., "Recent Development of Bifunctional Small Molecules to Study Metal-Amyloid-B Species in Alzheimer's Disease," International Journal of Alzheimer's Disease, vol. 2011, Article ID 623051, (2011), doi: 10.4061/2011/623051, 9 pages.

Cary, Brian P., et al., "Targeting Metal-Aß Aggregates with Bifunctional Radioligand [11 C]L2-b and a Flourine-18 Analogue [18 F]FL2-b," ACS Medicinal Chemistry Letters, vol. 6, Nov. 9, 2014, pp. 112-116.

DeVos, Sarah L., et al., "Synaptic Tau Seeding Precedes Tau Pathology in Human Alzheimer's Disease Brain," Frontiers in Neuroscience, Apr. 2018, vol. 12, Article 267, 15 pages.

Final Office Action on U.S. Appl. No. 17/320,882 dated Dec. 20, 2021.

International Preliminary Report on Patentability dated Sep. 18, 2020 issued in International Application No. PCT/CN2019/086201, 72 pages.

International Search Report dated Aug. 12, 2019 issued in International Application No. PCT/CN2019/0826201, 7 pages.

International Search Report dated Feb. 9, 2021 issued in International Application No. PCT/US2020/060459, 3 pages.

International Search Report dated Jan. 29, 2021 issued in International Application No. PCT/IB2020/057415, 10 pages.

(56) References Cited

OTHER PUBLICATIONS

Kfoury, Najla, et al., "Trans-cellular Propagation of Tau Aggregation by Fibrillar Species," the Journal of Biological Chemistry, vol. 287, No. 23, (2012), pp. 19440-19451.
Klunk, William E., et al., Uncharged thioflavin-T derivatives bind to amyloid-beta protein with high affinity and readily enter the brain, Life Sciences, vol. 69, (2001), pp. 1471-1484.
Nakazono, Manabu, et al., "Novel styrylbenzene derivatives for detecting amyloid deposits," Clinica Chimica Acta, vol. 436, May 9, 2014, pp. 27-34.
Non-Final Office Action on U.S. Appl. No. 17/320,882 dated Oct. 7, 2021.
Non-Final Office Action on U.S. Appl. No. 17/320,913 dated Sep. 21, 2021.
Notice of Allowance on U.S. Appl. No. 14/346,914 dated Nov. 1, 2019.
Ono, Maiko, et al., "Distinct binding of PET ligands PBB3 and AV-1451 to tau fibril strains in neurodegenerative tauopathies," Brain, (2017), 140(3), pp. 764-780, doi:10.1093/brain/aww339.
Rudikoff, Stuart, et al., "Single amino acid substitution altering antigen-binding specificity," Proc. Natl. Acad. Sci. USA, vol. 79, (1982), pp. 1979-1983.
Sanders, David W., et al., "Distinct Tau Prion Strains Propagate in Cells and Mice and Define Different Tauopathies," Neuron, vol. 82, (2014), pp. 1271-1288.
SantaCruz, K., et al., "Tau Suppression in a Neurodegenerative Mouse Model Improves Memory Function," Science, (2005), 309(5733), pp. 476-481.
Silva, Catarina, et al., "Targeted degradation of aberrant tau in frontotemporal dementia patient-derived neuronal cell models," eLife, 2019, 8e45457, 31 pages.
Song, Lixin, et al., "Analysis of tau post-translational modifications in rTg4510 mice, a model of tau pathology," Molecular Neurodegeneration, (2015), 10:14, 11 pages.
Takuwa, Hiroyuki, et al., "Hemodynamic changes during neural deactivation in awake mice: a measurement by laser-Doppler flowmetry in crossed cerebellar diaschisis," Brain Research, (2013), vol. 1537, pp. 350-355, doi: 10.1016/j.brainres.2013.09.023.
Tomita, Yutaka, et al., "Long-term in vivo investigation of mouse cerebral microcirculation by fluorescence confocal microscopy in the area of focal ischemia," Journal of Cerebral Blood Flow & Metabolism, (2005), vol. 25, pp. 858-867, doi: 10.1038/sj.jcbfm. 9600077.
U.S. Notice of Allowance on U.S. Appl. No. 17/320,913 dated Nov. 29, 2021.
Wang et al., "A near infrared dye laser pumped by nitrogen laser light", Zhongguo Jiguang, 1989, vol. 16, No. 8, pp. 492-495.
Wilen, Samuel H., et al., "Strategies in Optical Resolutions," Tetrahedron Report No. 38, Tetrahedron, vol. 33, Pergamon Press, (1977), pp. 2725-2736.
Written Opinion of the International Searching Authority dated Aug. 12, 2019 issued in International Application No. PCT/CN2019/086201, 4 pages.
Written Opinion of the International Searching Authority dated Feb. 9, 2021 issued in International Application No. PCT/US2020/060459, 4 pages.
Allowance Decision from the Intellectual Property Office dated Dec. 9, 2021 issued in TW Application No. 109139798, with English translation, 4 pages.
Examination Report No. 2 for Standard patent application dated Sep. 27, 2021 issued in AU Patent Application No. 2019265346, 11 pages.
Feng, Xun, et al., "Aerobic Oxidation of Alcohols and the Synthesis of Benzoxazoles Catalyzed by a Cuprocupric Coordination Polymer ($Cu^+$-CP) Assisted by TEMPO," Inorganic Chemistry, 2015, vol. 54, Issue No. 5, pp. 2088-2090. (Author's copy).
International Search Report and Written Opinion of the International Searching Authority dated Feb. 9, 2022 issued in International Application No. PCT/IB2021/054167, 13 pages.
Perry, Robert, J., et al.,"Palladium-Catalyzed Syntheses of 2-Arylbenzothiazoles," Organometallics, 1994, vol. 13, pp. 3346-3350.
Rao, R Nishanth, et al., "Efficient access to imidazo[1,2-a]pyridines/pyrazines/pyrimidines via catalyst free annulation reaction under microwave irradiation in green solvent,"ACS Combinatorial Science, 2018, vol. 20, Issue No. 3, pp. 164-171 (Accepted Manuscript).
Santra, Sourav Kumar, et al., "Peroxide Free Pd(II)-Catalyzed ortho-Aroylation and ortho-Halogenation of Directing Arenes," J. Org. Chem., 2016, vol. 81, Issue No. 14, pp. 6066-6074. (Accepted manuscript).
Xie, Yuan-Yuan, et al., "Organic reactions in ionic liquids: cyclocondensation of α-bromoketones with 2-aminopyridine", J. Chem. Research (S), 2003, pp. 614-615. (Short Paper).
Aakeroy, C.B., et al., "Directed Supramolecular Assembly of Cu(II)-based "Paddlewheels" into Infinite 1-D Chains using Structurally Bifunctional Ligands", the Royal Society of Chemistry, Dalton Trans. 2006, pp. 1627-1635.
Arriagada, et al., "Neurofibrillary Tangles but not Senile Plaques Parallel Duration and Severity of Alzheimer's Disease," Neurology, 1992, vol. 42, pp. 631-639.
Ballatore, et al., "Tau-mediated Neurodegeneration in Alzheimer's Disease and related Disorders," Nature Reviews/Neuroscience, Sep. 2007, vol. 8, pp. 663-672.
Ehrenberg, et al. "Surface potential on purple membranes and its sidedness studied by a resonance Raman dye probe", Biophysical Journal, 1984, vol. 45, No. 4, pp. 663-670.
Etaiw, et al., "Photophysics of benzazole derived push-pull butadienes: a highly sensitive fluorescence probes," Journal of Photochemistry and Photobiology, A: Chemistry, 2006, vol. 177, No. 2-3, pp. 238-247.
Final Office Action on U.S. Appl. No. 16/798,226 dated Feb. 16, 2021.
Final Office Action on U.S. Appl. No. 16/798,226 dated Sep. 7, 2021.
International Search Report for PCT/JP2012/083286, dated Mar. 5, 2013, 5 pgs.
Kung, H.F., et al., (Dec. 19, 2001), "Novel stillbenes as probes for amyloid plaques," J. Am Chem Soc 123(50): 12740-12741.
La Clair, James J., "Selective Detection of the Carbohydrate-Bound State of Concanavalin A at the Single Molecule Level", Journal of the American Chemical Society, 1997, vol. 119, No. 33, pp. 7676-7684.
Maruyama, et al., "Imaging of Tau Pathology in a Tauopathy Mouse Model and in Alzheimer Patients Compared to Normal Controls," Neutron Article, vol. 79, Sep. 18, 2013, pp. 1094-1108.
Matsumura, K., et al., (2011). "Phenyldiazenyl benzothiazole derivatives as probes for in vivo imaging of neurofibrilliary tangles in Alzheimer's disease brains," MedChemComm 2:596-600.
U.S. Office Action on U.S. Appl. No. 16/798,226 dated Oct. 26, 2020.
Xu, et al., "Tau protein, aprotein and Alzheimer's disease A protein and its role", Journal of Practice on Clinical Medicines, 2008, vol. 12, No. 3, pp. 118-120, Chinese language.
Yoshiyama, et al., Synapse Loss and Microglial Activation Precede Tangles in a P301S Tauopathy Mouse Model, Neuron, Feb. 1, 2007, vol. 53, pp. 337-351.
Zhuang, Z.P., et al., Radioiodinated Styrylbenzenes and Thioflavins as Probes for Amyloid Aggregates, J. Med. Chem. 2001, vol. 44, pp. 1905-1914.
Notice of grant for patent dated Jul. 30, 2019 issued in Australian Application No. 2017204357, 1 page.
International Report on Patentability dated May 17, 2022 issued in International Application No. PCT/US2020/060459 by the International Bureau of WIPO, 5 pages.
Non-Final Office Action on U.S. Appl. No. 17/477,411 dated Jun. 14, 2022.
Yang, Yanping, et al., "Radiolabeled bioactive benzoheterocycles for imaging β-amyloid plaques in Alzheimer's disease," European Journal of Medicinal Chemistry, vol. 87, 2014, pp. 703-721.
Final Office Action on U.S. Appl. No. 17/477,411 dated Sep. 30, 2022.

(56) References Cited

OTHER PUBLICATIONS

Non-Final Office Action on U.S. Appl. No. 17/320,882 dated Sep. 14, 2022.
Non-Final Office Action on U.S. Appl. No. 17/687,570 dated Nov. 7, 2022.
Notice of Allowance on U.S. Appl. No. 17/687,570 dated Dec. 7, 2022.

* cited by examiner

FIG. 1A
FIG. 1B
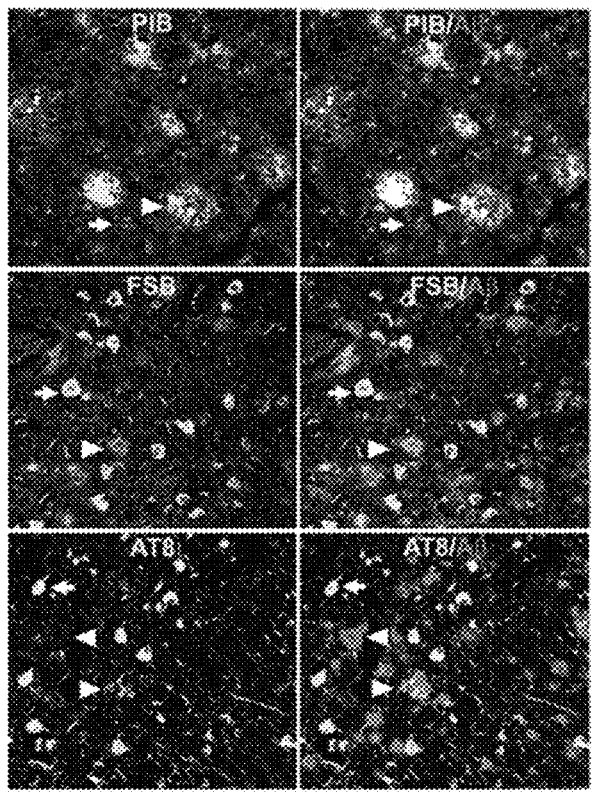
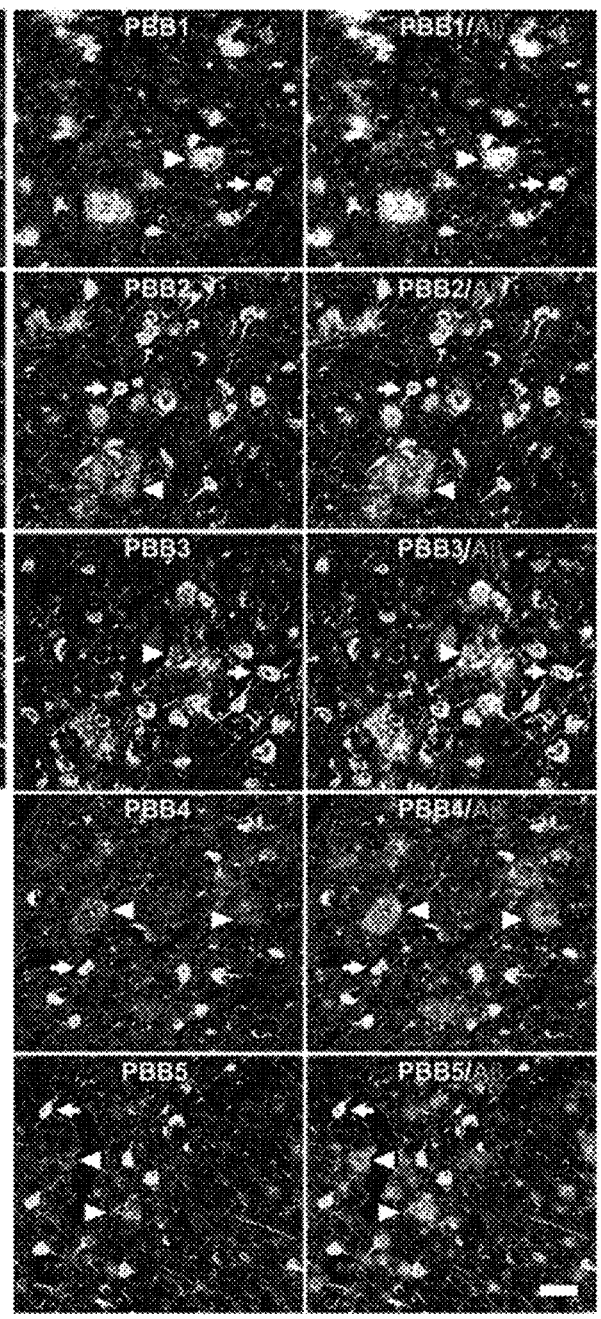

FIG. 3B

| NAME OF COMPOUND | AD NFTs | Tg | NAME OF COMPOUND | AD NFTs | Tg |
|---|---|---|---|---|---|
| mPBB5 | | | Core1-20 | | |
| PBB2.1 | | | Core2-9 | | |
| PBB2.2 | | | Core2-10 | | |
| PBB2.3 | | | Core2-14 | | |
| PBB3.1 | | | F0-PBB3 ANALOG | | |
| PBB3.2 | | | PBQ3.0 | | |
| Core1-4 | | | PBQ3 | | |
| Core1-5 | | | PBQ3.1 | | |
| Core1-11 | | | PBQ3.2 | | |
| Core1-15 | | | PBB3.2N | | |

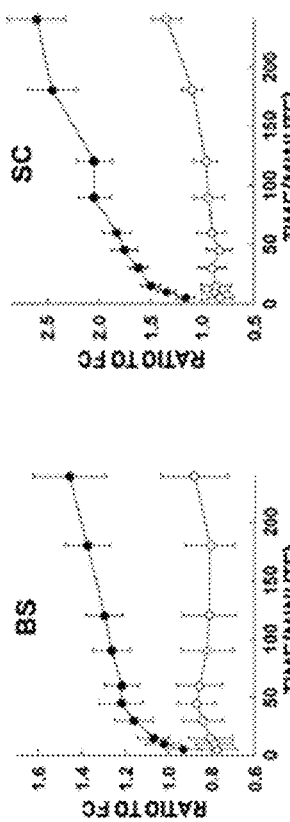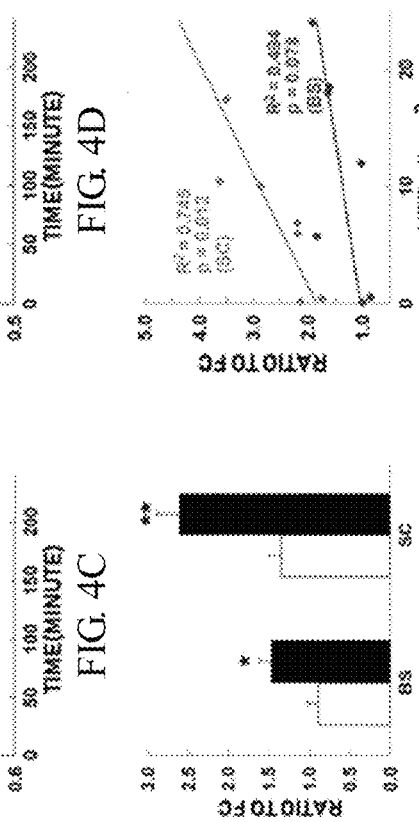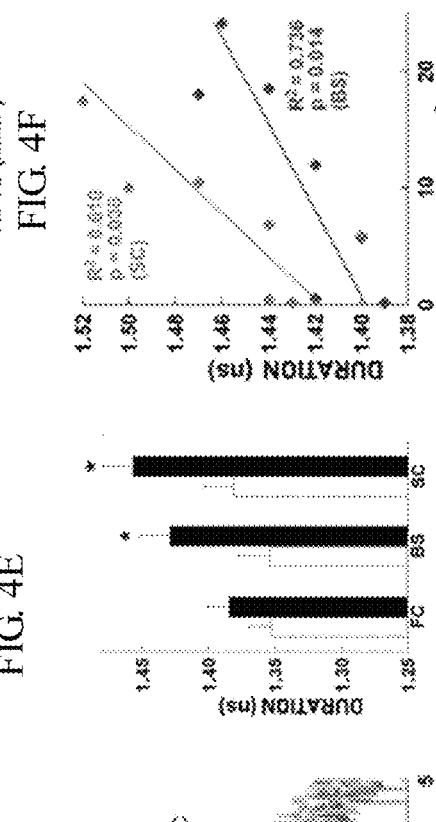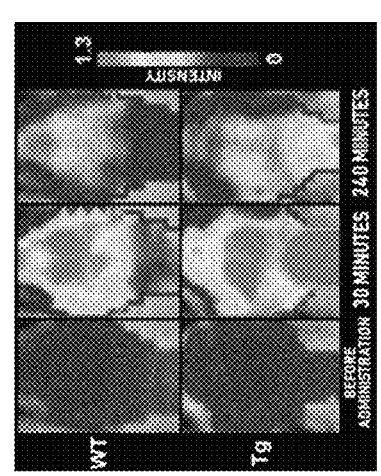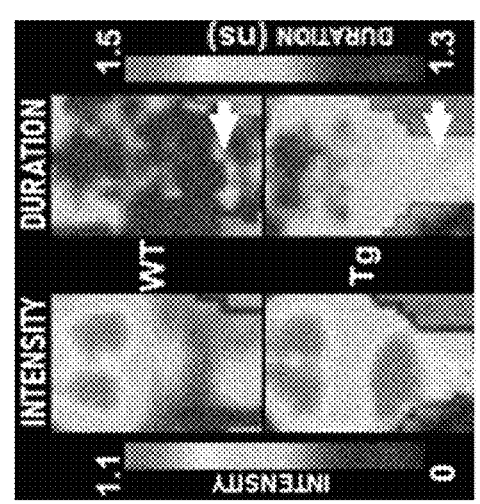

Tg WT
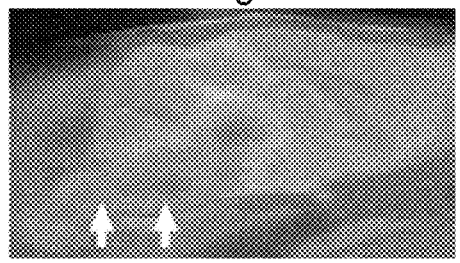
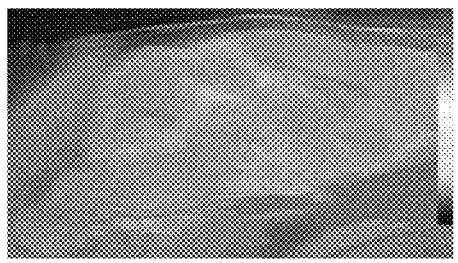
FIG. 6F | FIG. 6G
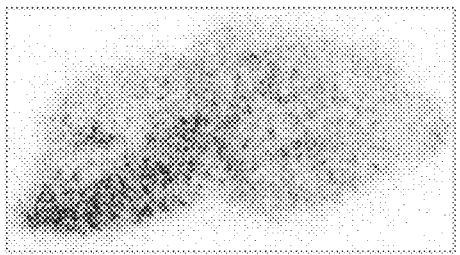
FIG. 6H | FIG. 6I
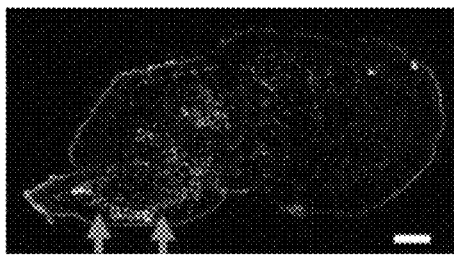
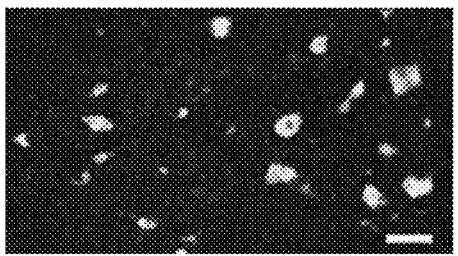
FIG. 6J | FIG. 6K
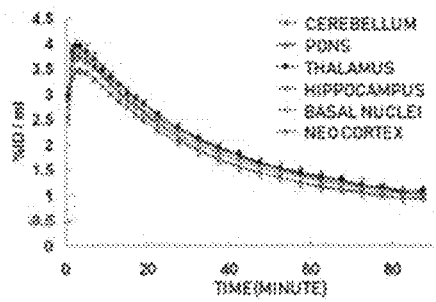
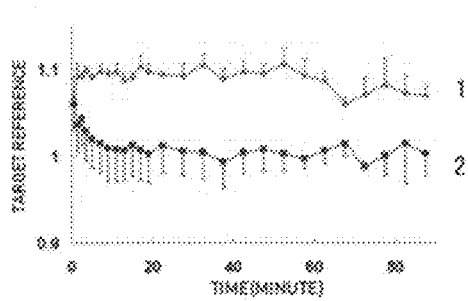
FIG. 6L | FIG. 6M
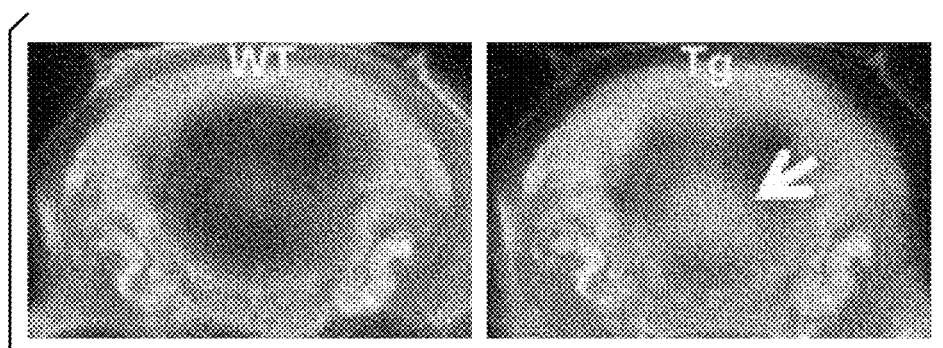
FIG. 7

COMPOUNDS FOR IMAGING TAU PROTEINS THAT ACCUMULATE IN BRAIN

RELATED APPLICATIONS

This application is a continuation of U.S. Ser. No. 16/798,226, filed Feb. 21, 2020, which is a continuation of U.S. Ser. No. 14/346,914, filed Mar. 24, 2014, which is a National Phase entry of PCT/JP2012/083286, filed Dec. 21, 2012, the disclosures of each of which are incorporated by reference in their entireties.

TECHNICAL FIELD

The present invention relates to novel compounds for imaging tau proteins that accumulate in the brain, methods of preparing the compounds, intermediates thereof, and methods of use thereof.

BACKGROUND

In many neurodegenerative diseases such as Alzheimer's disease (AD), tau protein aggregates accumulate in brain cells, generally referred to as "tauopathies." Of these, in familial frontotemporal lobar degeneration (FTLD) (known as frontotemporal dementia and Parkinsonism linked to chromosome 17 (FTDP-17)), genetic mutations in tau genes have been discovered. After that, a study of Tg mice that overexpressed human wild type (WT) or FTDP-17 mutant tau proteins has made it clear that tau amyloid production takes part in the mechanism of neurodegenerative episodes in Alzheimer's disease (AD) and non-Alzheimer-type (non-AD) tauopathies (non-patent literature 1). Also, it has been shown that tau protein aggregates in AD, referred to as neurofibrillary tangles (NFT), are closely linked to disease severity than senile plaques that are made of amyloid β peptides (Aβ) (non-patent literature 2). By contrast with amyloid precursor protein (APP) Tg mice in which Aβ aggregates accumulate without a decrease of neurons, tau Tg mice exhibit a significant decrease of neurons (non-patent literature 3). It is therefore necessary, in future studies, to make the neurotoxicity of fibrous tau proteins in tauopathies pathologically clear, by a comparative evaluation of the living human brain and the mouse brain.

In vivo imaging—for example, positron emission tomography (PET), optical imaging, and nuclear magnetic resonance imaging—is able to visualize Aβ deposits in AD patients and AD mouse models in vivo. As molecular probes to be used thereupon, compounds such as [$^{18}$F]FDDNP, [$^{11}$C]6-OH-BTA-1(PIB), [$^{11}$C]AZD2184, [$^{11}$C]BF-227, [$^{18}$F]-BAY94-9172, and [$^{18}$F]AV-45 are known (patent literatures 1 to 4). Among these, [$^{18}$F]FDDNP has been suggested to bind to both senile plaques and NFTs. However, since this compound has binding to the dense core of Aβ aggregates, interactions with tau pathologies in AD patients have not been shown clearly. In addition, there is a problem that this compound does not bind to tau aggregates in non-AD tauopathy brains without senile plaques, and therefore cannot directly show binding to tau pathologies in vivo. Consequently, development of novel compounds that specifically bind to tau proteins that accumulate in the brain due to AD and non-AD tauopathies, and that allow imaging of tau aggregates, has been sought after.

CITATION LIST

Patent Literature

Patent Literature 1: Japanese Unexamined Patent Application Publication (Translation of PCT Application) No. 2009-519239

Patent literature 2: Japanese Unexamined Patent Application Publication No. 2012-102106

Patent literature 3: Japanese Unexamined Patent Application Publication (Translation of PCT Application) No. 2011-516866

Patent literature 4: Japanese Unexamined Patent Application Publication (Translation of PCT Application) No. 2011-512354

Non-Patent Literature

Non-patent literature 1: Ballatore, C et al., Tau-mediated neurodegeneration in Alzheimer's disease and related disorders, Nat. Rev. Neurosci, 8, 663-72 (2007).

Non-patent literature 2: Arriagada, P. V. et al., Neurofibrillary tangles but not senile plaques parallel duration and severity of Alzheimer's disease, Neurology 42, 631-639 (1992).

Non-patent literature 3: Yoshiya, Y. et al., Synapse loss and microglial activation precede tangles in a P301S tauopathy mouse model, Neuron 53, 337-351 (2007).

SUMMARY OF INVENTION

Technical Problem

It is an object of the present invention to provide novel compounds that can specifically bind to tau proteins that accumulate in the brain.

Solution to Problem

The present inventors have tested compounds of various dimensions for binding to tau aggregates. As a result of this, it has been found out that compounds having a basic structure of specific length ranging from 13 to 19 Å exhibit affinity to tau aggregates in living organisms including AD and non-AD tauopathy patients. From this perspective, the present inventors have developed novel compounds that can specifically bind to tau aggregates.

The present invention provides a compound represented by the following formula (I), a pharmaceutically acceptable salt thereof, or a solvate thereof:

[Formula 1]

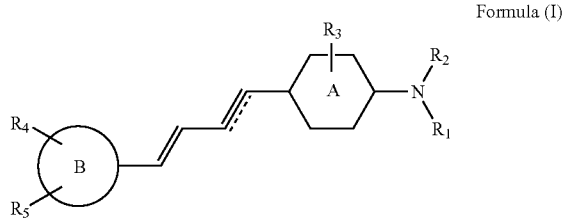

Formula (I)

wherein:

$R_1$ and $R_2$ are each separately selected from the group consisting of hydrogen, alkyl, alkenyl, acyl, and hydroxyalkyl;

$R_3$ is hydrogen or halogen;

ring A is a benzene ring or a pyridine ring;

ring B is selected from the group consisting of the following formulas (i), (ii), (iii), and (iv):

[Formula 2]

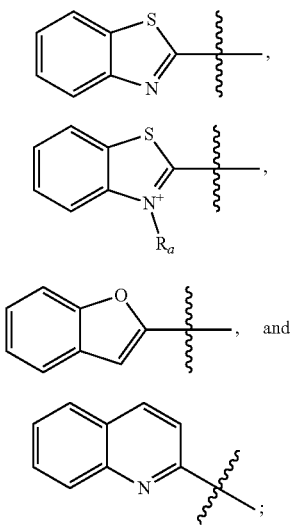

in the formula (ii), Ra is alkyl;

$R_4$ and $R_5$ are each separately selected from the group consisting of hydrogen, hydroxy, alkoxy, haloalkoxy, halohydroxyalkoxy, and aminoalkyl; and

[Formula 3]

represents a double bond or a triple bond. In one embodiment, in the compound of the formula (I), one or more atoms are a radioisotope of the atom(s).

Advantageous Effects of Invention

The compounds of the present invention can specifically bind to tau aggregates. Consequently, it is possible to image tau proteins that accumulate in the brain using the compounds of the present invention.

After being administered in mammals, the compounds of the present invention can quickly pass the blood brain barrier. The half-life of the compounds of the present invention to last in the brain is approximately 10 minutes, and therefore has an advantage of having little influence on the human body. Also, the compounds of the present invention have fluorescence properties, so that the compounds of the present invention, when labeled with a radioactive isotope, are capable of double imaging, by the fluorescence properties and radioactivity of the compounds themselves.

BRIEF DESCRIPTION OF DRAWINGS

FIGS. 1A and 1B show confocal fluorescence images of frontal cortex slices of AD patients. FIG. 1A shows images that are stained with PIB, FSB and AT8, and with an anti-AβN3 (pE) antibody. FIG. 1B shows images that are stained with PBB1 to PBB5, and with an anti-AβN3 (pE) antibody.

FIG. 3B shows the results of in vitro labeling of AD NFTs and NFT-like tau inclusions in PS19 mice using compounds other than PBB1 to PBB5.

FIGS. 4A-4J shows the results of non-invasive near-infrared imaging using PBB5; FIG. 4A shows a reference autofluorescent signal (center panel) laid over a visible light image (left panel) of the shaved head part of non-Tg WT mice. Elliptically-shaped regions of interest (ROIs) of the frontal cortex (FC), the brain stem (BS), and the cervical cord (SC) are shown in the right panel. FIG. 4B shows fluorescence intensity maps of PBB5 (0.1 mg/kg) in 12-month-old WT mice (upper part) and PS19 mice (lower part), before and 30 minutes and 240 minutes after the intravenous administration. FIGS. 4C, 4D and 4E show the ratios of fluorescence intensity in the BS (c) and SC (d) ROIs, to the FC ROI, in the WT mice (white: n=7) and the PS19 mice (black: n=7). FIG. 4F shows a distribution diagram of the ratios of SC and BS to FC 240 minutes later, against the number of FSB-positive NFT-like pathologies per unit area of 20-μm tissue sections of the tau Tg mice. FIG. 4G shows the fluorescence intensity (left) and the fluorescence duration (right) in 11-month-old WT mice (upper part) and PS19 mice (lower part) 120 minutes after the intravenous injection of PPB5. FIG. 4H shows TPSF curve of SC and FC spots 120 minutes after injection in 11 month-old WT mice and Tg mice. FIG. 4I shows average durations of fluorescence in the FC, BS, and SC ROIs in the WT mice (white; n=7) and Tg mice (black; n=7) 120 minutes after the injection. FIG. 4J shows a distribution diagram of the fluorescence duration periods in the BS and SC ROIs 120 minutes after the injection, against the number of FSB-positive NFT-like pathologies per unit area in 20 μm-thick tissue sections of the Tg mice.

FIGS. 5G and 5H show that PBB3 remains bound to tau inclusions, while FIG. 5I shows that all PBB3 had disappeared from WT mice within 300 seconds.

FIG. 6A shows the results of PET and autoradiographic detections of tau pathologies of PS19 mice using [$^{11}$C]PBB2 and [$^{11}$C]PBB3; FIG. 6B shows autoradiograms of 20 μm-thick brain sections from non-Tg WT mice and PS19 mice treated with [$^{11}$C]PBB2 or [$^{11}$C]PBB3; FIG. 6C shows sagittal-plane and coronal-plane PET images and MRI images, obtained by averaging the dynamic scan data from 60 to 90 minutes after the intravenous administration of [$^{11}$C]PBB3. FIG. 6D shows FSB stain images of a brain section extracted from the PS19 mice after PET scanning (a sagittal plane image (left panel) and a coronal plane image (center panel), and a high-magnification image (right panel)) of fibrous tau inclusions. FIG. 6E shows the time-activity curves (left panel) in the striatums (ST) and brain stem (BS) of the PS19 mice and WT mice, and, the BS-to-ST ratios of radioactivity (right panel) (in each, n=5). FIGS. 6H and 6I show ex vivo autoradiography images of the mice shown in FIGS. 6F and 6G. FIGS. 6J and 6K show FSB stain images, using the same samples as the samples from which the autoradiography images are obtained. FIG. 6L shows time-activity curves in a plurality of brain tissues of WT mice. FIG. 6M shows the ratios of radioactivity in the brain stem to the striatum, in PS19 mice (1 in the drawing) and WT mice (2 in the drawing) (n=5), over the imaging period.

FIG. 7 shows coronal-plane PET images in the brains of WT mice (left panel) and PS19 Tg mice (right panel) to which [$^{11}$C]mPBB5 is injected.

DESCRIPTION OF EMBODIMENTS

1. Definitions

Figure 2:
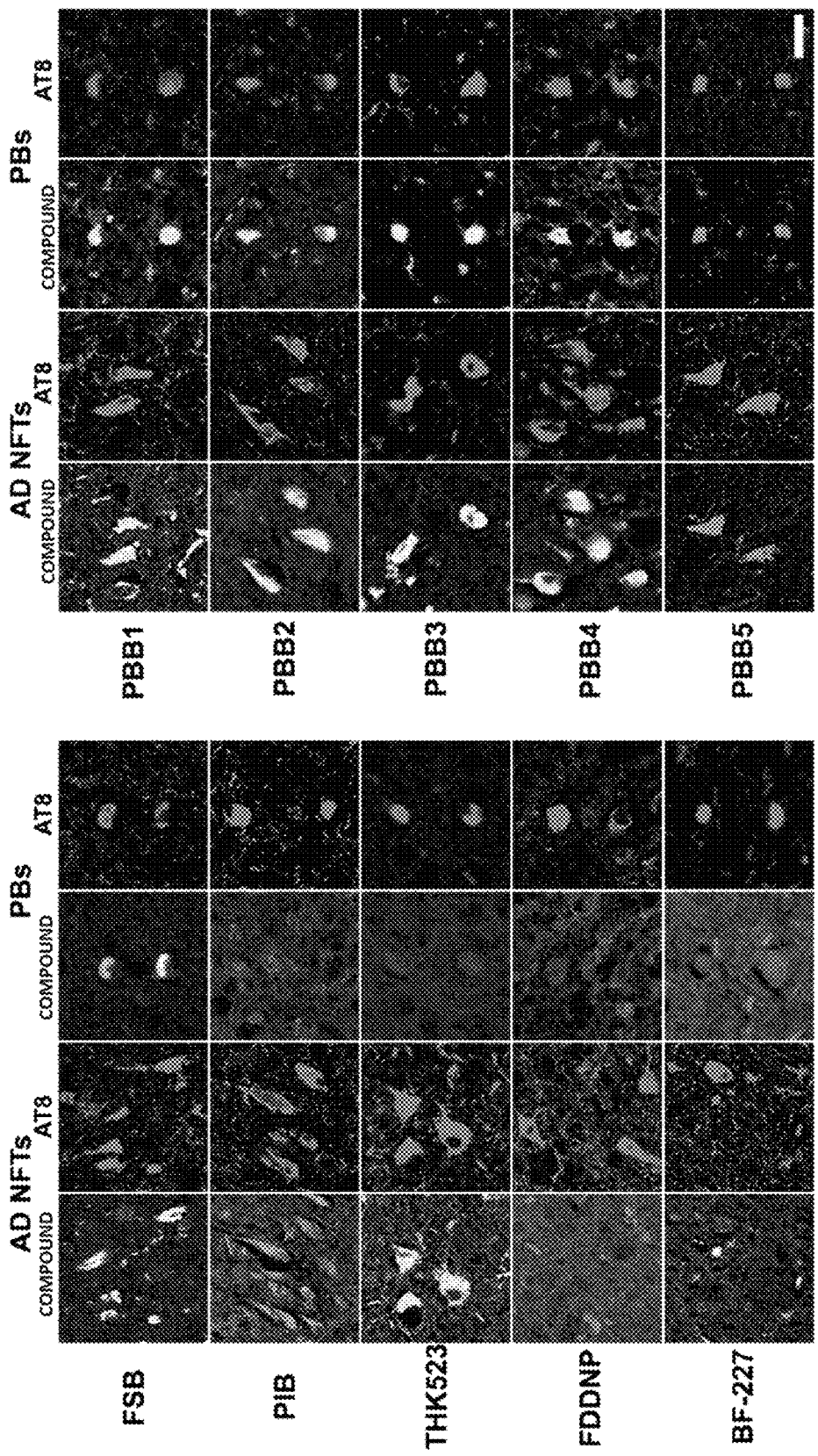
FIG. 2 shows double fluorescence staining images of AD NFTs and Pick's disease by FSB, PIB, THK523, FDDNP, BF-227, PBB1 to PBB5, and AT8.

The term "alkyl" means a monovalent group that is produced when aliphatic saturated hydrocarbon misses one hydrogen atom. An alkyl has, for example, 1 to 15 carbon atoms, and typically has 1 to 10, 1 to 8, 1 to 6, 1 to 5, 1 to 4, 1 to 3, 1 to 2, or 2 to 6 carbon atoms. An alkyl may be a straight chain or may be branched. Examples of alkyls include, but are by no means limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl. An alkyl may furthermore be substituted by an adequate substituent.

In this description, 1 to 15, 1 to 10, 1 to 8, 1 to 6, 1 to 5, 1 to 4, 1 to 3, 1 to 2, 2 to 8, 2 to 6, 2 to 4, 3 to 8, 3 to 6, 4 to 8, and 4 to 6 carbon atoms will be represented as $C_{1-15}$, $C_{1-10}$, $C_{1-8}$, $C_{1-6}$, $C_{1-5}$, $C_{1-4}$, $C_{1-3}$, $C_{1-2}$, $C_{2-8}$, $C_{2-6}$, $C_{2-4}$, $C_{3-8}$, $C_{3-6}$, $C_{4-8}$, and $C_{4-6}$, respectively.

The term "cycloalkyl" means a monovalent group that is produced when aliphatic saturated hydrocarbon forming a carbocyclic ring misses one hydrogen atom. A cycloalkyl has, for example, 3 to 10 carbon atoms, and typically has 3 to 8, 3 to 6, 3 to 5, 3 to 4, 4 to 5, 4 to 6, or 4 to 8 carbon atoms. Examples of cycloalkyls include, but are by no means limited to, cyclopropane, cyclobutane, cyclopentane, cyclohexane, cycloheptane, and cyclooctane. A cycloalkyl may furthermore be substituted by an adequate substituent.

The term "alkenyl" means an unsaturated aliphatic hydrocarbon group that has at least one double bond. An alkenyl has, for example, 2 to 15 carbon atoms, and typically has, 2 to 10, 2 to 8, 2 to 6, 2 to 5, 2 to 4, 2 to 3, 3 to 6, 3 to 8, 4 to 6, 4 to 7, or 4 to 8 carbon atoms. An alkenyl may be a straight chain or may be branched. Examples of alkenyls include, but are by no means limited to, to be specific, vinyl (—CH=CH$_2$), allyl (—CH$_2$CH=CH$_2$), —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, 1,3-butadienyl (—CH=CH—CH=CH$_2$), and hepta-1,6-diene-4-yl (—CH$_2$—(CH$_2$CH=CH$_2$)$_2$). An alkenyl may furthermore be substituted by an adequate substituent.

The term "alkynyl" means an unsaturated aliphatic hydrocarbon group that has at least one triple bond. An alkynyl has, for example, 2 to 15 carbon atoms, and typically has 2 to 10, 2 to 8, 2 to 6, 2 to 5, 2 to 4, 2 to 3, 3 to 6, 4 to 6, 4 to 7, or 4 to 8 carbon atoms. An alkynyl may be a straight chain or may be branched. Examples of alkynyls include, but are by no means limited to, ethynyl (—CECH), —CECH (CH$_3$), —CEC(CH$_2$CH$_3$), —CH$_2$CECH, —CH$_2$CEC(CH$_3$), and —CH$_2$CEC(CH$_2$CH$_3$). An alkynyl may furthermore be substituted by an adequate substituent.

The term "acyl" means a group that is represented by "—CO—R." Here, R is, for example, an alkyl, an alkenyl, or an alkynyl. Examples of acyls include, but are by no means limited to, acetyl (—COCH3), ethylcarbonyl, propylcarbonyl, pentylcarbonyl, cyclohexylcarbonyl, octylcarbonyl, 2-ethylhexylcarbonyl, dodecylcarbonyl, phenylcarbonyl, benzylcarbonyl, naphthylcarbonyl and pyridylcarbonyl. An acyl may furthermore be substituted by an adequate substituent.

The term "hydroxy" or "hydroxyl" means —OH. The term "hydroxyalkyl" means an alkyl group that is substituted by a hydroxy group (—OH). Examples of hydroxyalkyls include, but are by no means limited to, hydroxymethyl (—CH$_2$OH), 2-hydroxyethyl (—CH$_2$CH$_2$OH), 1-hydroxyethyl (—CH(OH)CH$_3$), 3-hydroxypropyl (—CH$_2$CH$_2$CH$_2$OH), 2-hydroxypropyl (—CH$_2$CH(OH)CH$_3$), and 1-hydroxypropyl (—CH(OH)CH$_2$CH$_3$). A hydroxyalkyl may furthermore be substituted by an adequate substituent. The term "halogen" or "halo" means fluoro (—F), chloro (—Cl), bromo (—Br), and iodine (—I).

The term "alkoxy" means an alkyl that is bound to other groups via oxygen atoms (that is, —O-alkyl). Examples of alkoxys include, but are by no means limited to, methoxy (—O-methyl), ethoxy (—O-ethyl), propoxy (—O-propyl), —O-isopropyl, —O-2-methyl-1-propyl, —O-2-methyl-2-propyl, —O-2-methyl-I-butyl, —O-3-methyl-1-butyl, —O-2-methyl-3-butyl, —O-2,2-dimethyl-1-propyl, —O-2-methyl-1-pentyl, 3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-1-butyl, O-2-ethyl-1-butyl, —O-butyl, —O-isobutyl, —O-t-butyl, —O-pentyl, —O-isopentyl, O-neopentyl, and —O-hexyl. An alkoxy may furthermore be substituted by an adequate substituent.

The term "haloalkyl" means an alkyl that is substituted by at least one halogen. Haloalkyls include fluoroalkyl, chloroalkyl, bromoalkyl, and iodoalkyl. Examples of haloalkyls include, but are by no means limited to, fluoromethyl, chloromethyl, bromomethyl, iodomethyl, fluoroethyl, chloroethyl, bromoethyl, iodoethyl, fluoropropyl, chloropropyl, bromopropyl, iodopropyl, fluorobutyl, chlorobutyl, bromobutyl, iodobutyl, fluoropentyl, chloropentyl, bromopentyl, iodopentyl, fluorohexyl, chlorohexyl, bromohexyl, iodohexyl, fluoroheptyl, chloroheptyl, bromoheptyl, iodoheptyl, fluorooctyl, chlorooctyl, bromooctyl, and iodooctyl. A haloalkyl may furthermore be substituted by an adequate substituent.

The term "haloalkoxy" means an alkoxy that is substituted by at least one halogen (that is, —O-haloalkyl). Haloalkoxys include fluoroalkoxy, chloroalkoxy, bromoalkoxy, and iodoalkoxy.

The term "halohydroxyalkyl" means a hydroxyalkyl that is substituted by halogen. Halohydroxyalkyls include fluorohydroxyalkyl, chlorohydroxyalkyl, bromohydroxyalkyl, and iodohydroxyalkyl. Examples of halohydroxyalkyls include 1-bromo-3-propanol, 1-iodo-3-propanol, 1-bromo-2-ethanol, 1-iodo-2-ethanol, 1-bromo-1-methanol or 1-iodo-1-methanol.

The term "halohydroxyalkoxy" means a haloalkoxy that is substituted by a hydroxy group. Halohydroxyalkoxys include fluorohydroxyalkoxy, chlorohydroxyalkoxy, bromohydroxyalkoxy, and iodohydroxyalkoxy. Examples of halohydroxyalkoxys include —O—CH(F)(OH), —O—CH$_2$CH(F)(OH), —O—CH(OH—CH$_2$(F), —O—CH$_2$—CH(F)(OH), —O—CH(OH—CH$_2$—CH$_2$(F), —O—CH$_2$—CH(OH—CH$_2$ (F), —O—CH$_2$—CH(OH)—CH$_2$ (F), —O—CH(CH$_2$—F)(CH$_2$OH) and —O—CH$_2$—CH$_2$—CH(F)(OH).

The term "nitro" means —NO$_2$. The term "amino" means —NH$_2$. The term "aminoalkyl" means an alkyl group that is substituted by an amino group. Examples of aminoalkyls include, but are by no means limited to, aminomethyl, aminoethyl, aminopropyl, aminoisopropyl, aminobutyl, aminopentyl, aminohexyl, and aminooctyl.

The term "substituent" means one or more atoms or an atomic group that is introduced in a given chemical structural formula. Examples of substituents include, for example, $C_{1-8}$ alkyls (methyl, ethyl, n-propyl, iso-propyl, n-butyl, sec-butyl, iso-butyl, tert-butyl, or n-hexyl, or its isomer, and so on), $C_{2-8}$ alkenyls (vinyl, allyl, —CH═CH($CH_3$), —CH═C($CH_3$)$_2$, —C($CH_3$)═$CH_2$, —C($CH_3$)═CH($CH_3$), —C($CH_2CH_3$)═$CH_2$ and so on), $C_{2-8}$ alkynyl (ethynyl, —C≡CH($CH_3$), ($CH_3$), —$CH_2$C≡C($CH_2CH_3$), —$CH_2$C≡CH, —$CH_2$C≡C($CH_3$), —$CH_2$C≡C($CH_2CH_3$) and so on), alkoxy, hydroxy, halogen, haloalkyl, cycloalkyl (cyclopropyl, cyclobutyl, cyclopentyl, or cyclohexyl and so on), amino, nitro, acyl (acetyl and so on) (—$COCH_3$), carboxyl (—COOH), ester (—$COOR^x$, where Rx is $C_{1-6}$ alkyl and so on), amide (—$CONR^yR^z$, where $R^y$ and $R^z$ are individually H or $C_{1-6}$ alkyl and so on), thiol (—SH), sulfonic acid (—$SO_3H$), nitrile (—CN), aromatic rings (aryl, phenyl, benzoyl, or naphthalenyl and so on), heterocyclic rings (pyrrolidinyl, tetrahydrofuranyl, pyrrolyl, furanyl, thiophenyl, piperidinyl, oxanyl, or pyridinyl and so on), and so on.

The term "pharmaceutically acceptable salt" means a salt that is not harmful to mammals, especially humans. Pharmaceutically acceptable salts can be formed using non-toxic acids or bases, including mineral acids or inorganic bases, or organic acids or organic bases. Examples of pharmaceutically acceptable salts include metal salts formed with aluminum, calcium, lithium, magnesium, potassium, sodium, zinc and so on, and organic salts formed with lysine, N,N'-dibenzylethylenediamine, chloroprocaine, choline, diethanolamine, ethylenediamine, meglumine (N-methyl-glucamine), procaine and so on. Also, pharmaceutically acceptable salts contain acid-addition salts and base-addition salts.

The term "pharmaceutically acceptable carriers" means pharmaceutically acceptable materials, compositions, or vehicles such as physiological saline solutions, liquid or solid fillers, diluents, solvents, or encapsulants. Examples of pharmaceutically acceptable carriers include water, saline water, physiological saline water or phosphate buffered saline water (PBS), sodium chloride injection solution, Ringer's injection solution, isotonic dextrose injection solution, sterile water injection solution, dextrose, and lactated Ringer's injection solution.

The term "effective dose" refers to the amount of a compound or a composition which will have a targeted effect. For example, in some embodiments, the effective dose may refer to the amount of a compound or a composition which will enable tau imaging.

The term "solvate" means a solvent-containing compound that is formed by association of one or a plurality of solvent molecules to the compounds of the present invention. Solvates include, for example, monosolvates, disolvates, trisolvates, and tetrasolvates. Also, solvates include hydrates. The term "hydrate" means a compound further containing a stoichiometric or a non-stoichiometric amount of water constrained by non-covalent bonding intermolecular force, or a salt thereof. Hydrates include monohydrates, dihydrates, trihydrates, and tetrahydrates.

The term "treatment" means moderating or remitting the progress, severity and/or period of a disease or condition. The term "prevention" means reducing the danger of catching or making worse a predetermined disease or condition, or reducing or suppressing the recurrence, start or progress of a predetermined disease or condition, or one or a plurality of symptoms.

The term "tau imaging" means imaging tau proteins that accumulate in the brain. This imaging may be performed by positron emission tomography (PET), fluorescence microscopy measurement, multi-photon imaging, two-photon imaging, near-infrared fluorescence imaging, autoradiography, and single-photon emission computed tomography (SPECT).

2. Compounds of the Present Invention

The present invention provides a compound represented by the following formula (I), a pharmaceutically acceptable salt thereof, or a solvate thereof:

[Formula 4]

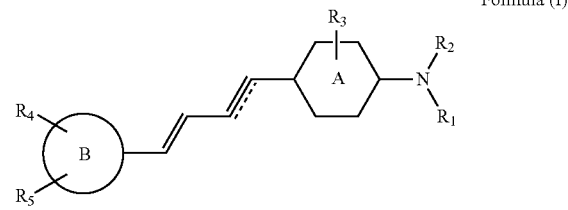

Formula (I)

Wherein:
$R_1$ and $R_2$ are each separately selected from the group consisting of hydrogen, alkyl, alkenyl, acyl, and hydroxalkyl;
$R_3$ is hydrogen or halogen;
ring A is a benzone ring or a pyridine ring;
ring B is selected from the group consisting of the following formulas (i), (ii), (iii), and (iv):

[Formula 5]

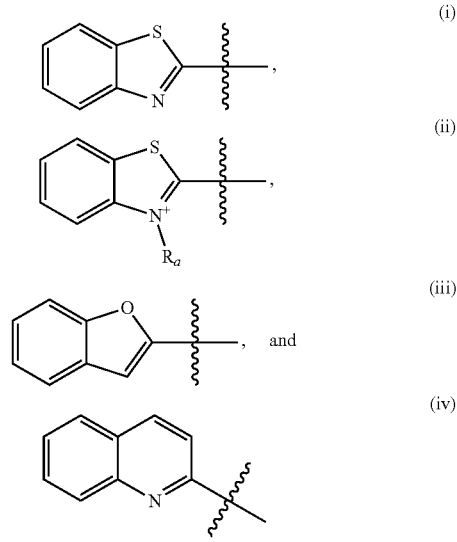

in the formula (ii), $R_a$ is alkyl;
$R_4$ and $R_5$ are each separately selected from the group consisting of hydrogen, hydroxyl, alkoxy, haloalkoxy, halohydroxyalkoxy, and aminoalkyl; and

[Formula 6]

represents a double bound or a triple bond.

In one embodiment, ring B is the formula (i) or the formula (ii). In another embodiment, ring B is the formula (i). In yet another embodiment, ring B is the formula (ii). When ring B is the formula (ii), the type of the counter anion is not particularly limited, and may be p-toluenesulfonate, I$^{-1}$ and or the like. In one embodiment, ring B is the formula (iii). In another embodiment, ring B is the formula (iv).

When ring B is the formula (1), $R_4$ and $R_5$ can be at substitutable positions in the benzothiazole ring of the formula (1). Preferably, $R_4$ and $R_5$ are at position 6 and position 5 in the benzothiazole ring of the formula (i), respectively. When ring B is the formula (ii), $R_4$ and $R_5$ can be at substitutable positions in the benzothiazolium ring of the formula (ii). Preferably, $R_4$ and $R_5$ are at position 6 and position 5 in the benzothiazolium ring of the formula (ii), respectively. When ring B is the formula (iii), $R_4$ and $R_5$ can be at substitutable positions in the benzofuran ring of the formula (iii). Preferably, $R_4$ and $R_5$ are at position 5 and position 6 in the benzofuran ring of the formula (iii), respectively. When ring B is the formula (iv), $R_4$ and $R_5$ can be at substitutable positions in the quinoline ring of the formula (iv). Preferably, $R_4$ and $R_5$ are at position 6 and position 7 in the quinoline ring of the formula (iv), respectively.

In one embodiment, ring A is a pyridine ring. In another embodiment, ring A is a benzene ring. Preferably, ring A is the pyridine ring represented by the following structural formula, in the orientation of the structural formula of the formula (I).

[Formula 7]

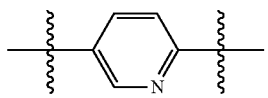

In one embodiment, $R_1$ and $R_2$ are both hydrogen. In one embodiment, $R_1$ and $R_2$ are each separately hydrogen or alkyl, especially $C_{1-8}$ alkyl, and preferably methyl. In another embodiment, $R_1$ is hydrogen, $R_2$ is alkyl, especially $C_{1-6}$ alkyl, and preferably methyl. In yet another embodiment, $R_1$ and $R_2$ are both alkyl, especially $C_{1-6}$alkyl, and preferably methyl.

In one embodiment, $R_1$ and $R_2$ are each separately hydrogen or alkenyl, especially $C_{2-8}$ alkenyl, and preferably allyl (—$CH_2CH=CH_2$) or hepta-1,6-diene-4-yl (—$CH_2$—($CH_2CH=CH_2$)$_2$). In another embodiment, $R_1$ is hydrogen, $R_2$ is alkenyl, especially $C_{1-8}$ alkenyl, and preferably allyl (—$CH_2CH=CH_2$) or hepta-1,6-diene-4-yl (—$CH_2$—($CH_2CH=CH_2$)$_2$). In yet another embodiment, $R_1$ and $R_2$ are both alkenyl, especially C1-8 alkenyl, and preferably allyl (—$CH_2CH=CH_2$) or hepta-1,6-diene-4-yl (—$CH_2$—($CH_2CH=CH_2$)$_2$).

In one embodiment, $R_1$ and $R_2$ are each separately hydrogen or acyl, especially $C_{1-8}$ acyl, and preferably acetyl (—$COCH_3$). In another embodiment, $R_1$ is hydrogen, $R_2$ is acyl, especially $C_{1-8}$ acyl, and preferably acetyl (—$COCH_3$). In yet another embodiment, $R_1$ and $R_2$ are both acyl, especially $C_{1-8}$ acyl, and preferably acetyl (—$COCH_3$).

In one embodiment, $R_1$ and $R_2$ are each separately hydrogen or hydroxyalkyl, especially hydroxy$C_{1-8}$alkyl, preferably hydroxypropyl, and more preferably 3-hydroxypropyl (—$CH_2CH_2CH_2OH$). In another embodiment, $R_1$ is hydrogen, $R_2$ is hydroxyalkyl, especially hydroxy$C_{1-8}$alkyl, preferably hydroxypropyl, and more preferably 3-hydroxypropyl (—$CH_2CH_2CH_2OH$). In yet another embodiment, $R_1$ and $R_2$ are both hydroxyalkyl, especially hydroxy$C_{1-8}$alkyl, preferably hydroxypropyl, and more preferably 3-hydroxypropyl (—$CH_2CH_2CH_2OH$).

In one embodiment, $R_3$ is hydrogen. In another embodiment, $R_3$ is halogen, that is, F, Cl, Br or I. Preferably, $R_3$ is F. Preferably, $R_3$ is $^{18}$F. In the orientation of the structural formula of the formula (I), $R_3$ preferably assumes the following position.

[Formula 8]

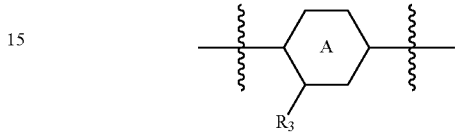

In the orientation of the structural formula of the formula (I), ring A and $R_3$ preferably have the following relationship.

[Formula 9]

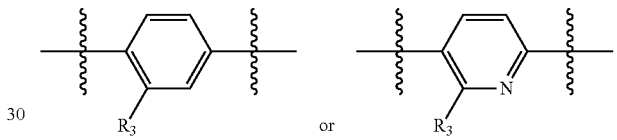

In one embodiment, $R_a$ is alkyl, preferably $C_{1-8}$ alkyl, and more preferably methyl or ethyl. In one embodiment, $R_4$ and $R_5$ are both hydrogen. In one embodiment, $R_4$ and $R_5$ are each separately hydrogen or hydroxy. In another embodiment, $R_4$ is hydroxy, and $R_5$ is hydrogen. In yet another embodiment, $R_4$ is hydrogen, and $R_5$ is hydroxy. In yet another embodiment, $R_4$ and $R_5$ are both hydroxy.

In one embodiment, $R_4$ and $R_5$ are each separately hydrogen or alkoxy, especially methoxy. In another embodiment, $R_4$ is alkoxy, especially methoxy, and $R_5$ is hydrogen. In yet another embodiment, $R_4$ is hydrogen, $R_5$ is alkoxy, especially methoxy. In yet another embodiment, $R_4$ and $R_5$ are both alkoxy, especially methoxy.

In one embodiment, $R_4$ and $R_5$ are each separately hydrogen or halohydroxyalkoxy, especially fluorohydroxyalkoxy, preferably fluorohydroxy$C_{1-3}$alkoxy, and more preferably —O—$CH_2$—CH(OH)—$CH_2$(F) or —O—CH($CH_2$—F) ($CH_2OH$). In another embodiment, $R_4$ is hydrogen, $R_5$ is halohydroxyalkoxy, especially fluorohydroxyalkoxy, preferably fluorohydroxy$C_{1-3}$alkoxy, more preferably —O—$CH_2$—CH(OH)—$CH_2$(F) or —O—CH($CH_2$—F) ($CH_2OH$). In yet another embodiment, $R_4$ and $R_5$ are both halohydroxyalkoxy, especially fluorohydroxyalkoxy, preferably fluorohydroxy$C_{1-3}$alkoxy, more preferably —O—$CH_2$—CH(OH)—$CH_2$(F) or —O—CH($CH_2$—F) ($CH_2OH$). In yet another embodiment, $R_4$ and $R_5$ are both halohydroxyalkoxy, especially fluorohydroxyalkoxy, preferably fluorohydroxy$C_{1-3}$alkoxy, and more preferably —O—$CH_2$—CH(OH)—$CH_2$(F) or —O—CH($CH_2$—O ($CH_2OH$). In one embodiment, fluorohydroxyalkoxy contains a radioisotope. Preferably, this fluorohydroxyalkoxy is —O—$CH_2$—CH(OH)—$CH_2$($^{18}$F) or —O—CH($CH_2$—$^{18}$F) ($CH_2OH$).

In one embodiment, $R_4$ and $R_5$ are each separately hydrogen or aminoalkyl, especially aminomethyl or aminoethyl. In another embodiment, $R_4$ is aminoalkyl, especially aminomethyl or aminoethyl, and $R_5$ is hydrogen. In yet another embodiment, $R_4$ is hydrogen, and $R_5$ is aminoalkyl, especially aminomethyl or aminoethyl. In yet another embodiment, $R_4$ and $R_5$ are both aminoalkyl, especially aminomethyl or aminoethyl.

In one embodiment,

[Formula 10]

═══ is a double bond. In another embodiment,

[Formula 11]

═══ is a triple bond.

In one embodiment, the following compound is excluded from the compound of the formula (I).

[Formula 12]

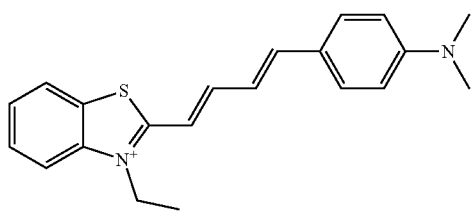 [SMILES: CC[n+]1c(/C=C/C=C/c2ccc(N(C)C)cc2)sc2ccccc21]

In one embodiment, the compound of the formula (I) is a compound represented by the following formula (II):

[Formula 13]

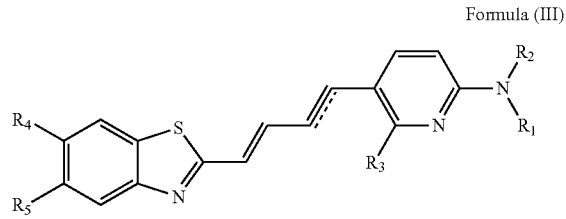

wherein $R_1$ to $R_5$, and

[Formula 14]

═══ have been defined above in the compound of the formula (I).

In one embodiment, the compound of the formula (I) is a compound represented by the following formula (III):

[Formula 15]

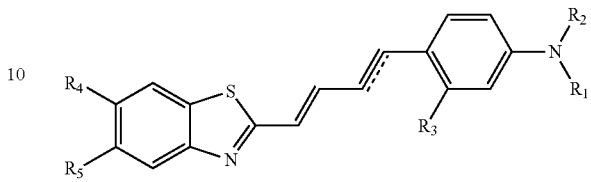

wherein $R_1$ to $R_5$, and

[Formula 16]

═══ have been defined in the compound of the formula (I).

In one embodiment, the compound of the formula (I) is a compound represented by the following formula (IV).

[Formula 17]

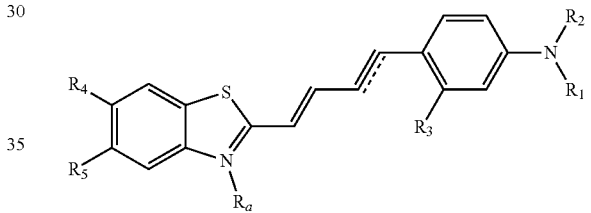

wherein $R_1$ to $R_5$, $R_a$ and

[Formula 18]

═══ have been defined in the compound of the formula (I).

In one embodiment, the compound of the formula (I) is a compound represented by the following formula (V).

[Formula 19]

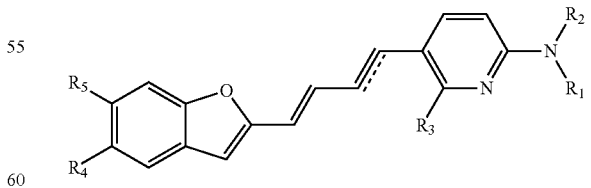

wherein $R_1$ to $R_5$, and

[Formula 20]

═══ have been defined in the compound of the formula (I).

In one embodiment, the compound of the formula (I) is a compound represented by the following formula (VI).

[Formula 21]

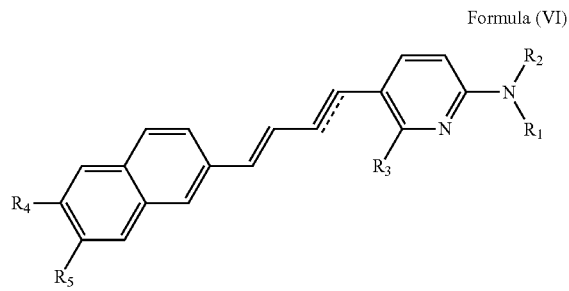

Formula (VI)

wherein $R_1$, to $R_5$, and

[Formula 22]

≡≡≡ have been defined in the compound of the formula (I).

In one embodiment, in the compounds of the formulas (I) to (VI), one or more atoms are a radioisotope of the atom(s).

The radioisotope may be selected from the group consisting of $^{15}O$, $^{13}N$, $^{11}C$, $^{18}F$ and so on, but is not particularly limited. Preferably, the radioisotope is $^{11}C$ or $^{19}F$. Of these, considering that the half-life of $^{11}C$ is approximately 20 minutes and the half-life of $^{18}F$ is approximately 110 minutes, a compound that is labeled with $^{18}F$ may have a higher commercial value. Consequently, most preferably, the radioisotope is $^{18}F$.

Preferably, one or more of $R_1$ to $R_5$ are groups that contain a radioisotope. More preferably, one or both of $R_1$ and $R_2$ are groups that contain a radioisotope, and are, for example, groups that contain $^{11}C$ (for example, [$^{11}C$]alkyl to contain $^{11}CH_3$). Even more preferably, $R_3$ is a group to contain a radioisotope, and is, for example, $^{-18}F$. More preferably, one or both of $R_4$ and $R_5$ are groups that contain a radioisotope, and are, for example, groups to contain $^{11}C$ (for example, [$^{11}C$]alkoxy to contain $-O-CH_2-CH(OH)-CH_2(^{18}F)$ and $-O-CH(CH_2-^{18}F(CH_2OH))$. Here, [$^{11}C$]alkyl indicates that one or more carbon atoms in the carbon atoms constituting alkyl are $^{11}C$. [$^{11}C$]alkoxy indicates that one or more carbon atoms in the carbon atoms constituting alkoxy are $^{11}C$. [$^{18}F$]fluorohydroxyalkoxy means a group in which 18F is bound to hydroxyalkoxy.

Specific examples of the compounds of the present invention include the following compounds:

TABLE 1

| Name | Name of Compound | Structural Formula | Synthesis Embodiment | Fluorescence property binding capacity |
|------|------------------|--------------------|----------------------|----------------------------------------|
| (1) PBB1 | 4-((1E,3E)-4-(benz[d]thiazole-2-yl)buta-1,3-dienyl)-N,N-dimethylaniline | | 1 | |
| (2) PBB2 | 2-((1E,3E)-4-(4-(methylamino)phenyl)buta-1,3-dienyl)benz[d]thiazole-6-ol | | 2 | |
| (3) PBB3 | 2-((1E,3E)-4-(6-(methylamino)pyridine-3-yl)buta-1,3-dienyl)benz[d]thiazole-6-ol | | 3 | |
| (4) PBB4 | 2-((1E,3E)-4-(6-(methylamino)pyridine-3-yl)buta-1,3-dienyl)benz[d]thiazole-5,6-diol | | 4 | |

TABLE 1-continued

| Name | Name of Compound | Structural Formula | Synthesis Embodiment | Fluorescence property binding capacity |
|---|---|---|---|---|
| (5) PBB5 | 2-((1E,3E)-4-(4-(dimethylamino)phenyl)buta-1,3-dienyl)-3-ethylbenzo[d]thiazole-3-ium | | | — |
| (6) mPBB5 | 2-((1E,3E)-4-(4-(dimethylamino)phenyl)buta-1,3-dienyl)-3-ethyl-6-methoxybenzo[d]thiazole-3-ium | | 5 | |
| (7) PBB2.1 | (E)-2-(4-(4-(dimethylamino)phenyl)buta-1-en-3-ynyl)benz[d]thiazole-6-ol | | 6 | |
| (8) PBB2.2 | (E)-2-(4-(4-(methylamino)phenyl)buta-1-en-3-ynyl)benz[d]thiazole-6-ol | | 7 | |
| (9) PBB2.3 | (E)-2-(4-(4-aminophenyl)buta-1-en-3-ynyl)benz[d]thiazole-6-ol | | 8 | |
| (10) PBB3.1 | (E)-2-(4-(6-(dimethylamino)pyridine-3-yl)buta-1-en-3-ynyl)benz[d]thiazole-6-ol | | 9 | |
| (11) PBB3.2 | (E)-2-(4-(6-(methylamino)pyridine-3-yl)buta-1-en-3-ynyl)benz[d]thiazole-6-ol | | 10 | |
| (12) PBB3.2N | (E)-5-(4-(6-(aminomethyl)benz[d]thiazole-2-yl)buta-3-en-1-ynyl)-N-methylpyridine-2-amine | | 11 | |

TABLE 1-continued

| Name | Name of Compound | Structural Formula | Synthesis Embodiment | Fluorescence property binding capacity |
|---|---|---|---|---|
| (13) Core 1-4 | 2-((1E,3E)-4-(4-(aminophenyl)buta-1,3-dienyl)-6-methoxy benzo[d]thiazole-5-ol | | 12 | |
| (14) Core 1-5 | N-(4-((1E,3E)-4-(5,6-dimethoxybenzo[d]thiazole-2-yl)buta-1,3-dienyl)phenyl) acetamide | | 13 | |
| (15) Core1-11 | 3-(4-((1E,3E)-4-(5,6-dimethoxybenzo[d]thiazole-2-yl)buta-1,3-dienyl)phenyl amino)propanol-1-ol | | 14 | |
| (16) Core1-15 | 4-((1E,3E)-4-(5,6-dimethoxybenzo[d]thiazole-2-yl)buta-1,3-dienyl)-N-isopropylaniline | | 15 | |
| (17) Core1-20 | 4-((1E,3E)-4-(5,6-dimethoxybenzo[d]thiazole-2-yl)buta-1,3-dienyl)-N-(hepta-1,6-diene-4-yl)aniline | | 16 | |
| (18) Core2-9 | N-(5-((1E,3E)-4-(5,6-dimethoxybenzo[d]thiazole-2-yl)buta-1,3-dienyl)pyridine-2-yl)acetamide | | 17 | |

TABLE 1-continued

| Name | Name of Compound | Structural Formula | Synthesis Embodiment | Fluorescence property binding capacity |
|---|---|---|---|---|
| (19) Core2-10 | 3-(5-((1E,3E)-4-(5,6-dimethoxybenzo[d]thiazole-2-yl)buta-1,3-dienyl)pyridine-2-yl amino)propanol-1-ol | | 18 | |
| (20) Core2-14 | N,N-diallyl-5-((1E,3E)-4-(5,6-dimethoxybenzo[d]thiazole-2-yl)buta-1,3-dienyl)pyridine-2-amine | | 19 | |
| F0-PBB3 analog | 1-fluoro-2-(2-((1E,3E)-4-(6-(dimethylamino)pyridine-3-yl)buta-1,3-dienyl)benzo[d]thiazole-6-yloxy)-2-hydroxymethyl-ethane | | 20-1 | |
| (21) F0-PBB3 | 1-fluoro-3-(2-((1E,3E)-4-(6-(methylamino)pyridine-3-yl)buta-1,3-dienyl)benzo[d]thiazole-6-yloxy)propan-2-ol | | 20-2 | |
| (22) F0-PBB3.2 | (E)-1-fluoro-3-(2-(4-(6-(methylamino)pyridine-3-yl)buta-1-en-3-ynyl)benz[d]thiazole-6-yloxy)propan-2-ol | | 21 | |
| (23) F1-PBB3 | 2-((1E,3E)-4-(2-fluoro-6-(methyl amino)pyridine-3-yl)buta-1,3-dienyl)benzo[d]thiazole-6-ol | | 22 | |

TABLE 1-continued

| Name | Name of Compound | Structural Formula | Synthesis Embodiment | Fluorescence property binding capacity |
|---|---|---|---|---|
| (24) Fl-PBB3.2 | (E)-2-(4-(2-fluoro-6-(methylamino)pyridine-3-yl)buta-1-en-3-ynyl)benz[d]thiazole-6-ol | | 23 | |
| (25) Fl-PBBf3 | 2-((1E,3E)-4-(2-fluoro-6-(methylamino)pyridine-3-yl)buta-1,3-dienyl)benzo furan-5-ol | | 24 | |
| (26) Fl-PBB3.2 | (E)-2-(4-(2-fluoro-6-(methylamino)pyridine-3-yl)buta-1-en-3-ynyl)benzofuran-5-ol | | 25 | |
| (27) PBQ3.0 | 2((1E,3E)-4-(6-(dimethylamino)pyridine-3-yl)buta-1,3-dienyl)quinoline-6-ol | | 26 | |
| (28) PBQ3 | 2-((1E,3E)-4-(6-(methylamino)pyridine-3-yl)buta-1,3-dienyl)quinoline-6-ol | | 27 | |
| (29) PBQ3.1 | (E)-2-(4-(6-(dimethylamino)pyridine-3-yl)buta-1-en-3-ynyl)quinoline-6-ol | | 28 | |
| (30) PBQ3.2 | (E)-2-(4-(6-(methylamino)pyridine-3-yl)buta-1-en-3-ynyl)quinoline-6-ol | | 29 | |

In one embodiment, in the specific compounds given above, one or more atoms are a radioisotope of the atom(s). Preferably, a carbon atom on nitrogen bound to a benzene ring or a pyridine ring is the radioisotope $^{11}$C. Preferably, F in the above specific compounds is the radioisotope $^{18}$F. Preferably, a carbon atom of a methoxy group bound to a benzothiazole ring is the radioisotope $^{11}$C. More preferably, an atom with the "*" symbol in the structural formulas of the above specific compounds (where there are two "*" symbols in a structural formula, one or two of them) is the radioisotope of that atom, which is, for example, $^{11}C$ or $^{18}F$. In this description, names such as [$^{11}C$]PBB3 mean that $^{11}C$ is above the atom of the "*" symbol in the structural formula of PBB3, and so on.

3. Methods of Preparing the Compounds of the Present Invention

Synthesis Example 1

The compound of the present invention according to the formula (I) can be prepared according to following scheme 1:

Scheme 1

[Formula 23]

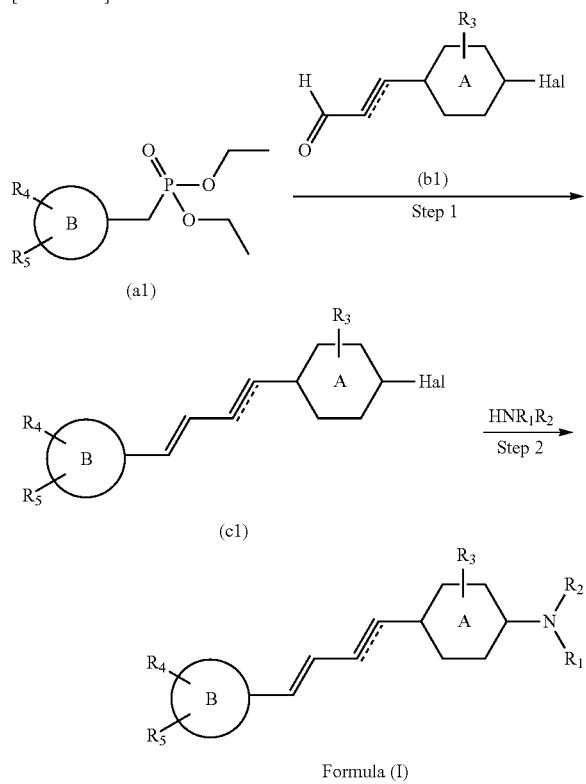

Formula (I)

In the above formulas, A, B, $R_1$ to $R_5$, and

[Formula 24]

have been defined about in the compound of the formula (I), and Hal is halogen, especially bromo.

The method of preparing the compounds of the present invention includes step 2 of reacting the compound (c1) with $NHR_1R_2$ and obtaining the compound of the formula (I). Preferably, the method of preparing the compounds of the present invention includes step 1 of coupling the compound (a1) with the compound (b1) and obtaining the compound (c1), and step 2 of reacting the compound (c1) with $NHR_1R_2$ and obtaining the compound of the formula (I).

The reaction of above step 1 can be performed under Wittig reaction conditions. This reaction can be performed under an inert gas atmosphere such as argon or nitrogen. This reaction preferably uses bases such as sodium hydride, sodium methoxide, or sodium ethoxide. This reaction is preferably performed in an inert solvent such as tetrahydrofuran (THF) or N,N-dimethylformamide (DMF). The temperature of this reaction is not limited, but can be in a range from 0° C. (in an ice bath) to room temperature.

The reaction of above step 2 can be performed under electrophilic aromatic substitution conditions. This reaction can be performed using bases such as triethylamine. This reaction is preferably performed in an inert solvent such as DMF, or in an alcohol solvent such as methanol or ethanol. The temperature of this reaction is not limited and ranges from 0° C. (in an ice bath) to reflux temperature, and can be, for example, 0° C. to 160° C., 30° C. to 150° C., 60° C. to 140° C., 90° C. to 130° C., or 120° C.

If necessary, it is possible to protect each compound with a protecting group prior to the reactions of above step 1 and/or step 2, and then perform the reactions. When one or more of $R_1$ to $R_5$ have a hydroxy or an amino group, it is preferable to protect this hydroxy or amino group with an adequate protecting group. Examples of protecting groups for hydroxy or amino groups include alkyl groups such as methyl groups and ethyl groups, benzyl groups, t-butyldimethylsilyl groups (—Si(CH$_3$)$_2$(t-C$_4$H$_9$)), tert-butoxycarbonyl groups (Boc: —COO-(t-C$_4$H$_9$)), methoxymethyl groups (—CH$_2$OCH$_3$), and ethoxymethyl groups (—CH$_2$OCH$_2$CH$_3$). Deprotection may be performed in adequate steps, in a method that is known to one of skill in the art.

Synthesis Example 2

The compound of the present invention according to the formula (I), in which $R_1$ and $R_2$ are hydrogen, may be prepared in accordance with following scheme 2:

Scheme 2

[Formula 25]

-continued

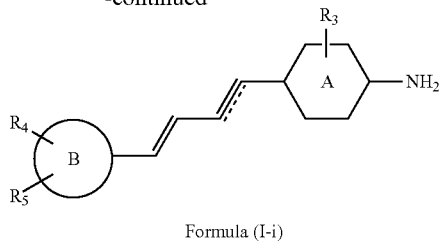

Formula (I-i)

In the above formulas, A, B, $R_3$ to $R_5$, and

[Formula 26]

$$\equiv\equiv\equiv$$

have been defined above in the compound of the formula (I).

The method of preparing the compounds of the present invention includes step 2 of reducing the compound (c2) and obtaining the compound of the formula (I-i) (the compound of the formula (I), in which $R_1$ and $R_2$=H). Also, prior to step 2, the method of preparing the compounds of the present invention further includes step 1 of coupling the compound (a2) with the compound (b2) and obtaining the compound (c2).

The reaction of above step 1 can be performed under Wittig reaction conditions. This reaction can be performed under an inert gas atmosphere such as argon or nitrogen. This reaction preferably uses bases such as sodium hydride, sodium methoxide, or sodium ethoxide. This reaction is preferably performed in an inert solvent such as tetrahydrofuran (THF) or N,N-dimethylformamide (DMF). The temperature of this reaction is not limited and might range from 0° C. (in an ice bath) to room temperature.

The reduction in above step 2 can be performed under reducing conditions to convert an aromatic nitro group into an amino group. For example, this reduction can be performed using iron, zinc, or tin chloride in an acid solution. For the acid solution, acetic acid, hydrochloric acid, or a liquid mixture of these may be used. Furthermore, salts such as ammonium chloride may be used. This reduction c can be performed in an alcohol solution such as methanol, ethanol or propanol. This reduction can be performed in, but is by no means limited to, room temperature to reflux temperature. For example, this reduction can be performed at 20° C. to 100° C., 40° C. to 90° C., or 80° C. Also, this reduction can be performed in catalytic hydrogenation using a metal catalyst such as platinum, or can be performed in reduction using a metal hydride such as lithium aluminum hydride.

If necessary, it is possible to protect each compound with an adequate protecting group prior to the reactions of above step 1 and/or step 2, and then perform the reactions. When one or more of $R_3$ to $R_5$ have a hydroxy or an amino group, it is preferable to protect that hydroxy or amino group with an adequate protecting group. Examples of protecting groups for hydroxy or amino groups include alkyl groups such as methyl groups or ethyl groups, benzyl groups, t-butyldimethylsilyl groups (—Si(CH$_3$)$_2$(t-C$_4$H$_9$)), tert-butoxycarbonyl groups (Boc: —COO-(t-C$_4$H$_9$)), methoxymethyl groups (—CH$_2$OCH$_2$CH$_3$), and ethoxymethyl groups (—CH$_2$OCH$_2$CH$_3$). Deprotection may be performed in adequate steps, in a method that is known to one of skill in the art.

Synthesis Example 3

The compound of the present invention according to the formula (I), in which $R_1$ is not hydrogen and $R_2$ is hydrogen, can be prepared according to following scheme 3:

Scheme 3

[Formula 27]

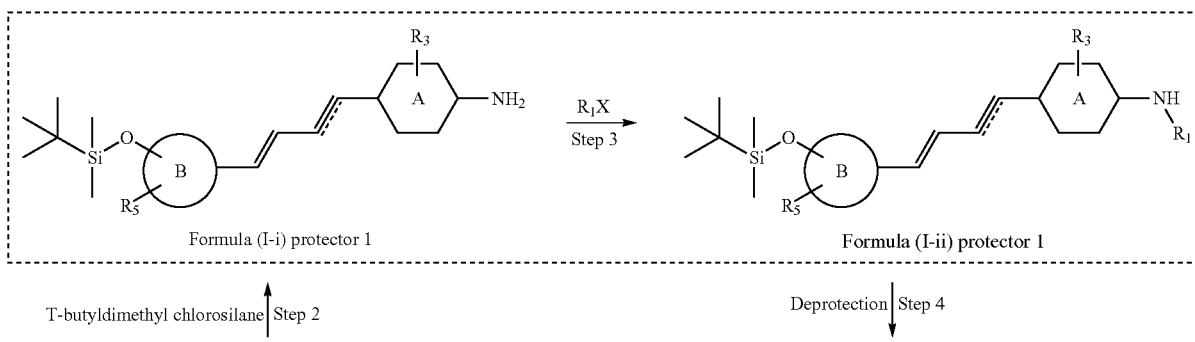

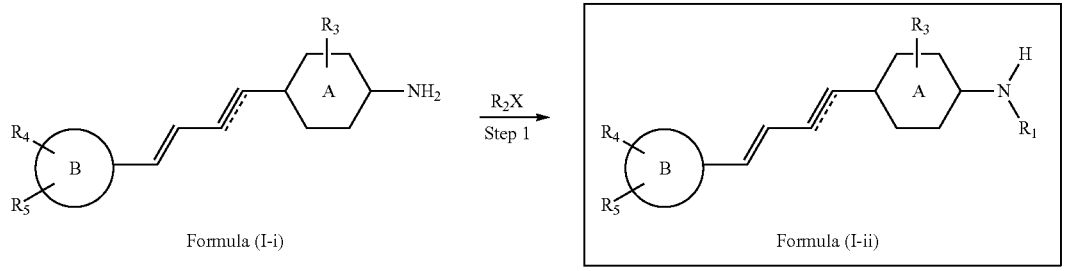

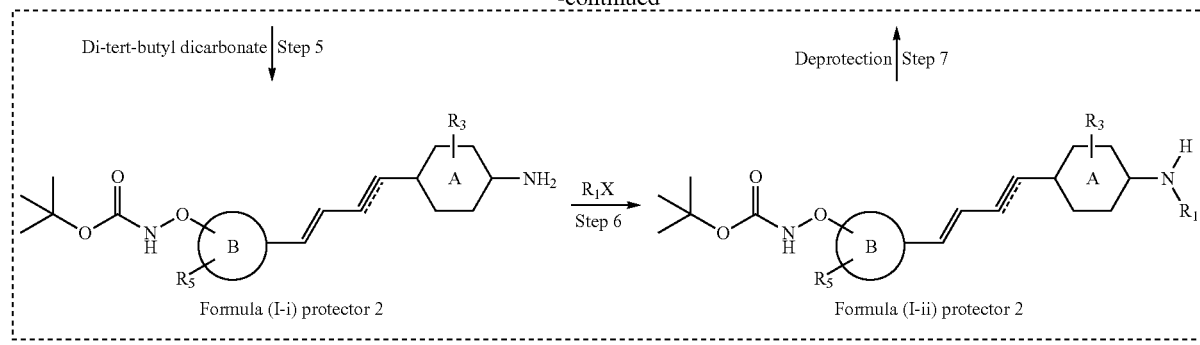

Formula (I-i) protector 2    Formula (I-ii) protector 2

In the above formulas, A, B, $R_1$, $R_3$ to $R_5$, and

[Formula 28]

$$\overline{\overline{\phantom{xxx}}}$$

have been defined above in the compound of the formula (I), where, however, $R_1$ is not hydrogen, X is an elimination group and is, for example, halogen such as Cl, Br or I, alkoxy such as methoxy or ethoxy, triflate (—$OSO_2$—$CF_3$), carboxylate (—OCO—R), or an azide group (—$N_3$).

In scheme 3, the compound of the formula (I-i) which is the starting substance, can be synthesized according to above scheme 2. With the method of preparing the compounds of the present invention, it is possible to include step 1 of obtaining the compound of the formula (the compound of the formula (I), in which $R_1 \neq H$ and $R_2 = H$) by reacting the compound of the formula (I-i) with $R_1X$ with reference to above scheme 3.

The reaction of above step 1 is alkylation, alkenylation, acylation or hydroxyalkylation of an amino group. When $R_1$ is alkyl, alkenyl, hydroxyalkyl and/or the like, this reaction can be performed under nucleophilic substitution reaction conditions. In this case, X is preferably halogen, especially Cl, Br or I, or triflate (—$OSO_2$—$CF_3$). This reaction may use a base such as $K_2CO_3$ or triethylamine, or may use a reducing agent such as sodium hydride or sodium borohydride. This reaction may be performed under an inert atmosphere such as nitrogen or argon. This reaction may be performed in an inert solvent such as dichloromethane, chloroform, or N,N-dimethylformamide, or in an alcohol solvent such as methanol or ethanol. This reaction can be performed at, but is not limited to, 0° C. (in an ice bath) to room temperature, or at room temperature to reflux temperature, which can be, for example, 0° C. to 160° C., 30° C. to 150° C., 60° C. to 140° C., 90° C. to 130° C., or 120° C.

In the reaction of above step 1, when $R_1$ is methyl in the formula (I-ii), a different method, in which the compound of the formula (I-i) is reacted with formaldehyde or paraformaldehyde, and, after that, the product is reduced using a reducing agent such as sodium hydride or sodium borohydride, may be used.

The reaction of above step 1 can be performed under nucleophilic acyl substitution reaction conditions when $R_1$ is acyl and/or the like. In this case, X is preferably halogen such as Cl, Br or I, alkoxy such as methoxy or ethoxy, carboxylate (—OCO—R), or an azide group (-$N_3$). This reaction can be performed in the presence of bases such as $K_2CO_3$ or triethylamine. This reaction may be performed under acid conditions such as HCl. This reaction can be performed in an inert solvent such as dichloromethane, chloroform or N,N-dimethylformamide. This reaction can be performed at, but is by no means limited to, 0° C. (in an ice bath) to reflux temperature.

If necessary, it is possible to protect each compound with an adequate protecting group prior to the reaction of above step 1, and then perform the reaction. When one or more of $R_1$, $R_3$ to $R_5$ have a hydroxy or an amino group, it is preferable to protect that hydroxy or amino group with an adequate protecting group. Examples of protecting groups for hydroxy or amino groups include alkyl groups such as methyl groups and ethyl groups, benzyl groups, t-butyldimethylsilyl groups (—$Si(CH_3)_2(t-C_4H_9)$), tert-butoxycarbonyl groups (Boc:—COO-(t-$C_4H_9$)), methoxymethyl groups (—$CH_2OCH_3$), and ethoxymethyl groups (—$CH_2OCH_2CH_3$). Deprotection may be performed in a method that is known to one of skill in the art.

For example, when one or both of $R_4$ and $R_5$ are OH, as shown in steps 2 to 4 of scheme 3, it is possible to synthesize protector 1 of the formula (I-i) from the compound of the formula (I-i), react it with $R_1X$, and, after that, synthesize the compound of the formula (I-ii) by deprotection. Step 2 shown in scheme 3 is a step for when $R_4$ alone is OH. One of skill in the art should readily understand that the protector can be synthesized when $R_5$ alone is OH or when $R_4$ and $R_5$ are both OH. This protector can be obtained by reacting the compound of the formula (I-i) with t-butyldimethylchlorosilane. This reaction may use a base such as imidazole. This reaction is preferably performed under an inert gas atmosphere such as nitrogen or argon. Also, this reaction is usually performed under an inert solvent such as dimethylsulfoxide. The temperature of this reaction is preferably room temperature.

After formula (I-i) protector 1 is prepared, a formula (I-ii) protector can be prepared by a reaction with $R_1X$ (step 3). This reaction may adopt the same reaction conditions as in step 1 above. After that, by deprotecting the formula (I-ii) protector, the compound of the formula (I-ii), in which one or both of $R_4$ and $R_5$ are OH, can be obtained. This deprotection can be performed using acid such as hydrochloric acid or using fluoride ion such as tetra-n-butylammonium fluoride hydrate.

Also, for example, when one or both of $R_4$ and $R_5$ are aminoalkyl, as shown in steps 5 to 7 of scheme 3, it is possible to synthesize formula (I-i) protector 2 from the compound of the formula (I-i), react it with $R_1X$, and, after that, synthesize the compound of the formula (I-ii) by deprotection. Step 5 shown in scheme 3 is a step for when $R_4$ alone is aminoalkyl. One of skill in the art should readily understand that the protector can be synthesized when $R_5$ alone is aminoalkyl, as well as when $R_4$ and $R_5$ are both aminoalkyl. This protector can be obtained by reacting the compound of the formula (I-i) with tert-butyldicarbonate.

In scheme 3, when $R_1X$ is [$^{11}$C]alkyl-X such as $^{11}CH_3$—X, [$^{11}$C]alkyl such as $-^{11}CH_3$ can be introduced.

Synthesis Example 4

The compound of the present invention according to the formula (I) in which $R_1$ is not hydrogen and $R_2$ is hydrogen, may be prepared according to following scheme 4.

Scheme 4

[Formula 29]

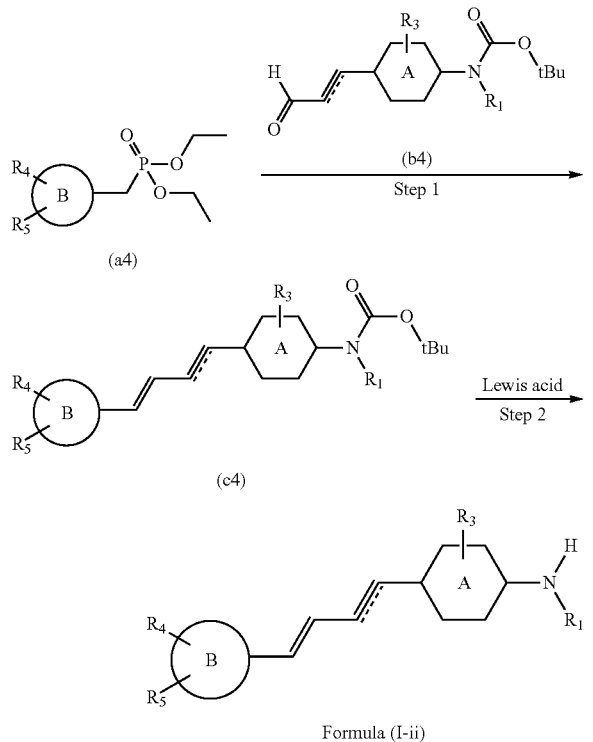

In the above formulas, A, B, $R_1$, $R_3$ to $R_5$, and have been defined above in the compound of the formula (I), in which, however, $R_1$ is not hydrogen.

The method of preparing the compounds of the present invention includes step 2 of reacting the compound (c4) with Lewis acid and obtaining the compound of the formula (I-ii) (the compound of the formula (I), in which $R_1 \neq H$ and $R_2 = H$). Furthermore, step 3 of obtaining the compound of the formula (I-iii) (the compound of the formula (I), in which $R_1$ and $R_2 \neq H$) by a reaction with $R_2X$ after reduction, may be included. Also, the method of preparing the compounds of the present invention may further include, prior to step 2, step 1 of coupling the compound (a4) with the compound (b4) and obtaining the compound (c4).

The reaction of above step 1 can be performed under Wittig reaction conditions. This reaction can be performed under an inert gas atmosphere such as argon or nitrogen. This reaction preferably uses a base such as sodium hydride, sodium methoxide, or sodium ethoxide. This reaction is preferably performed in an inert solvent such as tetrahydrofuran (THF) or N,N-dimethylformamide (DMF). The temperature of this reaction is not limited, but can be in a range from 0° C. (in an ice bath) to room temperature.

The reaction of above step 2 is performed under Boc (tert-butoxycarbonyl group) deprotection conditions. Lewis acid is preferably $BB_{r3}$. This reaction can be performed under an inert gas atmosphere such as argon or nitrogen. This reaction can be performed in an inert solvent such as dichloromethane or chloroform. The temperature of this reaction can be made room temperature.

If necessary, it is possible to protect each compound with an adequate protecting group prior to the reactions of above step 1 and/or step 2, and then perform the reactions. When one or more of $R_1$, $R_3$ to $R_5$ have a hydroxy or an amino group, it is preferable to protect that hydroxy or amino group with an adequate protecting group. Examples of protecting groups for hydroxy or amino groups include alkyl groups such as methyl groups and ethyl groups, benzyl groups, t-butyldimethylsilyl groups (—Si(CH$_3$)$_2$(t-C$_4$H$_9$)), tert-butoxycarbonyl groups (Boc: —COO-(t-C$_4$H$_9$)), methoxymethyl groups (—CH$_2$OCH$_3$), and ethoxymethyl groups (—CH$_2$OCH$_2$CH$_3$). Deprotection may be performed in adequate steps, in a method that is known to one of skill in the art.

Synthesis Example 5

The compound of the present invention according to the formula (I), in which $R_1$ and $R_2$ are not hydrogen, can be prepared according to following scheme 5.

Scheme 5

[Formula 31]

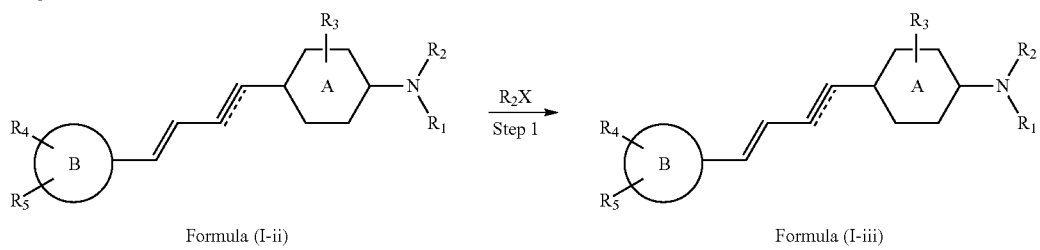

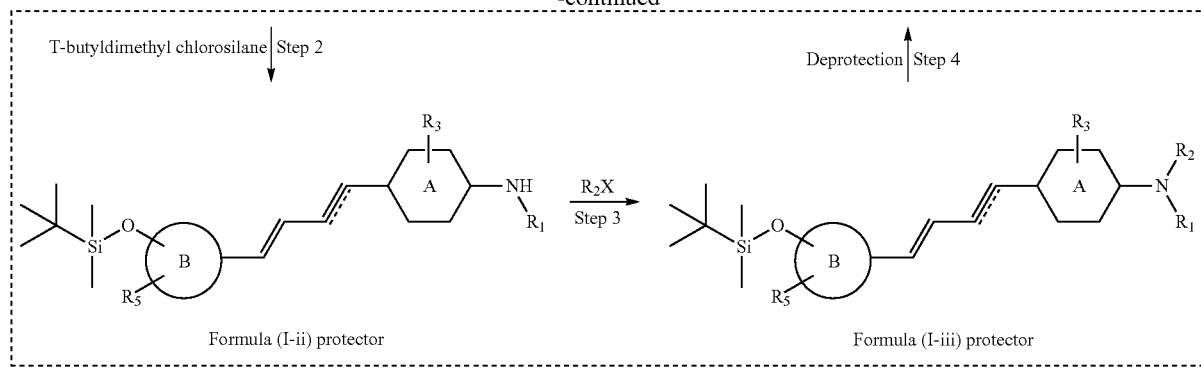

Formula (I-ii) protector → Formula (I-iii) protector

In the above formulas, A, B, $R_1$ to $R_5$, and

[Formula 32]

$$\equiv$$

have been defined above in the compound of the formula (I), in which, however, $R_1$ and $R_2$ are not hydrogen, X is an elimination group, which is, for example, halogen such as Cl, Br or I, alkoxy such as methoxy or ethoxy, triflate (—OSO$_2$—CF$_3$), carboxylate (—OCO—R), or an azide group (—N$_3$).

The compound of the formula (I-ii), which is the starting substance, can be synthesized in accordance with above scheme 3 or 4. With the method of preparing the compounds of the present invention, it is possible to include step 1 of obtaining the compound of the formula (I-iii) (the compound of the formula (I), in which $R_1$ and $R_2 \neq H$) by reacting the compound of the formula (I-ii) with $R_2X$ with reference to above scheme 5. When $R_1$ and $R_2$ are the same group, it is possible to synthesize the compound of the formula (I-iii) directly from the compound of the formula (I-i), in above scheme 3 or 4.

Similar to the reaction in step 1 of scheme 3 above, the reaction in step 1 of scheme 5 is alkylation, alkenylation, acylation or hydroxyalkylation of an amino group. Step 1 of scheme 5 can be performed under the same conditions as for step 1 of above scheme 3.

If necessary, it is possible to protect each compound with an adequate protecting group prior to the reaction of above step 1, and then perform the reaction. When one of more of $R_1$ to $R_5$ have a hydroxy or an amino group, it is preferable to protect that hydroxy or amino group with an adequate protecting group. Examples of protecting groups for hydroxy or amino group include alkyl groups such as methyl groups and ethyl groups, benzyl groups, t-butyldimethylsilyl groups (—Si(CH$_3$)$_2$(t-C$_4$H$_9$)), tert-butoxycarbonyl groups (Boc:—COO-(t-C$_4$H$_9$)), methoxymethyl groups (—CH$_2$OCH$_3$), and ethoxymethyl groups (—CH$_2$OCH$_2$CH$_3$). Deprotection may be performed in a method that is known to one of skill in the art.

For example, when one or both of R4 and R5 are OH, the formula (I-ii) protector may be prepared as shown in step 2 of scheme 5. Step 2 shown in scheme 5 is a step for when $R_4$ alone is OH. This protector can be obtained by reacting the compound of the formula (I-ii) with t-butyldimethyl-chlorosilane. This reaction may use a base such as imidazole. This reaction is preferably performed under an inert gas atmosphere such as nitrogen or argon. Also, this reaction is usually performed under an inert solvent such as dimethylsulfoxide. The temperature of this reaction is preferably room temperature. One of skill in the art should readily understand that protector can be synthesized when $R_4$ is not OH and $R_5$ is OH, as well as when $R_4$ and $R_5$ are OH.

After the formula (I-ii) protector is prepared, it is possible to prepare the formula (I-iii) protector by a reaction with $R_2X$, (Step 3). This reaction may adopt the same reaction conditions as in step 1 above. After that, by deprotecting the formula (I-ii) protector, the compound of the formula (I-iii), in which one or both of R4 and R5 are OH, can be obtained. This deprotection can be performed using acid such as hydrochloric acid, or fluoride ion.

In above step 1, when $R_2X$ is [$^{11}$C]alkyl-X such as $^{11}$CH$_3$—X, a radioisotope for [$^{11}$C] alkyl, such as —$^{11}$CH$_3$, can be introduced.

Synthesis Example 6

The compound of the present invention according to the formula (I), in which $R_3$ is halogen, can be prepared according to following scheme 6:

Scheme 6

[Formula 33]

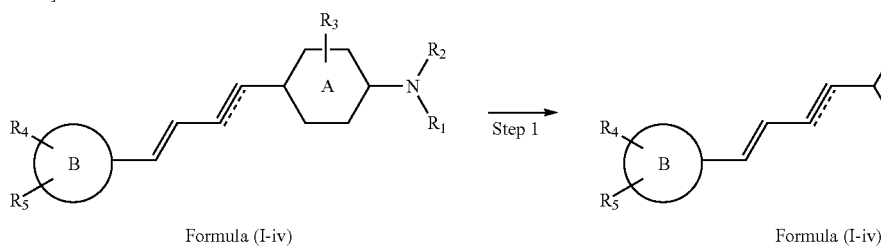

Formula (I-iv) → Formula (I-iv)

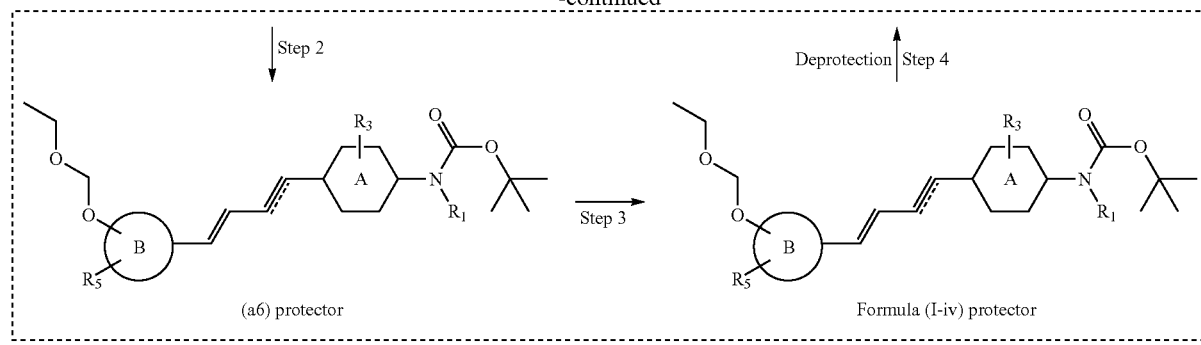

In the above formulas, A, B, $R_1$ to $H_5$, and

[Formula 34]

$$\equiv\equiv\equiv$$

have been defined above in the compound of the formula (I), in which, however, $R_3$ is halogen, especially F. With the method of scheme 6, a radioisotope for $^{18}$F can be introduced.

If necessary, it is possible to protect each compound with an adequate protecting group prior to the reaction of above step 1, and then perform the reaction. When one or more of $R_1$ to $R_5$ have a hydroxy or an amino group, it is preferable to protect that hydroxy or amino group with an adequate protecting group. Examples of protecting groups for hydroxy or amino groups include alkyl groups such as methyl groups and ethyl groups, benzyl groups, t-butyldimethylsilyl groups (—Si(CH$_3$)$_2$(t-C$_4$H$_9$)), tert-butoxycarbonyl groups (Boc:—COO-(t-C$_4$H$_9$)), methoxymethyl groups (—CH$_2$OCH$_3$), and ethoxymethyl groups (—CH$_2$OCH$_2$CH$_3$). Deprotection may be performed in a method that is known to one of skill in the art.

For example, when, as shown in step 2, one or both of $R_1$ and $R_2$ are hydrogen, it is preferable to protect with a protecting group such as a tert-butoxycarbonyl group (Boc:—COO-(t-C$_4$H$_9$)), prior to the reaction of step 1. Also, when one or both of $R_4$ and $R_5$ are OH, it is preferable to protect with an ethoxymethyl group (—CH$_2$OCH$_2$CH$_3$), prior to the reaction of step 1.

Synthesis Example 7

The compound of the present invention according to the formula (I), in which $R_4$ is alkoxy, may be prepared according to following scheme 7.

Scheme 7

[Formula 35]

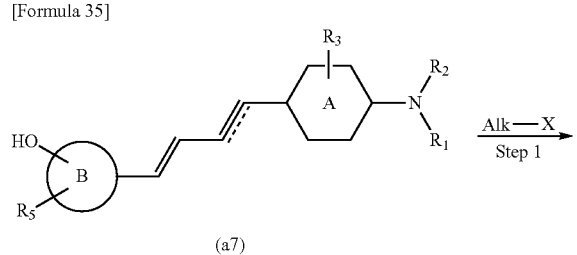

-continued

Formula (I-v)

In the above formulas, A, B, $R_1$ to $R_3$, $R_5$, and

[Formula 36]

$$\equiv\equiv\equiv$$

have been defined above in the compound of the formula (I), in which Alk means alkyl and X means an elimination group.

With reference to above scheme 7, the method of preparing the compounds of the present invention can include step 1 of obtaining the compound of the formula (I-v) (the compound of the formula (I), in which $R_4$ is methoxy), by reacting the compound (a7) with Alk-X.

If necessary, it is possible to protect each compound with an adequate protecting group prior to the reaction of above step 1, and then perform the reaction. When one or more of $R_1$ to $R_3$, and $R_5$ have a hydroxy or an amino group, it is preferable to protect this hydroxy or amino group with an adequate protecting group. Examples of protecting groups for hydroxy or amino groups include alkyl groups such as methyl groups and ethyl groups, benzyl groups, t-butyldimethylsilyl groups (—Si(CH$_3$)$_2$(t-C$_4$H$_9$)), tert-butoxycarbonyl groups (Boc: —COO-(t-C$_4$H$_9$)), methoxymethyl groups (—CH$_2$OCH$_3$), and ethoxymethyl groups (—CH$_2$OCH$_2$CH$_3$). Deprotection may be performed in a method that is known to one of skill in the art.

When Alk-X is [$^{11}$C]alkyl-X such as $^{11}$CH$_3$—X, a radioisotope for [$^{11}$C]alkyl, such as —$^{11}$CH$_3$, can be introduced.

Synthesis Example 8

The compound of the present invention according to the formula (I), in which $R_4$ is halohydroxyalkoxy, may be prepared according to following scheme 8.

Scheme 8

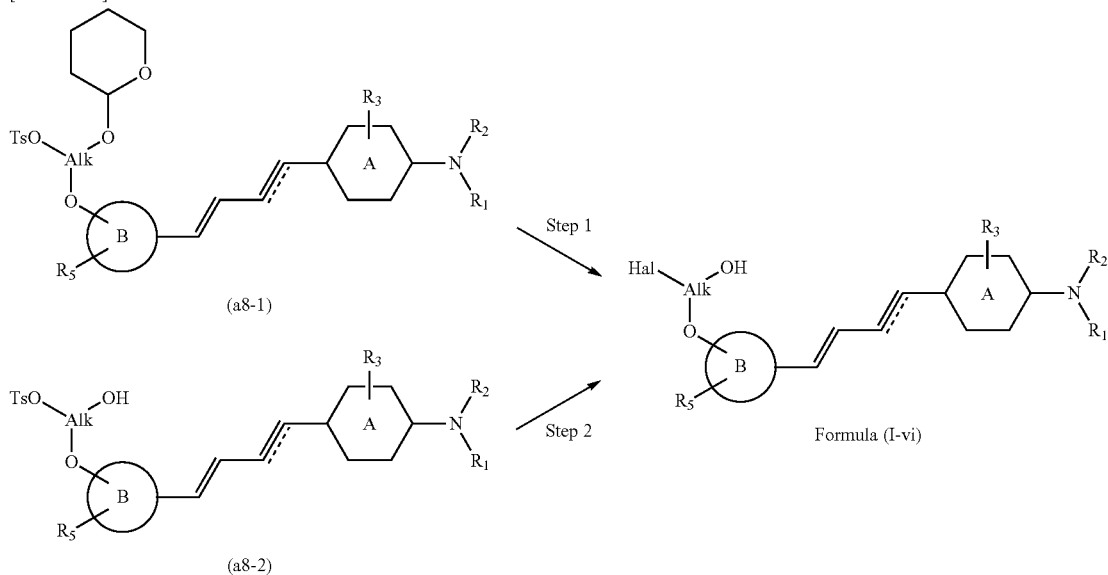

In the above formulas, A, B, $R_1$ to $R_3$, $R_5$, and

 [Formula 38]

have been defined above in the compound of the formula (I), in which Alk means an alkyl group, TsO means tosylate (p-$H_3C$—$C_6H_4$—$SO_2$—O—), and Hal means halogen, especially F.

With reference to above scheme 8, the method of preparing the compounds of the present invention can include step 1 of obtaining the compound of the formula (I-v) (the compound of the formula (I), in which $R_4$ is methoxy) by reacting the compound (a8-1) or (a8-2).

In the above compounds (a8-1) and (a8-2),

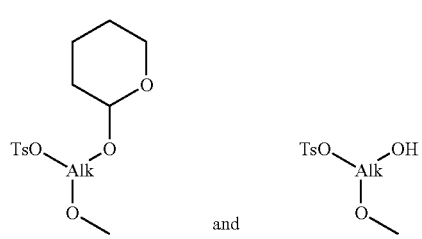 [Formula 39]

mean, respectively, a group in which TsO- and —O-2-tetrahydropyranyl are bound to given positions of the carbon atoms of —O-alkyl (alkoxy), and a group in which TsO- and OH are bound to given positions of the carbon atoms of —O-alkyl (alkoxy). For example, the above formulas mean —O—$CH_2$CH (—O-2-tetrahydropyranyl) (—$CH_2$—OTs) or —O—$CH_2$CH (—OH) (—$CH_2$-OTs), and —O—CH (—O-2-tetrahydropyranyl) (—$CH_2$—OTs) or —O—CH (—$CH_2$—OH) (—$CH_2$-OTs), and so on.

Similarly, in the above formulas,

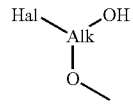 [Formula 40]

means a group in which Hal and OH are bound to given positions of the carbon atoms of —O-alkyl(alkoxy), that is, halohydroxyalkoxy.

Synthesis Example 9

The compound of the present invention according to the formula (I), in which $\equiv$ is a triple bond, may be prepared according to following scheme 9.

Scheme 9

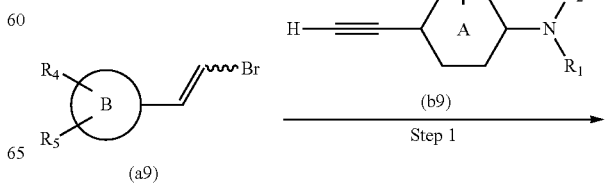

-continued

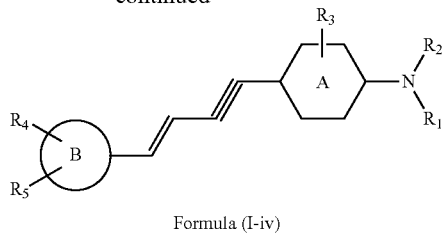

Formula (I-iv)

In the above formulas, A, B, and $R_1$ to $R_5$ have been defined above with the compound of the formula (I).

With reference to above scheme 9, the method of preparing the compounds of the present invention can include step 1 of obtaining the compound of the formula (I-vi) (the compound of the formula (I), in which $$\equiv$$

is a triple bond) by coupling the compound (a9) with the compound (b9).

The reaction of above step 1 is performed under Sonogashira reaction conditions. This reaction can be performed using a copper catalyst such as cuprous iodide, a palladium catalyst such as dichlorobis (triphenylphosphine) palladium, and a base such as triethylamine. The temperature of this reaction may be 25° C. to 120° C., preferably 50° to 100°, and most preferably 70°.

If necessary, it is possible to protect each compound with an adequate protecting group prior to the reaction of above step 1, and then perform the reaction. When one or more of $R_1$ to $R_5$ have a hydroxy or an amino group, it is preferable to protect that hydroxy or amino group with an adequate protecting group. Examples of protecting groups for hydroxy or amino groups include alkyl groups such as methyl groups and ethyl groups, benzyl groups, t-butyldimethylsilyl groups (—Si(CH$_3$)$_2$(t-C$_4$H$_9$)), tert-butoxycarbonyl groups (Boc: —COO-(t-C$_4$H$_9$)), methoxymethyl groups (—CH$_2$OCH$_3$), and ethoxymethyl groups (—CH$_2$OCH$_2$CH$_3$). Deprotection may be performed in a method that is known to one of skill in the art.

4. Intermediates

The present invention provides an intermediate for synthesizing the compound of the present invention according to the formula (I). Preferably, the intermediate is selected from the group consisting of the following:

the formula (I-i) in above scheme 2 (in the formula, $R_4$ is hydroxy);

the formula (I-ii), the formula (I-i) protector 1, and the formula (I-i) protector 2 in above scheme 3;

the formula (I-ii) protector in above scheme 5;

(a6) and the (a6) protector in above scheme 6;

the (a7) protector in above scheme 7; and (a8-1) and (a8-2) in above scheme 8.

In one embodiment, the present invention provides an intermediate for synthesizing the compound of the present invention according to the formula (I), selected from the group consisting of the following:

TABLE 2

| Name | Name of Compound | Structural Formula | Synthesis Embodiment |
|---|---|---|---|
| (pre2) | Synthetic intermediate of PBB2 | 2-((1E,3E)-4-(4-aminophenyl)buta-1,3-dienyl)benzo[d]thiazole-6-ol | 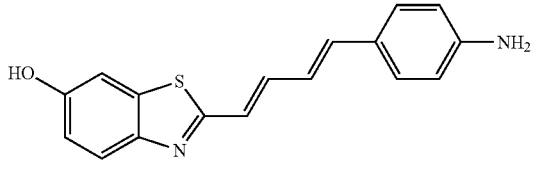 [SMILES: Nc1ccc(/C=C/C=C/c2nc3ccc(O)cc3s2)cc1] | 30 |
| (pre3) | Synthetic intermediate of PBB3 | 5-((1E,3E)-4-(6-(tert-butyl-dimethylsilyloxy)benz[d]thiazole-2-yl)buta-1,3-dienyl)pyridine-2-amine | 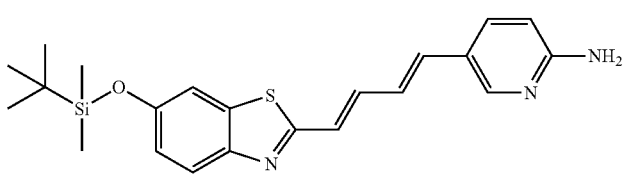 | 31 |
| (pre6) | Synthetic intermediate of mPBB5 | 2-((1E,3E)-4-(4-(dimethylamino)phenyl)buta-1,3-dienyl)-3-ethyl-6-hydroxy-benzo[d]thiazole-3-ium | 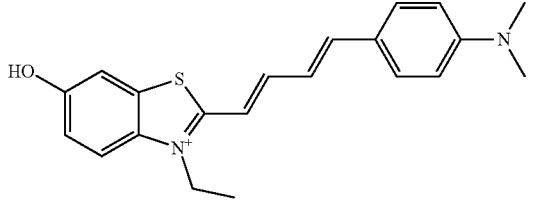 [SMILES: CC[n+]1c(/C=C/C=C/c2ccc(N(C)C)cc2)sc2cc(O)ccc21] | 32 |

TABLE 2-continued

| Name | Name of Compound | Structural Formula | Synthesis Embodiment |
|---|---|---|---|
| (pre7) | Synthetic intermediate of PBB2.1 | (E)-2-(4-(4-(methylamino)phenyl)buta-1-en-3-ynyl)benz[d]thiazole-6-ol 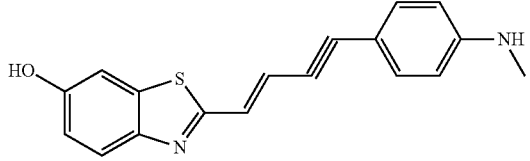 | 7 |
| (pre8) | Synthetic intermediate of PBB2.2 | (E)-2-(4-(4-aminophenyl)buta-1-en-3-ynyl)benz[d]thiazole-6-ol 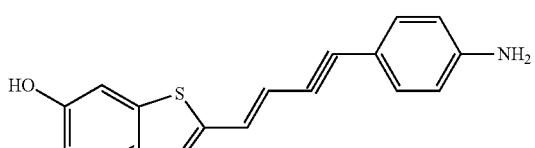 | 8 |
| (pre11) | Synthetic intermediate of PBB3.2 | (E)-5-(4-(6-(tert-butyldimethylsilyloxy)benz[d]thiazole-2-yl)buta-3-en-1-ynyl)pyridine-2-amine 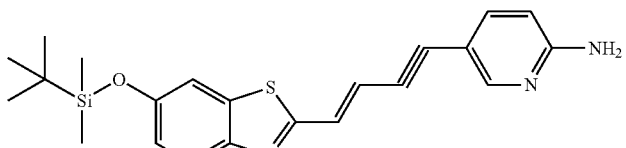 | 34 |
| (pre12) | Synthetic intermediate of PBB3.2N | (E)-tert-butyl(2-(4-(6-aminopyridine-3-yl)buta-1-en-3-ynyl)benz[d]thiazole-6-yl)methylcarbamate 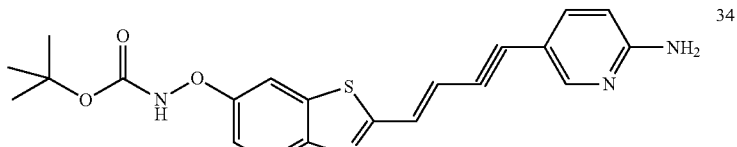 | 34 |
|  | Synthetic intermediate of F0-PBB3 analog | 2-(2-((1E,3E)-4-(6-(dimethylamino)pyridine-3-yl)buta-1,3-dienyl)benzo[d]thiazole-6-yloxy)-2-hydroxymethylethyl 4-methylbenzenesulfonate 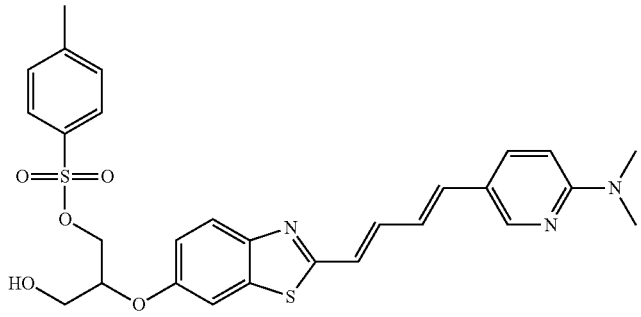 [SMILES: Cc1ccc(S(=O)(=O)OCC(CO)Oc2ccc3nc(/C=C/C=C/c4ccc(N(C)C)nc4)sc3c2)cc1] | 35-1 |
| (pre21) | Synthetic intermediate of F0-PBB3 | 3-(2-((1E,3E)-4-(6-(methylamino)pyridine-3-yl)buta-1,3-dienyl)benzo[d]thiazole-6-yloxy)-2-(tetrahydro-2H-pyran-2-yloxy)propyl 4-methylbenzenesulfonate 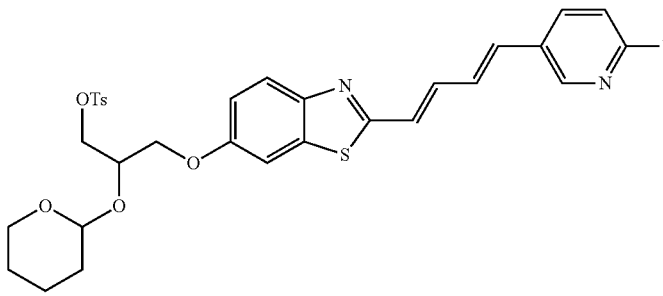 | 35-2 |

TABLE 2-continued

| Name | Name of Compound | Structural Formula | Synthesis Embodiment |
|---|---|---|---|
| (pre22) | Synthetic intermediate of F0-PBB3.2 | (E)-3-(2-(4-(6-(methyl amino)pyridine-3-yl)buta-1-en-3-ynyl)benzo[d]thiazole-6-yloxy)-2-(tetrahydro-2H-pyran-2-yloxy)propyl 4-methylbenzenesulfonate | 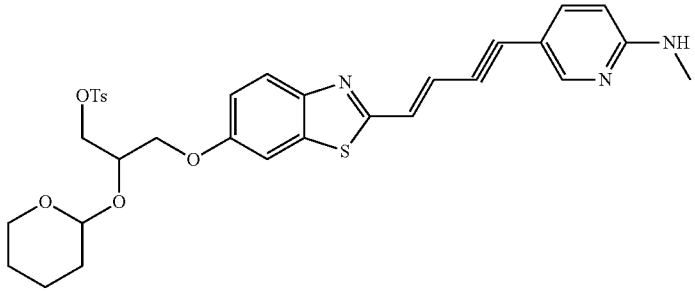 [SMILES: CNc1ccc(C#C/C=C/c2nc3ccc(OCC(COS(=O)(=O)c4ccc(C)cc4)OC4CCCCO4)cc3s2)cn1] | 36 |
| (pre23) | Synthetic intermediate of F1-PBB3 | Tert-butyl 5-((1E,3E)-4-(6-(ethoxymethoxy)benz[d]thiazole-2-yl)buta-1,3-dienyl)-6-nitropyridine-2-yl(methyl)carbamate | 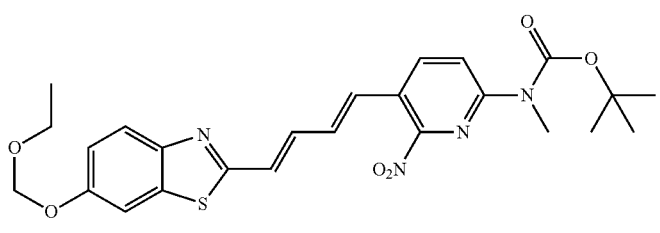 [SMILES: CCOCOc1ccc2nc(/C=C/C=C/c3ccc(N(C)C(=O)OC(C)(C)C)nc3[N+](=O)[O-])sc2c1] | 37 |
| (pre24) | Synthetic intermediate of F1-PBB3.2 | (E)-tert-butyl 5-(4-(6-(ethoxymethoxy)benz[d]thiazole-2-yl)buta-3-en-1-ynyl)-6-nitropyridine-2-yl(methyl)carbamate | 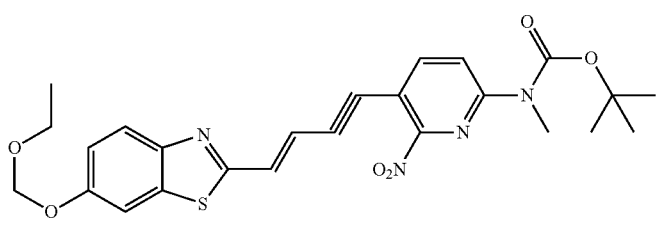 [SMILES: CCOCOc1ccc2nc(/C=C/C#Cc3ccc(N(C)C(=O)OC(C)(C)C)nc3[N+](=O)[O-])sc2c1] | 38 |
| (pre25) | Synthetic intermediate of F1-PBBf3 | Tert-butyl 5-((1E,3E)-4-(5-(ethoxymethoxy)benzofuran-2-yl)buta-1,3-dienyl)-6-nitropyridine-2-yl(methyl)carbamate | 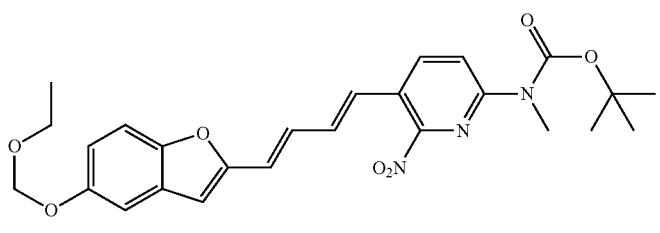 [SMILES: CCOCOc1ccc2oc(/C=C/C#Cc3ccc(N(C)C(=O)OC(C)(C)C)nc3[N+](=O)[O-])cc2c1] | 39 |
| (pre26) | Synthetic intermediate of F1-PBBf3.2 | (E)-tert-butyl 5-(4-(5-(ethoxymethoxy)benzofuran-2-yl)buta-3-en-1-ynyl)-6-nitropyridine-2-yl(methyl)carbamate | 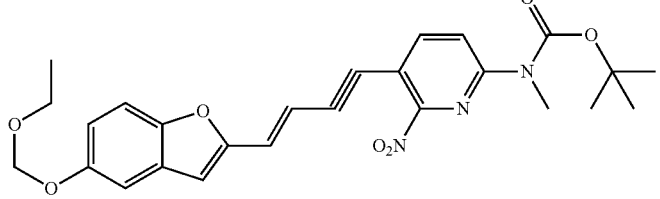 | 40 |

Preferably, the intermediate of the present invention is used to synthesize the compound of the present invention according to the formula (I) labeled with a radioisotope.

5. Compositions

The present invention provides a composition for tau imaging, which contains the compound of the formula (I), or a pharmaceutically acceptable salt thereof or a solvate thereof. Also, this imaging includes in vitro, ex vivo and in vivo imaging. The composition may include a pharmaceutically acceptable carrier. Examples of this pharmaceutically acceptable carrier include water, saline water, physiological saline water or phosphate buffered saline water (PBS), sodium chloride injection solution, Ringer's injection solution, isotonic dextrose injection solution, sterile water injection solution, dextrose, and lactated Ringer's injection solution.

The contents of the compound of the formula (I) and the pharmaceutically acceptable carrier are not particularly limited, and these are determined based on various factors such as: the type of the compound that is used: the age, weight, health conditions, sex, and content of diet of the mammals that receive an administration; the number of administration and the route of administration; the period of treatment; other medicines that are at the same time, and so on. The content of the pharmaceutically acceptable carrier may be made an amount of 1 to 99 weight % of the composition of the present invention. The composition of the present invention may preferably be adjusted such that the compound of the formula (I) can be administered in an amount of 0.01 mg/kg to 5 mg/kg, or 0.05 mg/kg to 3 mg/kg, and preferably 0.1 mg/kg to 1 mg/kg.

6. Methods of Use of the Compounds of the Present Invention

The compounds of the present invention can be used as a molecular probe for tau imaging, that is, as a molecular probe for imaging tau proteins that accumulate in the brains of mammals. Consequently, the present invention provides a tau imaging method that includes administering the compound of the formula (I), or a pharmaceutically acceptable salt or a solvate thereof, to mammals. In another embodiment, the present invention provides a tau imaging method that includes (a) a step of administering an effective dose of the compound of the formula (I), or a pharmaceutically acceptable salt or a solvate thereof, to a mammal, and (b) a step of imaging the brain of the mammal.

The mammal may be, for example, a human, rat, mouse, rabbit, guinea pig, hamster, monkey, dog, ferret or miniature swine. Preferably, the mammal is a human. The method of administration is not particularly limited, and, for example, parenteral administration, intravenous administration, or intraperitoneal administration may be used. Preferably, intravenous administration or intraperitoneal administration may be used. Most preferably, intravenous administration may be used. The amount of administration is preferably 0.01 mg/kg to 5 mg/kg, 0.05 mg/kg to 3 mg/kg, or 0.1 mg/kg to 1 mg/kg, and most preferably 0.1 mg/kg to 1 mg/kg.

This imaging can be performed by molecular imaging methods such as positron emission tomography (PET), fluorescence microscopy measurement, multi-photon imaging, two-photon imaging, near-infrared fluorescence imaging, autoradiography, and single-photon emission computed tomography (SPECT). Also, this imaging includes in vitro, ex vivo, and in vivo imaging.

In one embodiment, the present invention provides a composition, which is for diagnosing diseases that are caused by accumulation of tau proteins in the brain, and which contains the compound of the formula (I), or a pharmaceutically acceptable salt or a solvate thereof. In another embodiment, the present invention provides a method of diagnosing diseases that are caused by accumulation of tau proteins, including administering the compound of the formula (I), or a pharmaceutically acceptable salt or a solvate thereof, to a mammal.

Diseases that are caused by accumulation of tau proteins include, for example, Alzheimer's disease, non-Alzheimer-type tauopathies (including frontotemporal lobar degeneration), or other tau-positive neurodegenerative diseases. To be more specific, diseases that are caused by accumulation of tau proteins include, besides Alzheimer's disease, progressive supranuclear palsy (PSP), Pick's disease, corticobasal degeneration (CBD), frontotemporal lobar degeneration (FTLD), frontotemporal dementia with Parkinsonism linked to chromosome 17 (FTDP-17), argyrophilic grain disease (AGD), dementia pugilistica-boxer's encephalopathy, Parkinson-dementia complex of Guam, or neurofibrillary tangle-predominant dementia.

In another embodiment, the present invention provides a method of diagnosing a disease that is caused by accumulation of tau proteins, and this diagnosis method includes (a) a step of administering an effective dose of the compound of the formula (I), or a pharmaceutically acceptable salt or a solvate thereof, to a mammal, and (b) a step of imaging the brain of the mammal. In another embodiment, the above method further includes (c) a step of comparing the image of the brain of the mammal with that of a normal mammal. If the fluorescence intensity and/or the radiation intensity of the compound of the present invention show an increase compared to the normal mammal, this indicates that a disease to be caused by accumulation of tau proteins might have developed or that there is a danger of developing it.

In yet another embodiment, the present invention provides use of the compound of the formula (I), or a pharmaceutically acceptable salt or a solvate thereof, for preparing a composition for tau imaging. In yet another embodiment, the present invention provides use of the compound of the formula (I), or a pharmaceutically acceptable salt or a solvate thereof, for preparing a composition for diagnosing diseases such as Alzheimer's disease, frontotemporal lobar degeneration, dementia, or other neurodegenerative tauopathies.

In one embodiment, the present invention provides a method of screening a compound for treating or preventing a disease or a symptom that is caused by accumulation of tau proteins in the brain, and this screening method includes (a) a step of administering, to a mammal having a disease or a symptom that is caused by accumulation of tau proteins, a candidate compound for treating or preventing the disease or symptom, (b) a step of administering an effective dose of the compound of the formula (I) or a pharmaceutically acceptable salt thereof, to the mammal, and (c) a step of imaging the brain of the mammal.

The above screening method can further include (d-1) a step of comparing the image of the brain of the mammal with that from before the administration of the candidate compound. If, after the candidate compound is administered, the fluorescence intensity and/or the radiation intensity of the compound of the present invention show a decrease compared to those from before the administration of the candidate compound, this indicates that the candidate compound is effective as a compound for treating the disease or the symptom. Alternatively, the above method can include (d-2) a step of comparing the image of the brain of the mammal with an image of another normal mammal. If, after the candidate compound is administered, the fluorescence intensity and/or the radiation intensity of the compound of the present invention are equal to those of the normal mammal, this indicates that the candidate compound is effective as a compound for treating the disease or the symptom.

EMBODIMENTS

7. Embodiments

Embodiments of the present invention will be described below. These embodiments will be described only to deepen the understanding of the claims of the present invention, and are by no means intended to limit the claims of the present invention.

Synthesis of the Compounds of the Present Invention

Synthesis Embodiment 1

Synthesis of 4-((1E,3E)-4-(benz[d]thiazole-2-yl)buta-1,3-dienyl)-N,N-dimethylaniline (PBB1)

PBB1 was synthesized according to the following synthesis scheme.

Synthesis scheme

[Formula 44]

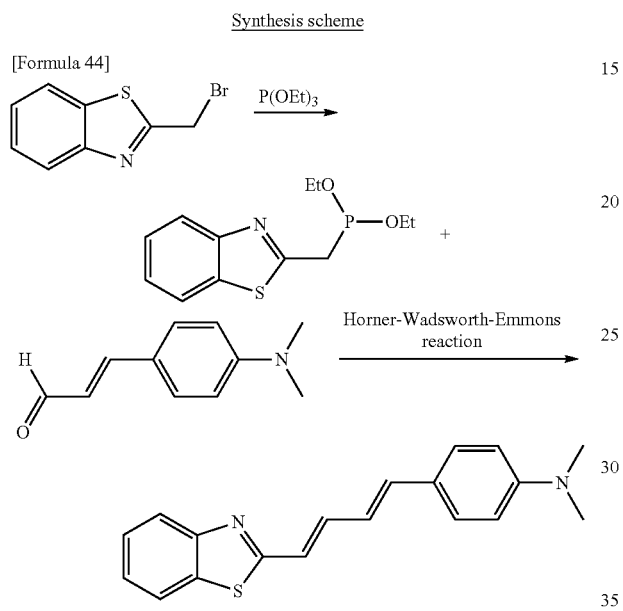

2-(bromomethyl)benzothiazole (Wako Code: Alfa Aesar, H26120) was reacted with trimethyl phosphite (Wako Code: 200-09082, 204-09085), and the resulting product was reacted with p-(dimethylamino)cinnamaldehyde (Wako Code: 045-16441, 041-16443, 043-16442), and the target compound was obtained.

PBB1: $^1$H NMR (300 MHz, DMSO-$d_6$) δ ppm: 8.04 (d, J=7.80 Hz, 1H), 7.90 (d, J=7.80 Hz, 1H), 7.48 (dd, J=7.80 Hz, 7.80 Hz, 1H), 7.36-7.43 (m, 4H), 6.89-6.98 (m, 3H), 6.72 (d, J=8.7 Hz, 2H), 2.96 (s, 6H)

Synthesis Embodiment 2

Synthesis of 2-((1E,3E)-(4-(methylamino)phenyl)buta-1,3-dienyl)benz[d]thiazole-6-ol (PBB2)

PBB2 was synthesized according to the following synthesis scheme.

Synthesis scheme

[Formula 45]

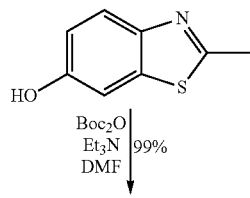

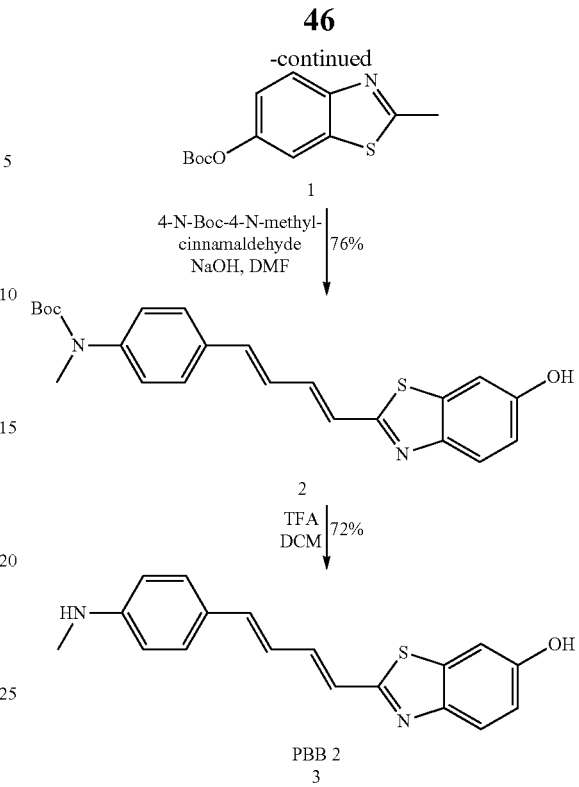

Step 1: Synthesis of carboxylic acid tert-butylester2-methyl-benzothiazole-6-ylester (1)

Triethylamine (6.58 ml, 47.5 mmol) and an anhydrous dimethylformamide solution (48 ml) of di-tert-butyl dicarbonate (10.8 g, 49.5 mmol) were added in an anhydrous dimethylformamide solution (150 ml) of 2-methyl-benzothiazole-6-ol (3.27 g, 19.8 mmol). The reaction mixture was stirred for 16 hours. The reaction mixture was condensed, and the residue was refined by column chromatography (ethyl acetate/hexane=1:3). The desired product was obtained as a pale brown solid, at a yield of 99% (5.23 g).

$^1$H NMR (400 MHz, CDCl$_3$) δ ppm 7.91 (d, J=8.8 Hz, 1H), 7.66 (d, J=2.3 Hz, 1H), 7.25 (dd, J=8.8, 2.4 Hz, 1H), 2.82 (s, 3H), 1.57 (s, 9H).

Step 2: Synthesis of carboxylic acid 2-{4-[4-(tert-butoxycarbonyl-methyl-amino)-phenyl]-buta-1,3-dienyl}-benzothiazole-6-ylestertert-butylester (2)

Finely powdered sodium hydroxide (892 mg, 22.3 mmol) was added in a dimethylformamide solution (15 ml) of carboxylic acid tert-butylester2-methyl-benzothiazole-6-ylester (1) (947 mg, 3.57 mmol). The solution was stirred for 10 minutes, and, after that, a dimethylformamide solution (6.2 ml) of 4-N-Boc-4-N-methyl-cinnamaldehyde (933 mg, 3.57 mmol) was added dropwise. The reaction mixture was stirred for 3.5 hours. The reaction mixture was diluted with ethyl acetate, and was washed with water. The aqueous phase was extracted 5 times using ethyl acetate. The combined ethyl acetate phase was dried with sodium sulfate and condensed. The residue was refined by column chromatography (ethyl acetate/hexane=1:3→1:2). The desired product was obtained as a bright yellow solid, at a yield of 76% (1.12 g).

$^1$H NMR (400 MHz, CDCl$_3$) δ ppm 8.33 (bs, 1H), 7.67 (d, J=8.8 Hz, 1H), 7.27 (d, J=8.5, Hz, 2H), 7.18 (d, J=8.5 Hz, 2H), 7.08 (dd, J=15.4, 10.5 Hz, 1H), 7.04 (bs, 1H), 6.84 (d, J=15.4 Hz, 1H), 6.90-6.78 (m, 1H), 6.71 (dd, J=15.2, 10.5 Hz, 1H), 6.61 (d, J=15.5 Hz, 1H), 3.26 (s, 3H), 1.51 (s, 9H). (Note that 4-N-Boc-4-N-methyl-cinnamaldehyde was synthesized according to the method disclosed in Japanese Unexamined Patent Application Publication No. 2007-106755).

Step 3: Synthesis of 2-[4-(4-methylamino-phenyl)-buta-1,3-dienyl]-benzothiazole-6-ol (3)) Carboxylic acid 2-{4-[4-(tert-butoxycarbonyl-methyl-amino)-phenyl]-buta-1,3-dienyl}-benzothiazole-6-ylestertert-butylester (2) (1.07 g, 26.3 mmol) was suspended in dichloromethane (15.8 ml). Trifluoroacetic acid (15.8 ml) was added and the red solution was stirred for 2 hours. The reaction mixture was condensed, and the residue was dissolved in water. The solution was neutralized by addition of a saturated sodium hydrogen carbonate solution. The product was precipitated, and this was washed 3 times with water, and 3 times with diethyl ether. The desired product was obtained as a red brown solid, at a yield of 72% (587 mg).

PBB2: $^1$H NMR (400 MHz, DMF-d$_7$) δ ppm 9.56 (bs, 1H), 7.72 (d, J=8.7 Hz, 1H), 7.39 (d, J=2.2 Hz, 1H), 7.37 (d, J=8.6, Hz, 2H), 7.28 (dd, J=15.5, 8.9 Hz, 1H), 7.03 (dd, J=8.7, 2.0 Hz, 1H), 6.95-6.81 (m, 2H), 6.85 (d, J=15.4 Hz, 1H), 6.64 (d, J=8.4 Hz, 2H), 5.65 (bs, 1H), 2.83 (s, 3H) ESI-MS: m/z 309 [M−41]+

Synthesis Embodiment 3

Synthesis of 2-((1E,3E)-4-(6-(methylamino)pyridine-3-yl)buta-1,3-dienyl)benz[d]thiazole-6-ol (PBB3)

PBB3 was synthesized according to the following synthesis scheme.

Synthesis scheme

[Formula 46]

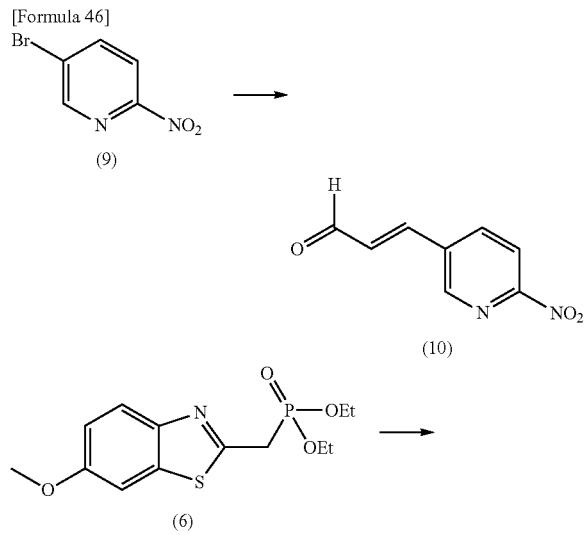

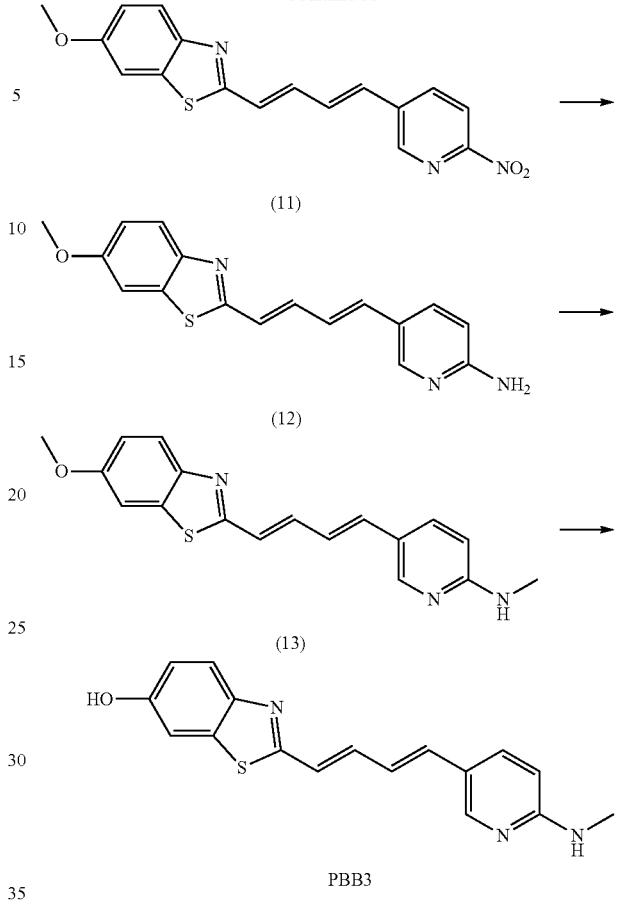

Step 1: Synthesis of Compound (10)

Under an argon atmosphere, 3,3-diethoxy-1-propene (58.58 g, 450.0 mmol), potassium chloride (11.18 g, 150.0 mmol), tetrabutylammonium and acetate (13.57 g, 45.0 mmol), potassium carbonate (31.10 g, 225.0 mmol) and palladium acetate (1.68 g, 7.5 mmol) were added in a N,N-dimethylformamide solution (450 mL) of the compound (9) (30.45 g, 150.0 mmol), heated to 100° C., and stirred all night. The reaction liquid was filtered and ethyl acetate and 1N hydrochloric acid were added thereto, and the reaction liquid was stirred. The reaction liquid was neutralized by adding a sodium hydrogen carbonate aqueous solution, and the organic layer was extracted with ethyl acetate. After drying with anhydrous sodium sulphate, the solvent was distillated under reduced pressure. By refining the residue by column chromatography (developing solvent: chloroform), 3.31 g of the title compound (10) was obtained.

Step 2: Synthesis of Compound (11)

Under an argon atmosphere, after a tetrahydrofuran solution (166 mL) of the compound (6) (5.98 g, 18.96 mmol) was cooled with ice, sodium hydride (60% oil, 758 mg, 18.96 mmol) was added. The reaction liquid was heated to room temperature, and, after stirring for 30 minutes, the compound (10) (2.94 g, 16.50 mmol) was added. After the disappearance of the raw material, the reaction liquid was added in water and stirred, and the precipitate was filtered. Toluene was added to the cake, and the solvent was distillated under reduced pressure, and suspended and washed with toluene. The precipitate was filtered and dried under reduced pressure, thereby giving 4.06 g of the title compound (11).

Step 3: Synthesis of Compound (12)

Acetic acid (76 mL), iron (3.06 g, 54.79 mmol) and 12N hydrochloric acid (16 mL) were added in an ethanol solution (76 mL) of the compound (11) (3.96 g, 11.67 mmol), and the resultant solution was stirred all night. The reaction liquid was added dropwise in a sodium hydroxide aqueous solution under ice cold conditions, and the precipitate was filtered. Methanol was added to the cake, and the resultant mixture was stirred and filtered. By distillating the filtrate under reduced pressure and refining the residue by column chromatography (developing solvent: chloroform→chloroform/methanol=20/1), 1.29 g of the title compound (12) was obtained.

Step 4: Synthesis of Compound (13)

Under an argon atmosphere, after a N,N-dimethylformamide solution (21 mL) of the compound (12) (1284 mg, 4.15 mmol) was cooled with ice, sodium hydride (60% oil, 183 mg, 4.57 mmol) was added. The reaction liquid was heated to room temperature, and, after stirring for 30 minutes, methyl iodide (556 mg, 3.92 mmol) was added. The reaction liquid was added in water and stirred, and extracted with chloroform. The organic layer was washed with saturated saline water, and, after drying with anhydrous sodium sulphate, the solvent was distillated under reduced pressure. By refining the residue by column chromatography (developing solvent: chloroform→chloroform/methanol=97/3), 188 mg of the title compound (13) was obtained.

Step 5: Synthesis of 2-((1E,3E-4-(6-(methylamino)pyridine-3-yl)buta-1,3-dienyl)benz[d]thiazole-6-ol (PBB3)

Under an argon atmosphere, after a dichloromethane solution (2.9 mL) of the compound (13) (184 mg, 0.57 mmol) was cooled down to −78° C., boron tribromide (1.0 M dichloromethane solution, 2.85 mL, 2.85 mmol) was added dropwise. The reaction liquid was heated to room temperature, and stirred all night. After the reaction liquid was neutralized by adding a 1N sodium hydroxide aqueous solution and sodium hydrogen carbonate under ice cold conditions, the precipitate was filtered. The cake was washed with water and diethyl ether, and after methanol was added thereto and the resultant mixture was stirred, the resultant mixture was filtered. After the filtrate was distillated under reduced pressure, 120 mg of the title compound was obtained by refining the residue by column chromatography (developing solvent: chloroform/methanol=97/3→19/1).

PBB3: $^1$H NMR (400 MHz, DMSO-$d_6$) δ ppm: 9.83 (s, 1H), 8.09 (d, J=2.29 Hz, 1H), 7.71 (d, J=8.70 Hz, 1H), 7.69 (dd, J=9.16 Hz, 2.29 Hz, 1H), 7.32 (d, J=2.75 Hz, 1H), 7.22 (dd, J=15.57 Hz, 10.53 Hz, 1H), 6.87-7.00 (m, 3H), 6.84 (d, J=15.57 Hz, 1H), 6.83 (d, J=15.11 Hz, 1H), 6.48 (d, J=8.70 Hz, 1H), 2.80 (d, J=5.04 Hz, 3H)

Synthesis Embodiment 4

Synthesis of 2-((1E, 3E)-4-(6-(methylamino)pyridine-3-yl)buta-1,3-dienyl)benz[d]thiazole-5,6-diol (PBB4)

PBB4 was synthesized according to the following synthesis scheme.

Synthesis scheme

[Formula 47]

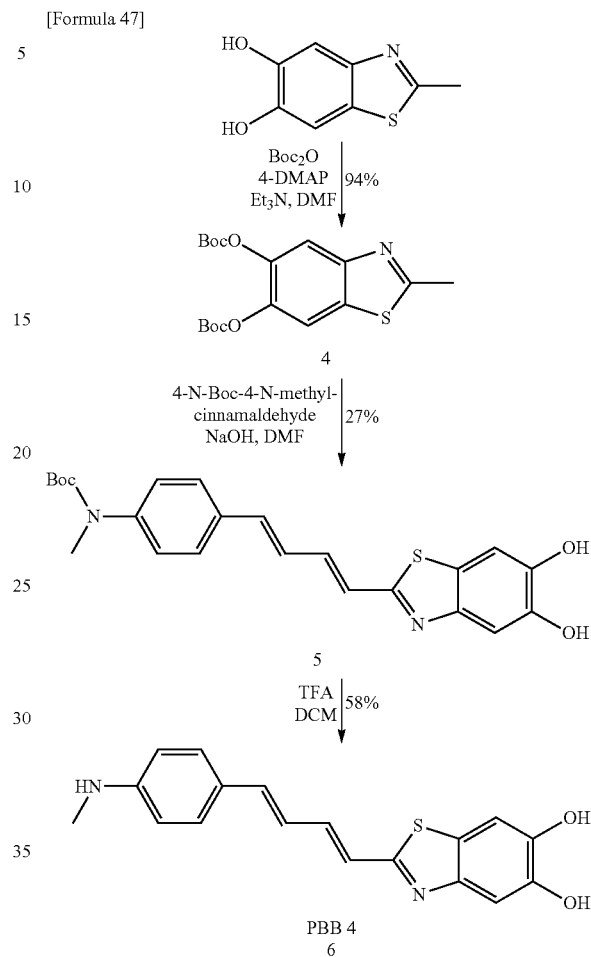

Step 1: Synthesis of 6-tert-butoxycarbonyloxy-2-methyl-benzothiazole-5-ylestertert-butylester (4)

Triethylamine (23.2 ml, 172 mmol), an anhydrous dimethylformamide solution (48 ml) of di-tert-butyl dicarbonate (37.4 g, 172 mmol), and 4-dimethylaminopyridine (838 mg, 6.86 mmol) were added in an anhydrous dimethylformamide solution (260 ml) of 2-methyl-benzothiazole-5,6-diol (6.22 g, 34.3 mmol). The reaction mixture was stirred for 4 hours. The reaction mixture was condensed, and the residue was refined by column chromatography (ethyl acetate/hexane=1:4). The desired product was obtained as a pale brown solid, at a yield of 93% (12.26 g).

$^1$H NMR (400 MHz, CDCl$_3$) δ ppm 7.81 (s, 1H), 7.72 (s, 1H), 2.82 (s, 3H), 1.564 (s, 9H), 1.558 (s, 9H).

Step 2: Synthesis of {4-[4-(5,6-dihydroxy-benzothiazole-2-yl)-buta-1,3-dienyl]-phenyl}-methyl-carbamic acid tert-butylester (5)

Finely powdered sodium hydroxide (1.42 g, 35.6 mmol) was added in a dimethylformamide solution (30 ml) of 6-tert-butoxycarbonyloxy-2-methyl-benzothiazole-5-ylestertert-butylester (4) (2.17 g, 5.7 mmol). The solution was stirred for 10 minutes, and, after that, a dimethylformamide solution (4.2 ml) of 4-N-Boc-4-N-methyl-cinnamaldehyde/ cinnamaldehyde (1.5 g, 5.74 mmol) was added dropwise. The reaction mixture was stirred for 4.5 hours. The reaction mixture was diluted with ethyl acetate, and was washed with water. The aqueous phase was extracted 5 times using ethyl acetate. The combined ethyl acetate phase was dried with sodium sulfate, and condensed. The residue was refined by column chromatography (ethyl acetate/hexane=1:1). The desired product was obtained as an orange-yellow solid at a yield of 27% (667 mg).

$^1$H NMR (400 MHz, DMSO-D6) δ ppm 9.51 (bs, 1H), 9.42 (bs, 1H), 7.51 (d, J=8.5, Hz, 2H), 7.29 (d, J=8.3, Hz, 2H), 7.285 (s, 1H), 7.26 (s, 1H), 7.23-7.10 (m, 2H), 6.95 (d, J=15.1 Hz, 1H), 6.94 (d, J=15.1 Hz, 1H), 3.19 (s, 3H), 1.40 (s, 9H).

Step 3: Synthesis of 2-[4-(4-methylamino-phenyl)-buta-1,3-dienyl]-benzothiazole-5,6-diol (6)

{4-[4-(5,6-dihydroxybenzothiazole-2-yl)-buta-1,3-dienyl]-phenyl}-methyl-carbamic acid tert-butylester (5) (614 mg, 1.45 mmol) was suspended in dichloromethane (8 ml). Trifluoroacetic acid (8 ml) was added, and the red solution was stirred for 2 hours. The reaction mixture was condensed, and the residue was dissolved in water. The solution was neutralized by addition of a saturated sodium hydrogen carbonate solution. The product was precipitated, and this was washed 3 times with water, and 3 times with diethyl ether. The desired product was obtained as a brown solid, at a yield of 58% (276 mg).

PBB4: $^1$H NMR (400 MHz, DMF-$d_7$) δ ppm 9.60 (bs, 2H), 7.52-7.29 (m, 4H), 7.27 (dd, J=15.2, 10.6 Hz, 1H), 6.96 (dd, J=15.2, 10.3 Hz, 1H), 6.91-6.81 (m, 2H), 6.63 (d, J=8.1 Hz, 2H), 6.06 (d, J=4.1 Hz, 1H), 2.81 (d, J=4.3 Hz, 3H). ESI-MS: m/z 325 [M+H]+

Synthesis Embodiment 5

Synthesis of 2-((1E,3E)-4-(4-(dimethylamino)phenyl)buta-1,3-dienyl)-3-ethyl-6-methoxybenzo[d]thiazole-3-ium (mPBB5)

The synthesis was performed by a method that was similar to the synthesis method of PBB5.

Synthesis Embodiment 6

Synthesis of (E)-2-(4-(4-(dimethylamino)phenyl)buta-1-en-3-ynyl)benz[d]thiazole-6-ol (PBB2.1)

The synthesis was performed by a method similar to that of following synthesis example 10.

Synthesis Embodiment 7

Synthesis of (E)-2-(4-(4-(methylamino)phenyl)buta-1-en-3-ynyl)benz[d]thiazole-6-ol (PBB2.2)

The synthesis was performed by a method similar to that of following synthesis example 10.

Synthesis Embodiment 8

Synthesis of (E)-2-(4-(4-aminophenyl)buta-1-en-3-ynyl)benz[d]thiazole-6-ol (PBB2.3)

The synthesis was performed by a method similar to that of following synthesis example 10.

Synthesis Embodiment 9

Synthesis of (E)-2-(4-(6-(dimethylamino)pyridine-3-yl)buta-1-en-3-ynyl)benz[d]thiazole-6-ol (PBB3.1)

The synthesis was performed by a method similar to that of following synthesis example 10.

Synthesis Embodiment 10

Synthesis of (E)-2-(4-(6-(methylamino)pyridine-3-yl)buta-1-en-3-ynyl)benz[d]thiazole-6-ol (PBB3.2)

PBB3.2 was synthesized according to the following synthesis scheme.

Synthesis scheme

[Formula 48]

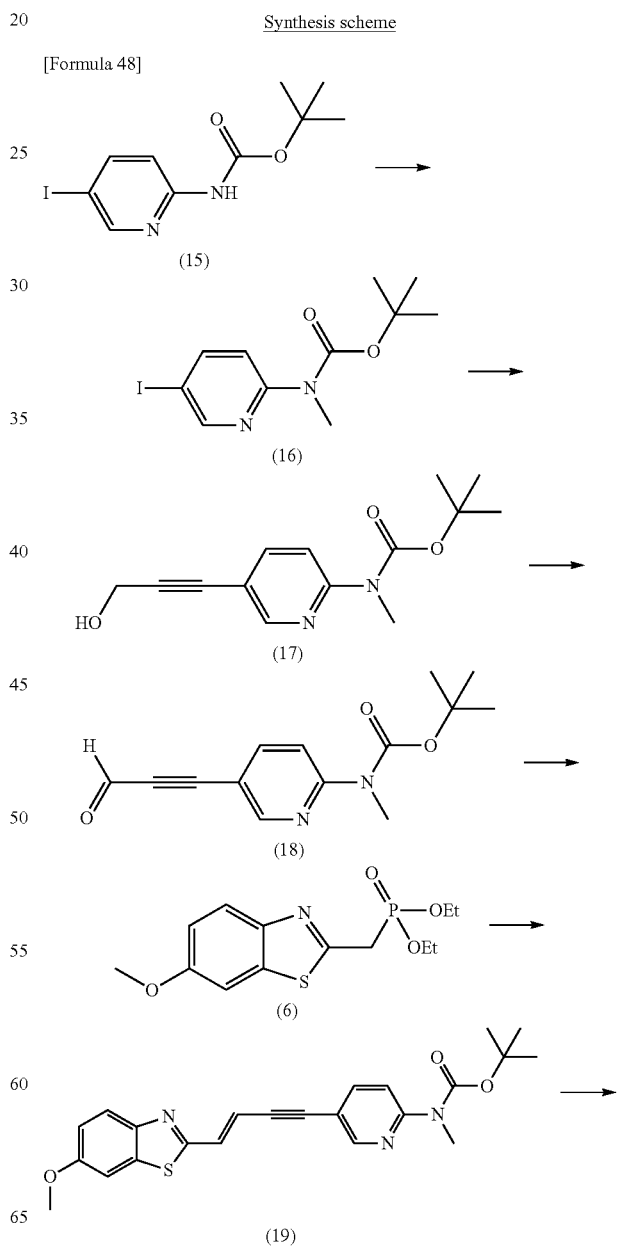

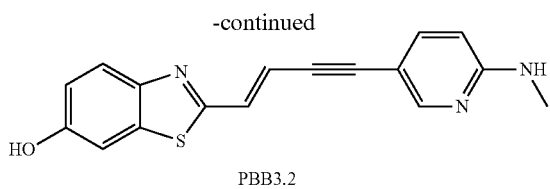

PBB3.2

Step 1: Synthesis of Compound (16)

Under an argon atmosphere, after a N,N-dimethylformamide solution (2.9 mL) of 2-(t-butoxycarbonylamino)-5-iodopyridine (15) (640 mg, 2.00 mmol) was cooled with ice, cesium carbonate (1088 mg, 3.34 mmol) and methyl iodide (497 mg, 3.50 mmol) were added, and the resultant solution was stirred. After the disappearance of the raw material was confirmed, water was added in the reaction liquid, and the organic layer was extracted using ethyl acetate. The organic layer was washed with water and saturated saline water, and, after drying with anhydrous sodium sulphate, the solvent was distilled under reduced pressure. By refining the residue by column chromatography (developing solvent: heptane/ethyl acetate=50/1→heptane/ethyl acetate=10/1), 575 mg of the title compound (16) was obtained.

Step 2: Synthesis of Compound (17)

Under an argon atmosphere, copper iodide (39 mg, 0.20 mmol), 2-propyn-1-ol (191 mg, 3.41 mmol) and dichlorobis(triphenylphosphine) palladium (II) (24 mg, 0.03 mmol) were added in a triethylamine solution (1.66 mL, 11.90 mmol) of the compound (16) (568 mg, 1.70 mmol), and the resultant solution was stirred. After the disappearance of the raw material was confirmed, water was added in the reaction liquid, and the organic layer was extracted using ethyl acetate. The organic layer was washed with water and saturated saline water, and, after drying with anhydrous sodium sulphate, the solvent was distilled under reduced pressure. By refining the residue by column chromatography (developing solvent: heptane/ethyl acetate=4/1→heptane/ethyl acetate=3/2), 400 mg of the title compound (17) was obtained.

Step 3: Synthesis of Compound (18)

Under an argon atmosphere, triethylamine (501 mg, 4.95 mmol) and a pyridine sulfur trioxide complex (716 mg, 4.50 mmol) were added in a dimethylsulfoxide solution (7.50 mL) of the compound (17) (393 mg, 1.50 mmol), and the resultant solution was stirred. After the disappearance of the raw material was confirmed, water was added in the reaction liquid, and the organic layer was extracted using ethyl acetate. The organic layer was washed with water and saturated saline water, and, after drying with anhydrous sodium sulphate, the solvent was distilled under reduced pressure. By refining the residue by column chromatography (developing solvent: heptane/ethyl acetate=20/1→heptane/ethyl acetate=10/1), 315 mg of the title compound (18) was obtained.

Step 4: Synthesis of Compound (19)

Under an argon atmosphere, after a tetrahydrofuran solution (10 mL) of the compound (6) (315 mg, 1.00 mmol) was cooled with ice, sodium hydride (60% oil, 48 mg, 1.20 mmol) was added. After the reaction liquid was heated to room temperature and stirred for 30 minutes, the compound (18) (312 mg, 1.20 mmol) was added. After the disappearance of the raw material, water was added in the reaction liquid, and the organic layer was extracted using ethyl acetate. The organic layer was washed with water and saturated saline water, and, after drying with anhydrous sodium sulphate, the solvent was distillated under reduced pressure. By refining the residue by column chromatography (developing solvent: heptane/ethyl acetate=10/1→heptane/ethyl acetate=5/1), 340 mg of the title compound (18) was obtained.

Step 5: Synthesis of (E)-2-(4-(6-(methylamino)pyridine-3-yl)buta-1-en-3-ynyl)benz[d]thiazole-6-ol (PBB3.2)

Under an argon atmosphere, after a dichloromethane solution (4.0 mL) of the compound (18) (336 mg, 0.80 mmol) was cooled down to −50° C., boron tribromide (1.0M dichloromethane solution, 6.38 mL, 6.38 mmol) was added dropwise. The reaction liquid was heated to room temperature and stirred all night. After a 1N sodium hydroxide aqueous solution and sodium hydrogen carbonate were added in the reaction liquid under ice cold conditions and neutralized, the precipitate was filtered. The cake was washed with water and diisopropyl ether. After methanol was added and the cake was stirred, the precipitate was filtered and dried under reduced pressure, thereby giving 130 mg of the title compound (4).

PBB3.2: $^1$H NMR (400 MHz, DMSO-d6) δ ppm: 9.95 (s, 1H), 8.19 (d, J=2.29 Hz, 1H), 7.78 (d, J=8.07 Hz, 1H), 7.48 (dd, J=8.70 Hz, 2.29 Hz, 1H), 7.36 (d, J=2.29 Hz, 1H), 7.18 (d, J=16.03 Hz, 1H), 7.13 (q, J=4.58 Hz, 1H), 6.97 (dd, J=8.70 Hz, 2.29 Hz, 1H), 6.85 (d, J=15.57 Hz, 1H), 6.48 (d, J=8.07 Hz, 1H), 2.81 (d, J=4.58 Hz, 3H)

Synthesis Embodiment 11

Synthesis of (E)-5-(4-(6-(aminomethyl)benz[d]thiazole-2-yl)buta-3-en-1-ynyl)-N-methylpyridine-2-amine (PBB3.2N)

PBB3.2N was synthesized according to the following synthesis scheme.

[Formula 49]

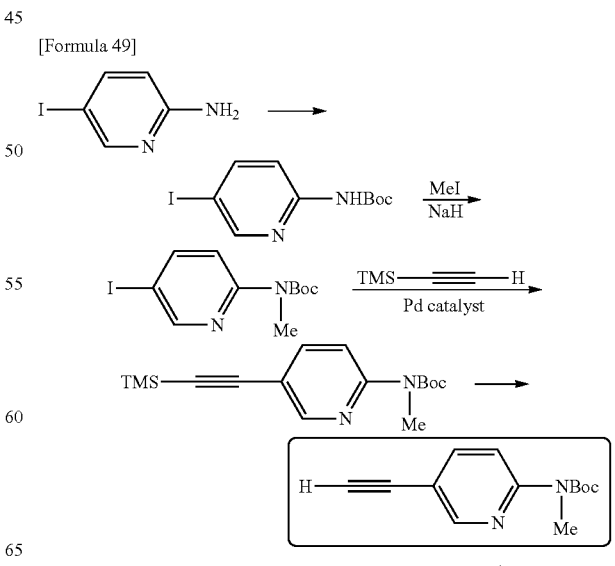

Compound A'

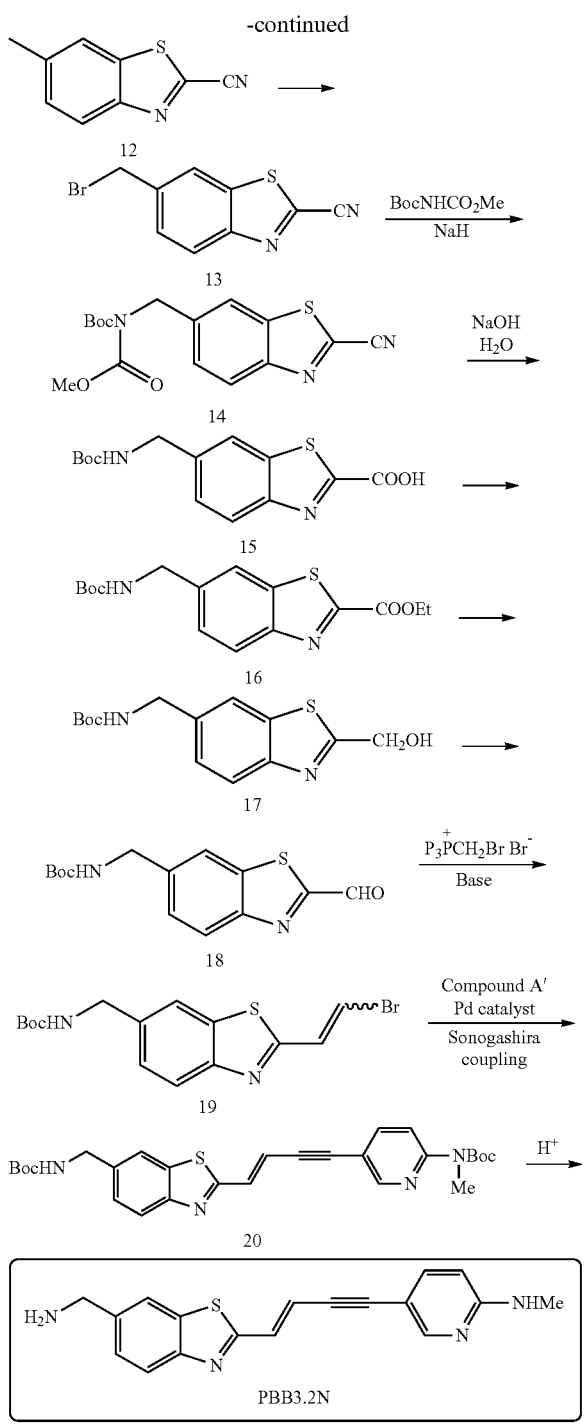

Step 1: Synthesis of 2-(N-(tert-butoxycarbonyl)-N-methylamino) ethynylpyridine (compound A')

Using 5-iodopyridine-2-amine as the starting substance, the synthesis was performed with reference to literature that described the synthesis methods of a similar substance (N-tert-butoxycarbonylation and methylation: WO2010/024769, ethynylation: C. B. Aarkeroy et al., Dalton Trans., 2006, 1627).

$^1$H-NMR (400 MHz, CDCl$_3$) δ ppm: 8.47 (d, J=2.0 Hz, 1H), 7.75 (d, J=8.8 Hz, 1H), 7.68 (dd, J=8.8 Hz, 2.0 Hz, 1H), 3.41 (s, 3H), 3.15 (s, 1H), 1.53 (s, 9H)

Note that 2-amino-5-ethynylpyridine, which was the starting substance, was synthesized with reference to literature (C. B. Aarkeroy et al., Dalton Trans., 2006, 1627).

Step 2: Synthesis of 6-(bromomethyl)benzothiazole-2-carbonitrile (13)

In carbon tetrachloride (34 mL), 6-methylbenzothiazole-2-carbonitrile (CAS No. 39785-48-3) (1.18 g, 6.77 mmol), N-bromosuccinimide (1.22 g, 6.85 mmol) and azobisisobutyronitrile (0.14 g, 0.85 mmol) were reacted for 1 hour under reflux and then condensed under reduced pressure, the residue was refined by silica gel column chromatography, and the title compound was obtained as a yellowish white solid (1.17 g, 4.62 mmol).

$^1$H-NMR (400 MHz, CDCl$_3$) δ ppm: 8.20 (d, J=8.4 Hz, 1H), 8.01 (d, J=1.6 Hz, 1H), 7.68 (dd, J=8.4 Hz, 1.6 Hz, 1H), 4.64 (s, 2H)

Step 3: Synthesis of N-(2-cyanobenzothiazole-6-ylmethyl)iminodicarboxylic acid tert-butylmethyl (14)

A DMF solution (6 mL) of iminodicarboxylic acid tert-butylmethyl (0.48 g, 2.8 mmol) was cooled with ice, 60% sodium hydride (0.11 g, 2.8 mmol) was added thereto, and the resultant solution was stirred for 30 minutes. Next, a DMF solution (6 mL) of 6-(bromomethyl)benzothiazole-2-carbonitrile (0.58 g, 2.3 mmol) was added, and the resultant mixture was stirred for 30 minutes at room temperature. The reaction mixture was added water and extracted with ethyl acetate, the crude product was refined by silica gel column chromatography, and the title compound was obtained as a liquid that was virtually colorless (0.71 g, 2.0 mmol).

$^1$H-NMR (400 MHz, CDCl$_3$) δ ppm: 8.17 (d, J=8.4 Hz, 1H), 7.92 (d, J=1.6 Hz, 1H), 7.60 (dd, J=8.4 Hz, 1.6 Hz, 1H), 5.01 (s, 2H), 3.85 (s, 3H), 1.45 (s, 9H)

Step 4: Synthesis of 6-((tert-butoxycarbonylamino)methyl)benzothiazole carboxylic acid methyl (16)

A 5M sodium hydroxide aqueous solution (2.05 mL, 10.25 mmol) was added in a methanol solution (19 mL) of N-(2-cyanobenzothiazole-6-ylmethyl)iminodicarboxylic acid tert-butylmethyl (0.71 g, 2.0 mmol), and the resultant solution was stirred for 4 days at room temperature. After the solution was neutralized with dilute hydrochloric acid, water was added thereto, the organic layer was extracted with ethyl acetate, and the solvent was washed with saturated saline water and dried with anhydrous sodium sulphate. The solvent was distillated at reduced pressure, the residue was dissolved in methanol (25 mL) and 1M hydrochloric acid (1.04 mL, 1.04 mmol) was added thereto, and the resultant mixture was stirred for 30 minutes at room temperature. Furthermore, after the mixture was added 1M hydrochloric acid (1.04 mL, 1.04 mmol), stirred for 30 minutes at room temperature and diluted with ethyl acetate, the resultant mixture was washed with water, dried, and condensed at reduced pressure, and the title compound was obtained as a solid that was virtually white (0.62 g, 2.0 mmol).

$^1$H-NMR (400 MHz, CDCl$_3$) δ ppm: 8.19 (d, J=8.4 Hz, 1H), 7.90 (s, 1H), 7.50 (d, J=8.4 Hz, 1H), 5.0 (br, 1H), 4.49 (br d, J=5.2 Hz, 2H), 4.09 (s, 3H), 1.48 (s, 9H)

Step 5: Synthesis of (6-((tert-butoxycarbonylamino)methyl)benzothiazole-2-yl)methanol (17)

Sodium borohydride (359 mg, 9.49 mmol) was added in a methanol solution (52 mL) of 6-((tert butoxycarbonylamino)methyl)benzothiazole-2-carboxylic acid methyl (1.02 g, 3.16 mmol), and the resultant solution was stirred at room temperature for 1 hour. Water was added to the reaction mixture, and the organic layer was extracted with ethyl acetate and dried with anhydrous sodium sulphate. The solvent was distillated at reduced pressure, and the title compound was obtained as a pale yellowish white solid (0.93 g, 3.16 mmol).

$^1$H-NMR (400 MHz, CDCl$_3$) δ ppm: 7.92 (d, J=8.4 Hz, 1H), 7.80 (s, 1H), 7.38 (d, J=8.4 Hz, 1H), 5.07 (s, 2H), 5.0 (br, 1H), 4.44 (br d, J=6.0 Hz, 2H), 2.97 (br, 1H), 1.47 (s, 9H)

Step 6: Synthesis of 6-((tert-butoxycarbonylamino) methyl)benzothiazole-2-carboxaldehyde (18)

A Dess-Martin reagent (2.52 g, 5.94 mmol) was added in a dichloromethane solution (80 mL) of (6-((tert-butoxycarbonylamino)methyl)benzothiazole-2-yl)methanol (1.65 g, 5.61 mmol), and the resultant solution was stirred at room temperature for 16 hours. The reaction mixture was refined by silica gel column chromatography, and the title compound was obtained as a white solid (1.43 g, 4.89 mmol).

$^1$H-NMR (400 MHz, CDCl$_3$) δ ppm: 10.16 (s, 1H), 8.20 (d, J=8.4 Hz, 1H), 7.93 (d, J=1.6 Hz, 1H), 7.54 (dd, J=8.4 Hz, 1.6 Hz, 1H), 5.0 (br, 1H), 4.50 (br d, J=6.0 Hz, 2H), 1.48 (s, 9H)

Step 7: Synthesis of 2-((0-2-bromoethenyl)-6-((tert-butoxycarbonylamino)methyl)benzothiazole (19)

(Bromodifluormethyl) triphenyiphosphonium bromide (2.70 g, 6.19 mmol) was suspended in THF (27.5 mL), and the resultant mixture was cooled down to −78° C., added a THF solution (21 mL) of potassium tert-butoxide (703.5 mg, 6.27 mmol) at or below −55° C., and was stirred for 1 hour. Next, a THF solution (24.5 mL) of 6-((tert-butoxycarbonylamino)methyl)benzothiazole-2-carboxaldehyde (1.43 g, 4.89 mmol) was added, and the resultant mixture was stirred at −78° C. for 3.5 hours. After the reaction liquid was brought to near 0° C., a saturated sodium hydrogen carbonate aqueous solution (30 mL) was added thereto, followed by water and ethyl acetate, and the resultant mixture was separated. After the organic layer was dried and condensed under reduced pressure, refining was performed by silica gel column chromatography, and the title compound was obtained as a white solid (0.64 g, 1.73 mmol).

$^1$H-NMR (400 MHz, CDCl$_3$) δ ppm: 7.95 (d, J=8.4 Hz, 1H), 7.77 (br s, 1H), 7.40 (br d, J=8.4 Hz, 1H), 7.395 (d, J=14 Hz, 1H), 7.388 (d, J=14 Hz, 1H), 4.9 (br, 1H), 4.43 (br d, J=6.0 Hz, 2H), 1.47 (s, 9H)

Step 8: Synthesis of (E)-5-(4-(6-((tert-butoxycarbonylamino)methyl)benzothiazole-2-yl)-3-butene-1-ynyl)-2-(N-(tert-butoxycarbonyl)-N-methyl)aminopyridine (20)

From 2-(N-(tert-butoxycarbonyl)-N-methylamino)-5-ethynylpyridine (0.83 g, 3.57 mmol) and 2-((E)-2-bromoetheny0-6-((tert-butoxycarbonylamino)methyl)benzothiazole (0.64 g, 1.73 mmol), the title compound was obtained (0.68 g, 1.31 mmol) in the same procedure as step 5 of following synthesis example 33.

$^1$H-NMR (400 MHz, CDCl$_3$) δ ppm: 8.49 (d, J=1.6 Hz, 1H), 7.96 (d, J=8.4 Hz, 1H), 7.81 (d, J=8.8 Hz, 1H), 7.78 (br s, 1H), 7.70 (dd, J=8.8 Hz, 2.4 Hz, 1H), 7.40 (br d, J=8.4 Hz, 1H), 7.25 (d, J=16.0 Hz, 1H), 6.84 (d, J=16.0 Hz, 1H), 4.95 (br, 1H), 4.45 (br d, J=5.2 Hz, 2H), 3.40 (s, 3H), 1.54 (s, 9H), 1.48 (s, 9H)

Step 9: Synthesis of (E)-5-(4-(6-(aminomethyl)benzothiazole-2-yl)-3-butene-1-ynyl)-2-(methylamino)pyridine (PBB3.2N)

(E)-5-(4-(6-((tert-butoxycarbonylamino)methyl)benzothiazole-2-yl)-3-butene-1-ynyl)-2-(N-(tert-butoxycarbonyl)-N-methyl)aminopyridine (0.28 g, 0.54 mmol) was added to a liquid mixture of dichloromethane (4.4 mL) and trifluoroacetic acid (4.4 mL), and the resultant liquid mixture was stirred at room temperature for 3.5 hours, and, after that, condensed at reduced pressure. A saturated sodium hydrogen carbonate aqueous solution was added to the residue, and, after stirring for a while, the solid was filtered, washed several times with water, and dried at reduced pressure at 25° C., and the title compound was obtained as an orange powdered solid (168.5 mg, 0.527 mmol).

PBB3.2N: $^1$H-NMR (400 MHz, CD$_3$OD) δ ppm: 8.13 (d, J=1.6 Hz, 1H), 7.93 (d, J=1.2 Hz, 1H), 7.89 (d, J=8.4 Hz, 1H), 7.52-7.48 (m, 2H), 7.16 (d, J=16.0 Hz, 1H), 6.94 (d, J=16.0 Hz, 1H), 6.50 (dd, J=8.8 Hz, 0.4 Hz, 1H), 3.94 (s, 2H), 2.89 (s, 3H)

Synthesis Embodiment 12

Synthesis of 2-((1E,3E)-4-(4-aminophenyl)buta-1,3-dienyl)-6-methoxybenzo[d]thiazole-5-o 1 (Core1-4)

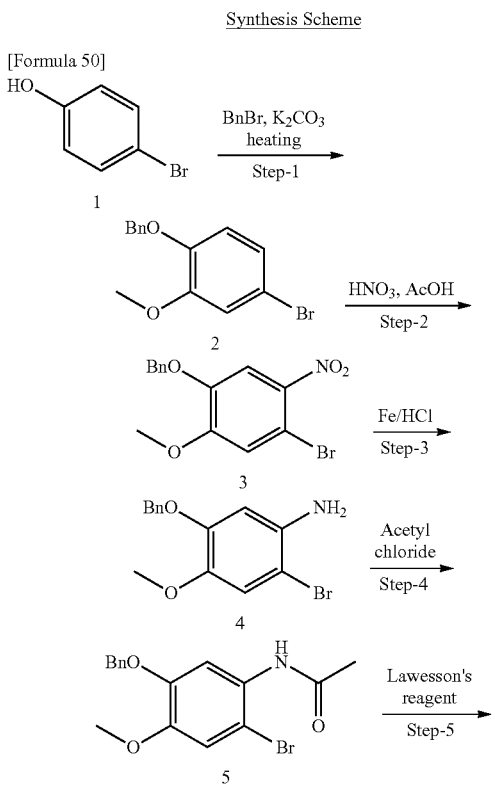

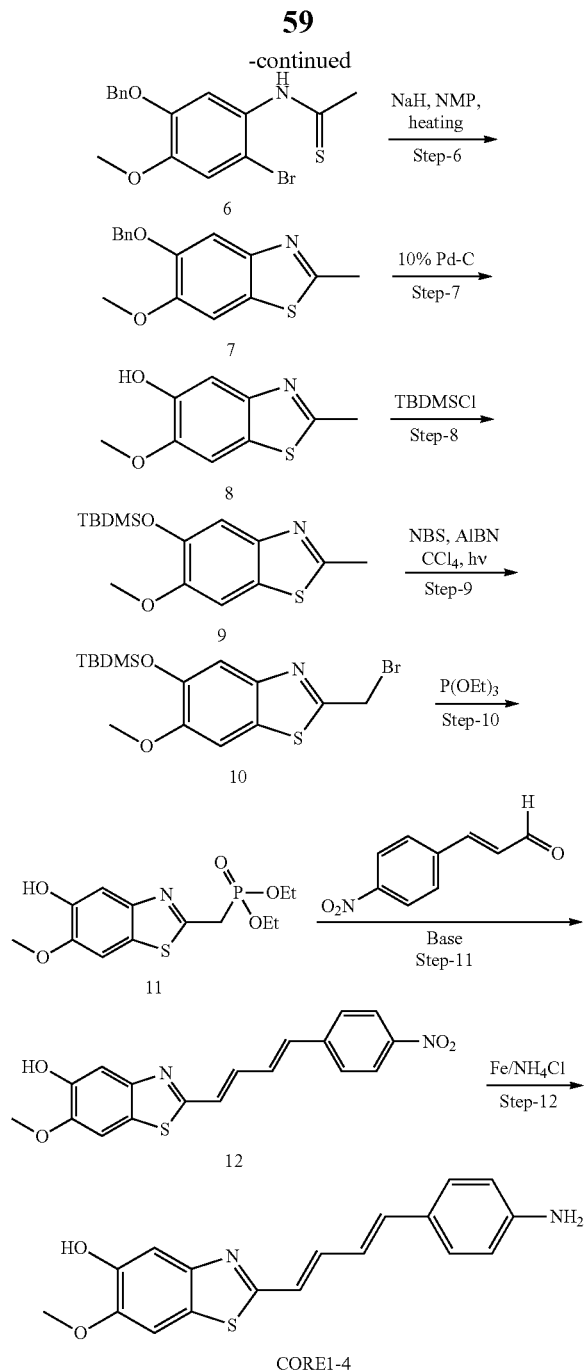

CORE1-4

(Step 1: Synthesis of 1-(benzyloxy)-4-bromo-2-methoxybenzene (2)) K₂CO₃ (30.5 g, 221 mmol) and benzyl bromide (18.9 g, 171 mmol) were added in a DMF solution (150 mL) of 1 (15 g, 73.8 mmol), and the resultant solution was stirred at 100° C. for 2 hours. The reaction was finished by adding water, and the organic layer was extracted with EtOAc. The combined organic phase was condensed. The crude product was refined, and 2 (17.6 g, 86%) was obtained.

Step 2: Synthesis of 1-(benzyloxy)-4-bromo-2-methoxy-5-nitrobenzene (3)

2 (6.73 g, 24 mmol) was added in a glacial acetic acid solution (96 mL) of concentrated HNO₃ (20 mL, 418 mmol) at −10° C., and the resultant solution was stirred for 2 hours. The suspended solid was filtered and dried, and 3 (7.6 g, 97%) was obtained.

Step 3: Synthesis of 5-(benzyloxy)-2-bromo-4-methoxyaniline (4)

3 (8 g, 23.7 mmol) was added in an ethanol (200 mL)-water (20 mL), solution, and concentrated HCl (5 mL) was added in the resultant solution dropwise at 0° C. To this, metal powder (7.95 g, 142 mmol) was added at 0° C., and the resultant mixture was stirred for 2 hours at room temperature. The reacting mass was filtered through a celite bed, the filtrate was basified with 10 N NaOH, and the organic layer was extracted with EtOAc. The combined organic phase was condensed. The crude product was refined, and 4 (5.1 g, 70%) was obtained.

Step 4: Synthesis of N-(5-(benzyloxy)-2-bromo-4-methoxyphenyl)acetamide (5)

Acetic anhydride (1.56 mL, 16.56 mmol) was added in a pyridine solution (30 mL) of 4 (5.1 g, 16.56 mmol) at 0° C., and the resultant solution was stirred at room temperature for 1 hour. The reacting mass was condensed under reduced pressure, the resulting residue was diluted with water, and the organic layer was extracted with EtOAc. The combined organic phase was condensed. By refining the crude product, 5 (5.0 g, 86%) was obtained.

Step 5: Synthesis of (N-(5-(benzyloxy)-2-bromo-4-methoxyphenyl)ethanethioamide (6)

Pyridine (2.5 mL, 28.5 mmol) and Lawesson's reagent (7.5 g, 18.6 mmol) were added in a stirred toluene solution (50 mL) of 5 (5.0 g, 14.3 mmol), and the reaction mixture was stirred at 120° C. for 2 hours. The reaction mixture was cooled down to room temperature, and the solvent was removed. After that, water was added, and the organic layer was extracted with EtOAc. The combined organic phase was condensed. The crude product was refined, and 6 (3.2 g, 61%) was obtained.

Step 6: Synthesis of 5-(benzyloxy)-6-methoxy-2-methylbenz[d]thiazole (7)

NaH (0.286 g, 1.2 mmol) was added in an NMP solution (200 mL) of 6 (2.9 g, 7.9 mmol) at room temperature. The reaction mixture was stirred at 150° C. for 2 hours. After that, the reaction was cooled down to room temperature and quenched with ice water, and the organic layer was extracted with EtOAc. The combined organic phase was condensed. The crude product was refined by column chromatography, and 7 (1.5 g, 66%) was obtained.

Step 7: Synthesis of 6-methoxy-2-methylbenz[d]thiazole-5-ol (8)

In a dichloromethane solution (35 mL) of 7 (0.92 g, 3.22 mmol) and dimethylaniline (2.49 g, 20.9 mmol), AlCl₃ (2.36 g, 17.7 mmol) was added at ⁻5° C. The reaction substance was stirred at ⁻5° C. for 10 minutes, and, after that, quenched by adding ice water, and the organic layer was extracted with dichloromethane. The combined organic phase was condensed. The crude product was refined by column chromatography, and 8 (0.52 g, 82%) was obtained.

Step 8: Synthesis of 5-(tert-butyldimethylsilyloxy)-6-methoxy-2-methylbenz[d]thiazole (9)

Imidazole (0.583 g, 8.6 mmol) was added in a DMF solution (5 mL) of 8 (0.52 g, 2.66 mmol) at 0° C. The reaction liquid was stirred at 0° C. for 10 minutes, and TBDMSCl (0.95 g, 6.3 mmol) was added. The reaction mixture was stirred for 2.5 hours at room temperature. The reaction was finished by adding water, and the organic layer was extracted with dichloromethane. The combined organic phase was condensed. The crude product was refined by column chromatography, and 9 (0.55 g, 66%) was obtained.

Step 9: Synthesis of 2-(bromomethyl)-5-(tert-butyldimethylsilyloxy)-6-methoxybenzo[d]thiazole (10)

NBS (0.690 g, 3.88 mmol) and the catalyst quantity of AIBN were added in a CCl$_4$ solution (10 mL) of 9 (1 g, 3.23 mmol) at room temperature. Philips *IR 250 W* lamp was placed at a certain distance from the reaction flask so as to maintain the reflux. The reaction mixture was refluxed for 2 hours, and, after that, diluted with dichloromethane and washed with water. The organic phase was separated and condensed. The crude product was refined by column chromatography, and 10 (0.55 g, 44%) was obtained.

Step 10: Synthesis of diethyl (5-hydroxy-6-methoxybenzo[d]thiazole-2-yl)methylphosphonate (11)

A mixture of 10 (0.55 g, 1.4 mmol) and triethyl phosphite (0.23 g, 1.4 mmol) was heated to 100° C. for 2 hours. The crude product was refined by column chromatography, and 11 (0.31 g, 65%) was obtained.

Step 11: Synthesis of 6-methoxy-2((1E,3E)-4-(4-nitrophenyl)buta-1,3-dienyl)benz[d]thiazole-5-ol (12)

Sodium methoxide (0.1 g, 1.86 mmol) was added in a stirred DMF solution (3 mL) of 11 (0.33 g, 0.99 mmol) at 0° C., and the resultant solution was stirred for 30 minutes at the same temperature. (4-nitrophenyl) acrylic aldehyde (0.11 g, 0.62 mmol) was added to this, and the resultant solution was stirred for 30 minutes. The reaction was quenched with water, and acidified with citric acid. After that, the reaction mixture was extracted with EtOAc. The combined organic phase was condensed to dryness, and 12 (210 mg) was obtained. Without refining, the step moved on to the next step.

Step 12: Synthesis of 2-((1E,3E)-4-(4-aminophenyl)buta-1,3-dienyl)-6-methoxybenzo[d]thiazole-5-o 1 (Core1-4)

A EtOH liquid mixture (10 mL) of 12 (0.55 g, 1.6 mmol), iron powder (0.73 g, 12.8 mmol) and a saturated NH$_4$Cl solution (2 mL) was heated to 80° C. for 1 hour. After that, the reacting mass was cooled, and filtered through a celite bed. The filtrate was condensed, the resulting residue was diluted with water, and the reaction mixture was extracted with EtOAc. The organic phase was condensed to dryness, and 450 mg of Core1-4 was obtained. 180 mg of that was applied to preparative HPLC, and Core1-4 (73 mg) was obtained.

Core1-4: $^1$H NMR (400 MHz, DMSO-d$_6$) δ 7.55 (s, 1H), 7.39 (d, J=8.0 Hz, 2H), 7.31-7.20 (m, 2H), 7.04-6.77 (m, 5H), 4.8 (bs, 1H) 3.94 (s, 3H).

Synthesis Embodiment 13

Synthesis of N-(4-((1E,3E)-4-(5,6-dimethoxybenzo[d]thiazole-2-yl)buta-1,3-dienypphenyl) acetamide (Core1-5)

Core1-5 was synthesized according to the following synthesis scheme.

Synthesis Scheme

[Formula 51]

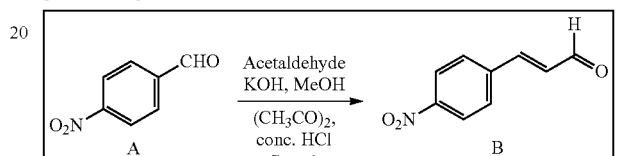

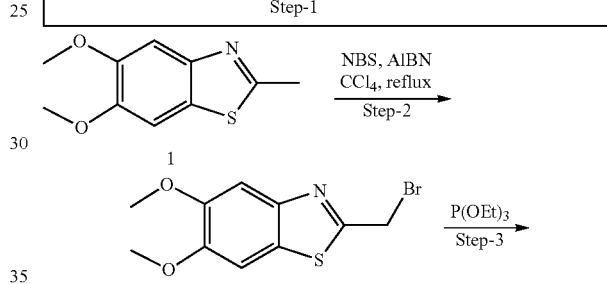

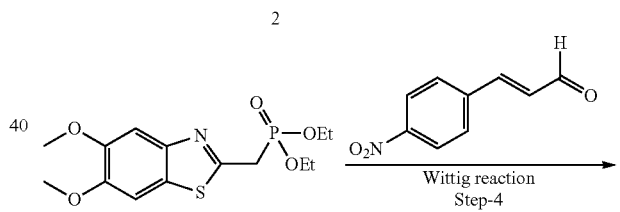

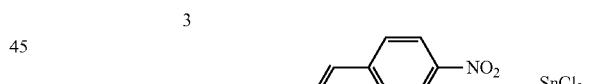

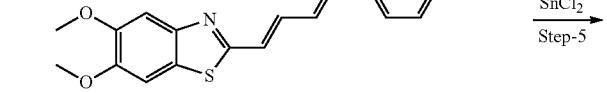

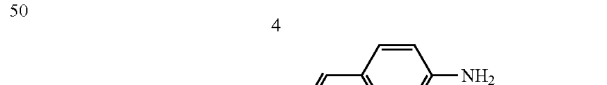

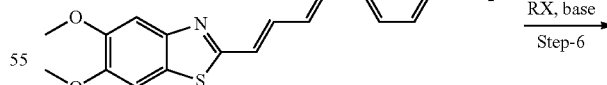

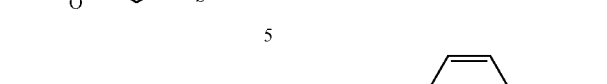

CORE 1-5

Step 1: Synthesis of (E)-3-(4-nitrophenyl)acrylic aldehyde (B)

To a liquid mixture of 4-nitrobenzaldehyde (25 g, 165 mmol) and acetaldehyde (50 mL, 900 mmol), a 20% potassium hydroxide MeOH solution (6 mL) was added dropwise at 0° C. to −5° C., until an alkaline reaction was achieved. The reaction liquid was stirred at the same temperature until the reaction mixture solidified. Acetic anhydride (80 mL) was added to this, and the mixture was heated for 30 minutes at 100° C. After that, the solution was poured in warm water (500 mL), and concentrated HCl (32 mL) was added thereto. The resulting mixture was heated at 100° C. for 20 minutes. The resulting mixture was allowed to stand overnight, and the crystals were collected by filtering and washed with water, and B (20 g, 68%) was obtained.

Step 2: Synthesis of 2-(bromomethyl)-5,6-dimethoxybenzo[d]thiazole (2)

NBS (5.11 g, 28.7 mmol) and the catalyst quantity of AIBN were added in a $CCl_4$ solution (50 mL) of 1 (5 g, 23.9 mmol) at room temperature. Philips *IR 250 W* lamp was placed at a certain distance from the reaction flask so as to maintain the reflux. The reaction mixture was refluxed for 2 hours, and, after that, diluted with dichloromethane, and washed with water. The organic phase was separated and condensed. The crude product was refined, and 2 (3.0 g, 43%) was obtained.

Step 3: Synthesis of diethyl (5,6-dimethoxybenzo[d]thiazole-2-yl)methylphosphonate (3)

A mixture of 2 (3 g, 10.46 mmol) and triethyl phosphite (2 g, 11.45 mmol) was heated to 100° C. for 2 hours. The crude product was refined by column chromatography, and 3 (3.3 g, 92%) was obtained.

Step 4: Synthesis of 5,6-dimethoxy-2-((1E,3E)-4-(4-nitrophenyl)buta-1,3-dienyl)benz[d]thiazole (4)

Sodium methoxide (0.085 g, 1.6 mmol) was added in a stirred DMF solution (3 mL) of 3 (0.30 g, 0.85 mmol) at 0° C., and the resultant solution was stirred at the same temperature for 30 minutes. (4-nitrophenyl)acrylic aldehyde (0.14 g, 0.79 mmol) was added to this, and the resultant mixture was stirred for 30 minutes. The reaction was quenched with water, and acidified with citric acid. After that, the reaction liquid mixture was extracted with EtOAc, the combined organic phase was condensed, and refined by column chromatography, and 4 (0.21 g, 65%) was obtained.

Step 5: Synthesis of 4-((1E,3E)-4-(5,6-dimethoxybenzo[d]thiazole-2-yl)buta-1,3-dienyl)aniline (5)

Iron powder (0.06 g, 1.1 mmol) and a saturated ammonium chloride aqueous solution (1 mL) were added in an EtOH solution (1 mL) of 4 (0.05 g, 0.13 mmol). The reaction mixture was refluxed for 30 minutes. After that, the reacting mass was cooled and filtered through a celite bed. The filtrate was condensed to dryness, and 5 (40 mg, 88%) was obtained.

Step 6: Synthesis of N-(4-((1E,3E)-4-(5,6-dimethoxybenzo[d]thiazole-2-yl)buta-1,3-dieneyl)phenyl)acetamide (Core1-5)

Triethylamine (0.037 g, 0.37 mmol) and acetic anhydride (0.029 g, 0.37 mmol) were added in a dichloromethane solution (2 mL) of 5 (0.05 g, 0.15 mmol). The reaction liquid mixture was stirred at room temperature for 1 hour. The reaction liquid mixture was diluted with water and extracted with dichloromethane. The combined organic phase was condensed and refined by preparative HPLC, and Core1-5 (0.02 g, 36%) was obtained.

Core1-5: $^1$H-NMR (400 MHz, choloroform-d) δ 7.60-6.74 (m, 10H), 3.98 (s, 6H), 2.21 (s, 3H).

Synthesis Embodiment 14

Synthesis of 3-(4-((1E,3E)-4-(5,6-dimethozybenzo[d]thiazole-2-yl)buta-1,3-dienyl)phenylamino)propan-1-ol (Core1-11)

Core1-11 was synthesized according to the following synthesis scheme.

Synthesis Scheme

[Formula 52]

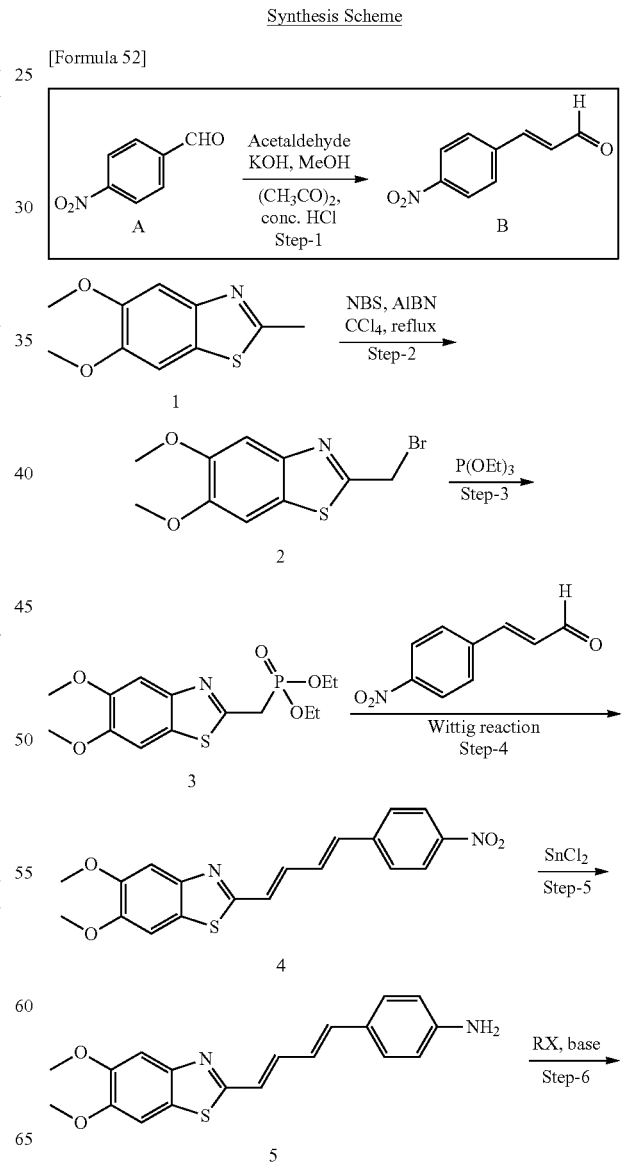

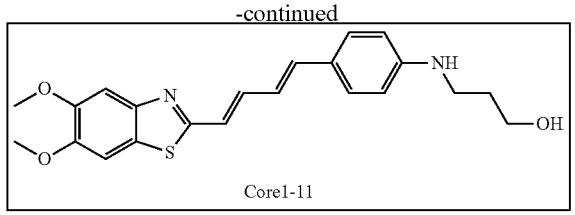

Step 1: Synthesis of (E)-3-(4-nitrophenyl)acrylic aldehyde (B)

A 20% potassium hydroxide MeOH solution (6 mL) was added dropwise to a liquid mixture of 4-nitrobenzaldehyde (25 g, 165 mmol) and acetaldehyde (50 mL, 900 mmol), at 0° C. to −5° C., until an alkaline reaction was achieved. The reaction liquid was stirred at the same temperature until the reaction mixture solidified. Acetic anhydride (80 mL) was added to this, and the mixture was heated for 30 minutes at 100° C. After that, the solution was poured in warm water (500 mL), and concentrated HCl (32 mL) was added thereto. The resulting mixture was heated at 100° C. for 20 minutes. The resulting mixture was allowed to stand overnight, the crystals were collected by filtering and washed with water, and B (20 g, 68%) was obtained.

Step 2: Synthesis of 2-(bromomethyl)-5,6-dimethoxybenzo[d]thiazole (2)

NBS (5.11 g, 28.7 mmol) and the catalyst quantity of AIBN were added in a CCl$_4$ solution (50 mL) of 1 (5 g, 23.9 mmol) at room temperature. Philips *IR 250 W* lamp was placed at a certain distance from the reaction flask so as to maintain the reflux. The reaction mixture was refluxed for 2 hours, and, after that, diluted with dichloromethane and washed with water. The organic phase was separated and condensed. The crude product was refined, and 2 (3.0 g, 43%) was obtained.

Step 3: Synthesis of diethyl (5,6-dimethoxybenzo[d]thiazole-2-yl)methylphosphonate (3)

A mixture of 2 (3 g, 10.46 mmol) and triethyl phosphite (2 g, 11.45 mmol) was heated to 100° C. for 2 hours. The crude product was refined by column chromatography, and 3 (3.3 g, 92%) was obtained.

Step 4: Synthesis of 5,6-dimethoxy-2-((1E,3E)-4-(4-nitrophenyl)buta-1,3-dienyl)benz[d]thiazole (4)

Sodium methoxide (0.085 g, 1.6 mmol) was added in a stirred DMF solution (3 mL) of 3 (0.30 g, 0.85 mmol) at 0° C., and the resultant solution was stirred at the same temperature for 30 minutes. To this, (4-nitrophenyl)acrylic aldehyde (0.14 g, 0.79 mmol) was added, and the resultant solution was stirred for 30 minutes. The reaction was quenched with water, and acidified with citric acid. After that, the reaction liquid mixture was extracted with EtOAc, the combined organic phase was condensed, the crude product was refined by column chromatography, and 4 (0.21 g, 65%) was obtained.

Step 5: Synthesis of 4-((1E,3E)-4-(5,6-dimethoxybenzo[d]thiazole-2-yl)buta-1,3-dienyl)aniline (5)

Iron powder (0.06 g, 1.1 mmol) and a saturated ammonium chloride aqueous solution (1 mL) were added in an EtOH solution (1 mL) of 4 (0.05 g, 0.13 mmol). The reaction mixture was refluxed for 30 minutes. After that, the reacting mass was cooled, and filtered through celite bed. The filtrate was condensed to dryness, and 5 (40 mg, 88%) was obtained.

Step 6: Synthesis of 3-(4-((1E,3E)-4-(5,6-dimethoxybenzo[d]thiazole-2-yl)buta-1,3-diene-1-yl)phenylamino)propan-1-ol (Core1-11)

Triethylamine (0.22 g, 2.21 mmol) and 3-bromo-1-propanol (0.3 g, 2.21 mmol) were added in a dichloromethane solution (10 mL) of 5 (0.3 g, 0.88 mmol). The reaction liquid mixture was stirred at room temperature for 1 hour. The reaction liquid mixture was diluted with water, and extracted with dichloromethane. The combined organic phase was condensed and refined by preparative HPLC, and Core1-11 (0.06 g, 17%) was obtained.

Core1-11: NMR (400 MHz, DMSO-d6) δ 7.59 (s, 1H), 7.45 (s, 1H), 7.36-7.17 (m, 3H), 6.91-6.79 (m, 3H), 6.60 (d, J=8.3 Hz, 2H), 3.84 (d, J=2.0 Hz, 6H), 3.50 (t, J 6.2, 6.2 Hz, 2H), 3.11 (t, J=7.0, 7.0 Hz, 2H), 1.70 (m, 2H).

Synthesis Embodiment 15

Synthesis of 4-((1E,3E)-4-(5,6-dimethoxybenzo[d]thiazole-2-yl)buta-1,3-dienyl)-N-isopropylaniline (Core1-15)

Core1-15 was synthesized according to the following synthesis scheme:

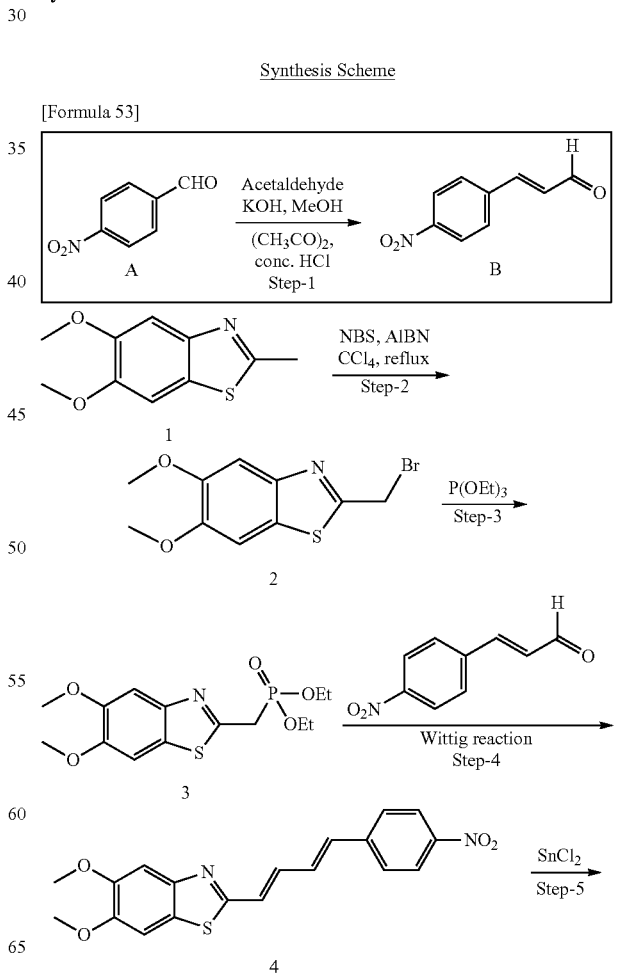

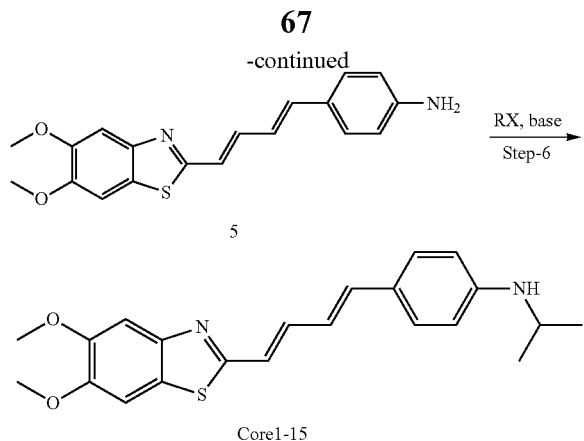

Step 1: Synthesis of (E)-3-(4-nitrophenyl)acrylic aldehyde(B)

A 20% potassium hydroxide MeOH solution (6 mL) was added dropwise in a liquid mixture of 4-nitrobenzaldehyde (25 g, 165 mmol) and acetaldehyde (50 mL, 900 mmol), at 0° C. to −5° C., until an alkaline reaction was achieved. The reaction liquid was stirred at the same temperature until the reaction mixture solidified. Acetic anhydride (80 mL) was added to this, and the mixture was heated for 30 minutes at 100° C. After that, the solution was poured in warm water (500 mL), and concentrated HCl (32 mL) was added thereto. The resulting mixture was heated at 100° C. for 20 minutes. The resulting mixture was allowed to stand overnight, the crystals were collected by filtering and washed with water, and B (20 g, 68%) was obtained.

Step 2: Synthesis of 2-(bromomethyl)-5,6-dimethoxybenzo[d]thiazole (2)

NBS (5.11 g, 28.7 mmol) and the catalyst quantity of AIBN were added in a CCl$_4$ solution (50 mL) of 1 (5 g, 23.9 mmol) at room temperature. Philips *IR 250 W* lamp was placed at a certain distance from the reaction flask so as to maintain the reflux. The reaction mixture was refluxed for 2 hours, and, after that, diluted with dichloromethane and washed with water. The organic phase was separated and condensed. The crude product was refined, and 2 (3.0 g, 43%) was obtained.

Step 3: Synthesis of diethyl(5,6-dimethoxybenzo[d]thiazole-2-yl)methylphosphonate (3)

A mixture of 2 (3 g, 10.46 mmol) and triethyl phosphite (2 g, 11.45 mmol) was heated to 100° C. for 2 hours. The crude product was refined by column chromatography, and 3 (3.3 g, 92%) was obtained.

Step 4: Synthesis of 5,6-dimethoxy-2-((1E,3E)-4-(4-nitrophenyl)buta-1,3-dienyl)benz[d]thiazole (4)

Sodium methoxide (0.085 g, 1.6 mmol) was added in a stirred DMF solution (3 mL) of 3 (0.30 g, 0.85 mmol) at 0° C., and the resultant solution was stirred at the same temperature for 30 minutes. (4-nitrophenyl)acrylic aldehyde (0.14 g, 0.79 mmol) was added to this, and the resultant mixture was stirred for 30 minutes. The reaction was quenched with water, and acidified with citric acid. After that, the reaction liquid mixture was extracted with EtOAc, the combined organic phase was condensed and refined by column chromatography, and 4 (0.21 g, 65%) was obtained.

Step 5: Synthesis of 4-((1E,3E)-4-(5,6-dimethoxybenzo[d]thiazole-2-yl)buta-1,3-dienyl)aniline (5)

Iron powder (0.06 g, 1.1 mmol) and a saturated ammonium chloride aqueous solution (1 mL) were added in an EtOH solution (1 mL) of 4 (0.05 g, 0.13 mmol). The reaction mixture was refluxed for 30 minutes. After that, the reacting mass was cooled, and filtered through a celite bed. The filtrate was condensed to dryness, and 5 (40 mg, 88%) was obtained.

Step 6: Synthesis of 4-((1E,3E)-4-(5,6-dimethoxybenzo[d]thiazole-2-yl)buta-1,3-diene-1-yl)-N-isopropylaniline (Core1-15)

Triethylamine (0.037 g, 0.37 mmol) and 2-bromopropane (0.045 g, 0.37 mmol) were added in a dichloromethane solution (2 mL) of 5 (0.05 g, 0.15 mmol). The reaction liquid mixture was stirred at room temperature for 1 hour. The reaction liquid mixture was diluted with water, and extracted with dichloromethane. The combined organic phase was condensed and refined by preparative HPLC, and Core1-15 (0.023 g, 41%) was obtained.

Core1-15: NMR (400 MHz, DMSO-d$_6$) δ 7.72-7.17 (m, 7H), 7.10-6.55 (m, 6H), 5.76 (s, 1H), 3.84 (s, 6H), 1.23 (m, 1H) 1.16 (dd, J=6.1, 3.3 Hz, 6H).

Synthesis Embodiment 16

Synthesis of 4-((1E,3E)-4-(5,6-dimethoxybenzo[d]thiazole-2-yl)buta-1,3-dienyl)-N-(hepta-1,6-diene-4-yl)aniline (Core1-20)

Core1-20 was synthesized according to the following synthesis scheme:

Synthesis Scheme

[Formula 54]

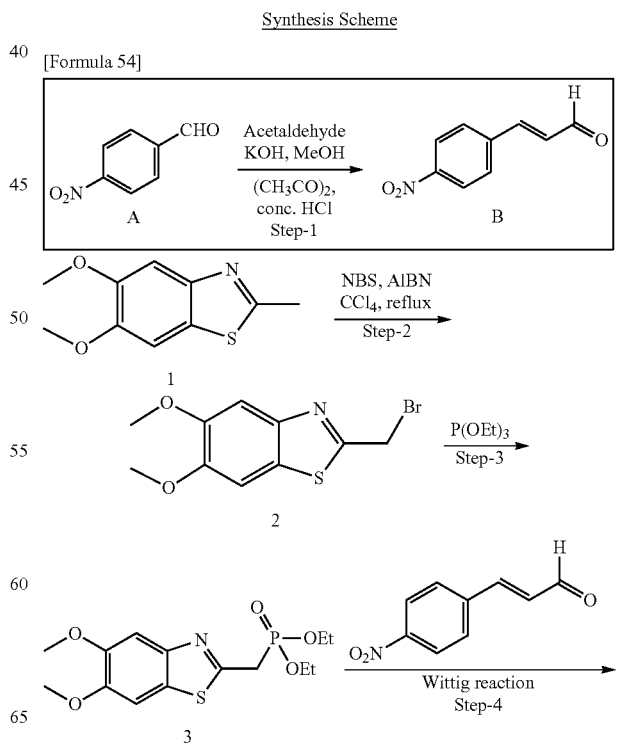

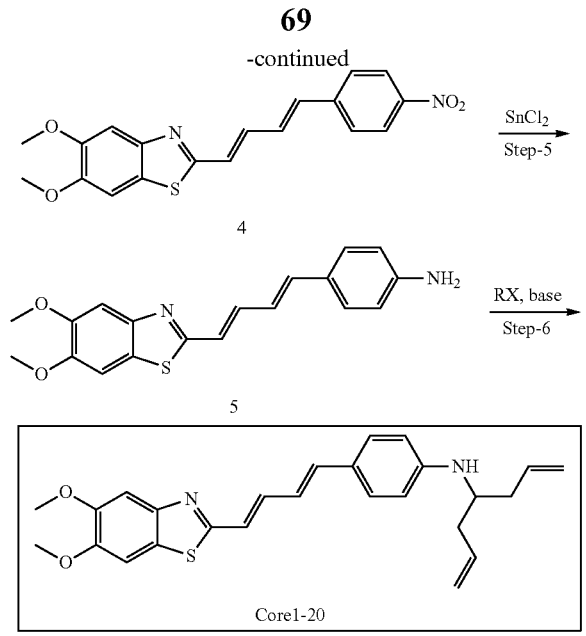

Step 1: Synthesis of (E)-3-(4-nitrophenyl)acrylic aldehyde (B)

A 20% potassium hydroxide MeOH solution (6 mL) was added dropwise in a liquid mixture of 4-nitrobenzaldehyde (25 g, 165 mmol) and acetaldehyde (50 mL, 900 mmol), at 0° C. to −5° C., until an alkaline reaction was achieved. The reaction liquid was stirred at the same temperature until the reaction mixture solidified. Acetic anhydride (80 mL) was added to this, and the mixture was heated for 30 minutes at 100° C. After that, the solution was poured in warm water (500 mL), and concentrated HCl (32 mL) was added. The resulting mixture was heated at 100° C. for 20 minutes. The resulting mixture was allowed to stand overnight, the crystals were collected by filtering and washed with water, and B (20 g, 68%) was obtained.

Step 2: Synthesis of 2-(bromomethyl)-5,6-dimethoxybenzo[d]thiazole (2)

NBS (5.11 g, 28.7 mmol) and the catalyst quantity of AIBN were added in a $CCl_4$ solution (50 mL) of 1 (5 g, 23.9 mmol) at room temperature. A Philips *IR 250 W* lamp was placed at a certain distance from the reaction flask so as to maintain the reflux. The reaction mixture was refluxed for 2 hours, and, after that, diluted with dichloromethane and washed with water. The organic phase was separated and condensed. The crude product was refined, and 2 (3.0 g, 43%) was obtained.

Step 3: Synthesis of diethyl (5,6-dimethoxybenzo[d]thiazole-2-yl)methylphosphonate (3)

A mixture of 2 (3 g, 10.46 mmol) and triethyl phosphite (2 g, 11.45 mmol) was heated to 100° C. for 2 hours. The crude product was refined by column chromatography, and 3 (3.3 g, 92%) was obtained.

Step 4: Synthesis of 5,6-dimethoxy-2-((1E,3E)-4-(4-nitrophenyl)buta-1,3-dienyl)benz[d]thiazole (4)

Sodium methoxide (0.085 g, 1.6 mmol) was added in a stirred DMF solution (3 mL) of 3 (0.30 g, 0.85 mmol) at 0° C., and the resultant solution was stirred at the same temperature for 30 minutes. (4-nitrophenyl)acrylic aldehyde (0.14 g, 0.79 mmol) was added to this, and the resulting solution was stirred for 30 minutes. The reaction was quenched with water, and acidified with citric acid. After that, the reaction liquid mixture was extracted with EtOAc, the combined organic phase was condensed and refined by column chromatography, and 4 (0.21 g, 65%) was obtained.

Step 5: Synthesis of 4-((1E,3E)-4-(5,6-dimethoxy-benzo[d]thiazole-2-yl)buta-1,3-dienyl)aniline (5)

Iron powder (0.06 g, 1.1 mmol) and a saturated ammonium chloride aqueous solution (1 mL) were added in an EtOH solution (1 mL) of 4 (0.05 g, 0.13 mmol). The reaction mixture was refluxed for 30 minutes. After that, the reacting mass was cooled and filtered through a celite bed. The filtrate was condensed to dryness, and 5 (40 mg, 88%) was obtained.

Step 6: Synthesis of 4-((1E,3E)-4-(5,6-dimethoxy-benzo[d]thiazole-2-yl)buta-1,3-diene-1-yl)-N-(hepta-1,6-diene-4-yl)aniline (Core1-20)

Triethylamine (0.037 g, 0.37 mmol) and allyl bromide (0.044 g, 0.37 mmol) were added in a dichloromethane solution (2 mL) of 5 (0.05 g, 0.15 mmol). The reaction liquid mixture was stirred at room temperature for 1 hour. The reaction liquid mixture was diluted with water and extracted with dichloromethane. The combined organic phase was condensed and refined by preparative HPLC, and Core1-20 (0.026 g, 41.2%) was obtained.

Core1-20 $^1$H NMR (400 MHz, DMSO-$d_6$) δ 7.59-7.18 (m, 5H), 6.93-6.81 (m, 3H), 6.68 (d, J=8.6 Hz, 2H), 5.86 (m, 2H), 5.24-5.06 (m, 4H), 3.97 (d, J=5.2 Hz, 4H), 3.84 (d, J=2.1 Hz, 6H).

Synthesis Embodiment 17) (Synthesis of N-(5-((1E,3E)-4-(5,6-dimethozybenzo[d]thiazole-2-yl)buta-1,3-dienyl)pyridine-2-yl)acetamide (Core2-9)

Core2-9 was synthesized according to the following synthesis scheme:

Synthesis Scheme

[Formula 55]

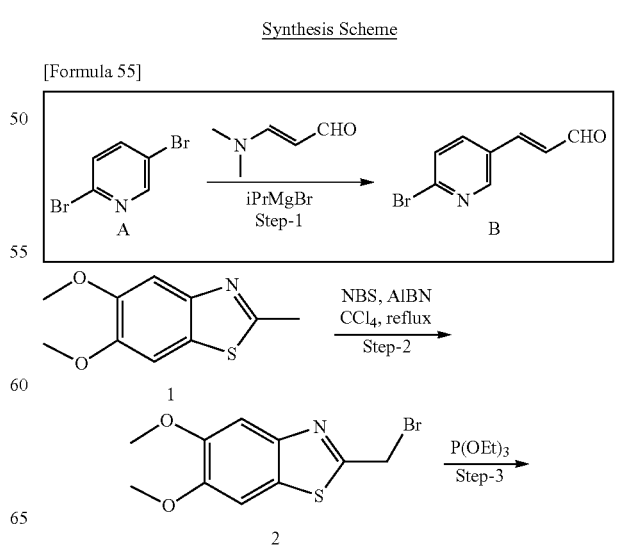

-continued

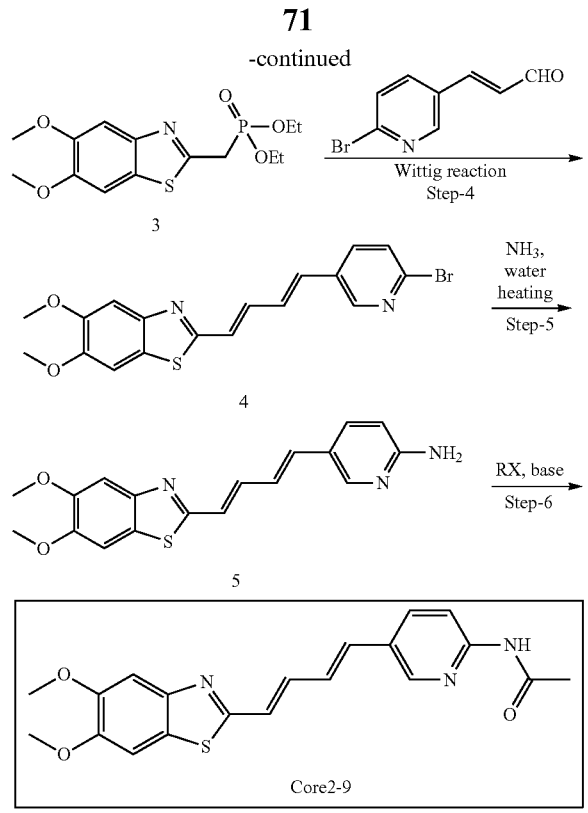

Step 1: Synthesis of (E)-3-(6-bromopyridine-3-yl) acrylic aldehyde(B)

In a THF solution (5 mL) of 2,5-dibromopyridine (2.37 g, 10 mmol), 2-propylmagnesiumchloride (in THF, 2.0 M, 5 mL, 10 mmol) was added at room temperature. The resulting suspension was stirred for 1 hour, and, after that, cooled down to 0° C. 3-dimethylaminoacrolein (1.3 mL, 12.36 mmol) was added, and the mixture was warmed to room temperature and stirred for 2 hours. The reaction was finished by adding ice at 0° C., and acidified with 2N HCl. After that, the resultant mixture was diluted with EtOAc and washed with water. The organic phase was separated and condensed. The crude product was refined, and B (0.45 g, 21%) was obtained.

Step 2: Synthesis of 2-(bromomethyl)-5,6-dimethoxybenzo[d]thiazole (2)

NBS (5.11 g, 28.7 mmol) and the catalyst quantity of AIBN were added in a $CCl_4$ solution (50 mL) of 1 (5 g, 23.9 mmol) at room temperature. Philips *IR 250 W* lamp was placed at a certain distance from the reaction flask so as to maintain the reflux. The reaction mixture was refluxed for 2 hours, and, after that, diluted with dichloromethane, and washed with water. The organic phase was separated and condensed. The crude product was refined, and 2 (3.0 g, 43%) was obtained.

Step 3: Synthesis of diethyl (5,6-dimethoxybenzo[d]thiazole-2-yl)methylphosphonate (3)

A mixture of 2 (3 g, 10.46 mmol) and triethyl phosphite (2 g, 11.45 mmol) was heated to 100° C. for 2 hours. The crude product was refined by column chromatography, and 3 (3.3 g, 92%) was obtained.

Step 4: Synthesis of 2-((1E,3E)-4-(6-bromopyridine-3-yl)buta-1,3-dienyl)-5,6-dimethoxybenzo[d]thiazole (4)

Sodium methoxide (0.10 g, 1.96 mmol) was added in a stirred DMF solution (5 mL) of 3 (0.50 g, 1.44 mmol) at 0° C., and was stirred at the same temperature for 30 minutes. B (0.27 g, 1.3 mmol) was added to this, and the resultant mixture was stirred for 30 minutes, and the reaction was quenched with water and acidified with citric acid. After that, the reaction mixture was extracted with EtOAc, the combined organic phase was condensed and refined by column chromatography, and 4 (0.512 g, 85%) was obtained.

Step 5: Synthesis of 5-((1E,3E)-4-(5,6-dimethoxybenzo[d]thiazole-2-yl)buta-1,3-diene-1-yl)pyridine-2-amine (5)

A mixture of 4 (0.5 g, 1.24 mmol) and ammonia water (10 mL) was put in a sealed tube, and the reaction mixture was refluxed for 4 hours. The reaction mixture was condensed and refined by column chromatography, and 5 (0.2 g, 47.6%) was obtained.

Step 6: Synthesis of N-(5-((1E,3E)-4-(5,6-dimethoxybenzo[d]thiazole-2-yl)buta-1,3-diene-1-yl)pyridine-2-yl)acetamide (Core2-9)

Triethylamine (0.148 g, 1.47 mmol) and acetic anhydride (0.15 g, 1.47 mmol) were added in a dichloromethane solution (10 mL) of 5 (0.2 g, 0.589 mmol). The reaction liquid mixture was stirred at room temperature for 1 hour. The reaction liquid mixture was diluted with water and extracted with dichloromethane. The combined organic phase was condensed and refined by preparative HPLC, and Core2-9 (0.04 g, 18%) was obtained.

Core2-9: $^1$H NMR (400 MHz, DMSO-$d_6$) δ 10.62 (s, 1H), 8.45 (s, 1H), 8.09 (d, J=8.7 Hz, 1H), 8.00 (dd, J=8.7, 2.3 Hz, 1H), 7.63 (s, 1H), 7.49 (s, 1H), 7.38-7.16 (m, 2H), 6.98 (m, 2H), 3.85 (s, 6H), 2.10 (s, 3H).

Synthesis Embodiment 18

Synthesis of 3-(5-((1E,3E)-4-(5,6-dimethoxybenzo[d]thiazole-2-yl)buta-1,3-dienyl)pyridine-2-ylamino)propan-1-ol (Core2-10)

Core2-10 was synthesized according to the following synthesis scheme:

Synthesis Scheme

[Formula 56]

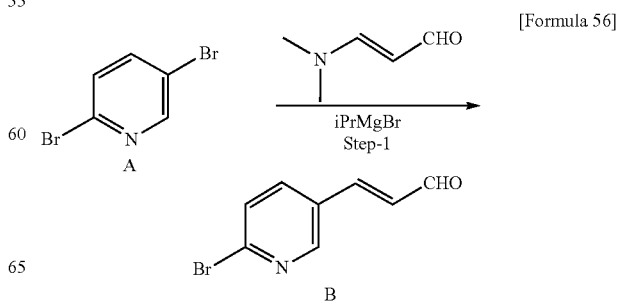

Step 3: Synthesis of diethyl(5,6-dimethoxybenzo[d]thiazole-2-yl)methylphosphonate (3)

A mixture of 2 (3 g, 10.46 mmol) and triethyl phosphite (2 g, 11.45 mmol) was heated to 100° C. for 2 hours. The crude product was refined by column chromatography, and 3 (3.3 g, 92%) was obtained.

Step 4: Synthesis of 2-((1E,3E)-4-(6-bromopyridine-3-yl)buta-1,3-dienyl)-5,6-dimethoxybenzo[d]thiazole (4)

Sodium methoxide (0.10 g, 1.96 mmol) was added in a stirred DMF solution (5 mL) of 3 (0.50 g, 1.44 mmol) at 0° C., and the resultant solution was stirred at the same temperature for 30 minutes. B (0.27 g, 1.3 mmol) was added to this, the resultant solution was stirred for 30 minutes, and the reaction was quenched with water and acidified with citric acid. After that, the reaction mixture was extracted with EtOAc, the combined organic phase was condensed and refined by column chromatography, and 4 (0.512 g, 85%) was obtained.

Step 5: Synthesis of 3-(5-((1E,3E)-4-(5,6-dimethoxybenzo[d]thiazole-2-yl)buta-1,3-dienyl)pyridin-2-ylamino)propan-1-ol (Core2-10)

In a sealed tube, a DMF liquid mixture (5 mL) of 4 (0.2 g, 0.49 mmol), 3-aminopropanol (0.3 g, 4.96 mmol) and triethylamine (0.25 g, 2.48 mmol) was stirred, at 120° C., for 16 hours. The reaction mixture was diluted with water, refined by preparative HPLC, and Core2-10 (0.04 g, 20%) was obtained.

Core2-10: $^1$H NMR (400 MHz, chloroform-d) δ 9.87 (s, 1H), 8.03 (d, J=9.7 Hz, 1H), 7.81 (s, 1H), 7.56 (s, 1H), 7.23 (d, J=13.9 Hz, 2H), 7.09 (d, J=15.4 Hz, 1H), 6.90 (m, 2H), 6.66 (d, J=15.5 Hz, 1H), 3.99 (d, J=2.5 Hz, 6H), 3.82 (t, J=5.8, 5.8 Hz, 2H), 3.53 (t, J=6.7, 6.7 Hz, 2H), 1.97 (m, 2H).

Synthesis Embodiment 19) (Synthesis of N,N-diallyl-5-((1E,3E)-4-(5,6-dimethoxybenzo[d]thiazole-2-yl)buta-1,3-dienyl)pyridine-2-amine (Core2-14)

Core2-14 was synthesized according to the following synthesis scheme:

Step 1: Synthesis of (E)-3-(6-bromopyridine-3-yl)acrylic aldehyde (B)

In a THF solution (5 mL) of 2,5-dibromopyridine (2.37 g, 10 mmol), 2-propylmagnesiumchloride (in THF, 2.0 M, 5 mL, 10 mmol) was added at room temperature. The resulting suspension was stirred for 1 hour, and, after that, cooled down to 0° C. 3-dimethylaminoacrolein (1.3 mL, 12.36 mmol) was added, and the mixture was warmed to room temperature and stirred for 2 hours. The reaction was finished by adding ice at 0° C., and acidified with 2N HCl. After that, the resultant mixture was diluted with EtOAc and washed with water. The organic phase was separated and condensed. The crude product was refined, and B (0.45 g, 21%) was obtained.

Step 2: Synthesis of 2-(bromomethyl)-5,6-dimethoxybenzo[d]thiazole (2)

NBS (5.11 g, 28.7 mmol) and the catalyst quantity of AIBN were added in a CCl$_4$ solution (50 mL) of 1 (5 g, 23.9 mmol) at room temperature. Philips *IR 250 W* lamp was placed at a certain distance from the reaction flask so as to maintain the reflux. The reaction mixture was refluxed for 2 hours, and, after that, diluted with dichloromethane, and washed with water. The organic phase was separated and condensed. The crude product was refined, and 2 (3.0 g, 43%) was obtained.

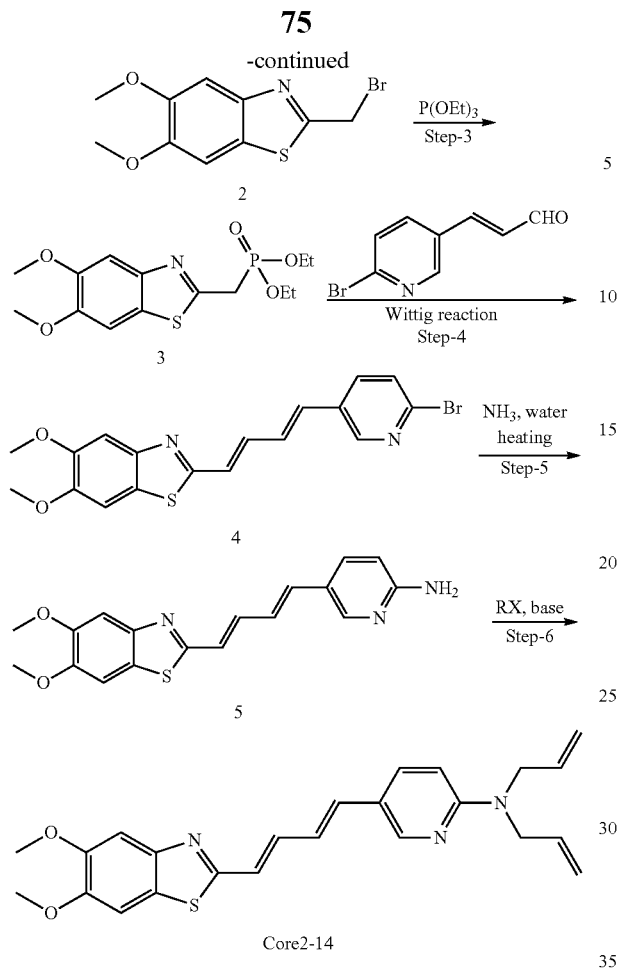

Step 1: Synthesis of (E)-3-(6-bromopyridine-3-yl) acrylic aldehyde (B)

In a THF solution (5 mL) of 2,5-dibromopyridine (2.37 g, 10 mmol), 2-propylmagnesiumchloride/chloride (in THF, 2.0 M, 5 mL, 10 mmol) was added at room temperature. The resulting suspension was stirred for 1 hour, and, after that, cooled down to 0° C. 3-dimethylaminoacrolein (1.3 mL, 12.36 mmol) was added, and the mixture was warmed to room temperature and stirred for 2 hours. The reaction was finished by adding ice at 0° C., and acidified with 2N HCl. After that, the resultant mixture was diluted with EtOAc, and washed with water. The organic phase was separated and condensed. The crude product was refined, and B (0.45 g, 21%) was obtained.

Step 2: Synthesis of 2-(bromomethyl)-5,6-dimethoxybenzo[d]thiazole (2)

NBS (5.11 g, 28.7 mmol) and the catalyst quantity of AIBN were added in a $CCl_4$ solution (50 mL) of 1 (5 g, 23.9 mmol) at room temperature. Philips *IR 250 W* lamp was placed at a certain distance from the reaction flask so as to maintain the reflux. The reaction mixture was refluxed for 2 hours, and, after that, diluted with dichloromethane and washed with water. The organic phase was separated and condensed. The crude product was refined, and 2 (3.0 g, 43%) was obtained.

Step 3: Synthesis of diethyl (5,6-dimethoxybenzo[d]thiazole-2-yl)methylphosphonate (3)

A mixture of 2 (3 g, 10.46 mmol) and triethyl phosphite (2 g, 11.45 mmol) was heated to 100° C. for 2 hours. The crude product was refined by column chromatography, and 3 (3.3 g, 92%) was obtained.

Step 4: Synthesis of 2-((1E,3E)-4-(6-bromopyridine-3-yl)buta-1,3-dienyl)-5,6-dimethoxybenzo[d]thiazole (4)

Sodium methoxide (0.10 g, 1.96 mmol) was added in a stirred DMF solution (5 mL) of 3 (0.50 g, 1.44 mmol) at 0° C., and the resultant solution was stirred at the same temperature for 30 minutes. B (0.27 g, 1.3 mmol) was added to this, and the resultant mixture was stirred for 30 minutes, and the reaction was quenched with water and acidified with citric acid. After that, the reaction mixture was extracted with EtOAc, the combined organic phase was condensed and refined by column chromatography, and 4 (0.512 g, 85%) was obtained.

Step 5: Synthesis of 5-((1E,3E)-4-(5,6-dimethoxybenzo[d]thiazole-2-yl)buta-1,3-diene-1-yl)pyridine-2-amine (5)

A mixture of 4 (0.5 g, 1.24 mmol) and ammonia water (10 mL) was put in a sealed tube, and the reaction mixture was refluxed for 4 hours. The reaction mixture was condensed and refined by column chromatography, and 5 (0.2 g, 47.6%) was obtained.

Step 6: Synthesis of N,N-diallyl-5-((1E,3E)-4-(5,6-dimethoxybenzo[d]thiazole-2-yl)buta-1,3-diene-1-yl)pyridine-2-amine (Core1-14)

Triethylamine (0.148 g, 1.47 mmol) and allyl bromide (0.18 g, 1.47 mmol) were added in a dichloromethane solution (10 mL) of 5 (0.2 g, 0.589 mmol). The reaction liquid mixture was stirred at room temperature for 1 hour. The reaction liquid mixture was diluted with water and extracted with dichloromethane. The combined organic phase was condensed and refined by preparative HPLC, and Core2-14 (0.03 g, 12%) was obtained.

Core2-14: $^1$H NMR (400 MHz, DMSO-$d_6$) δ 8.16 (d, J=2.5 Hz, 1H), 7.93-7.85 (m, 1H), 7.61 (s, 1H), 7.47 (s, 1H), 7.26 (dd, J=15.3, 10.6 Hz, 1H), 7.04 (dd, J=15.5, 10.6 Hz, 1H), 6.95-6.69 (m, 3H), 5.86 (m, 2H), 5.21-5.13 (m, 4H), 4.16 (d, J=5.2 Hz, 4H), 3.84 (d, J=1.8 Hz, 6H).

Synthesis Embodiment 20-1

Synthesis of 1-fluoro-2-(2-((1E,3E)-4-(6-(methylamino)pyridine-3-yl)buta-1,3-dienyl)benz[d]thiazole-6-yloxy)-2-hydroxymethyl-ethane (F0-PBB3 analog)

An F0-PBB3 analog was synthesized according to the following synthesis scheme:

Synthesis scheme

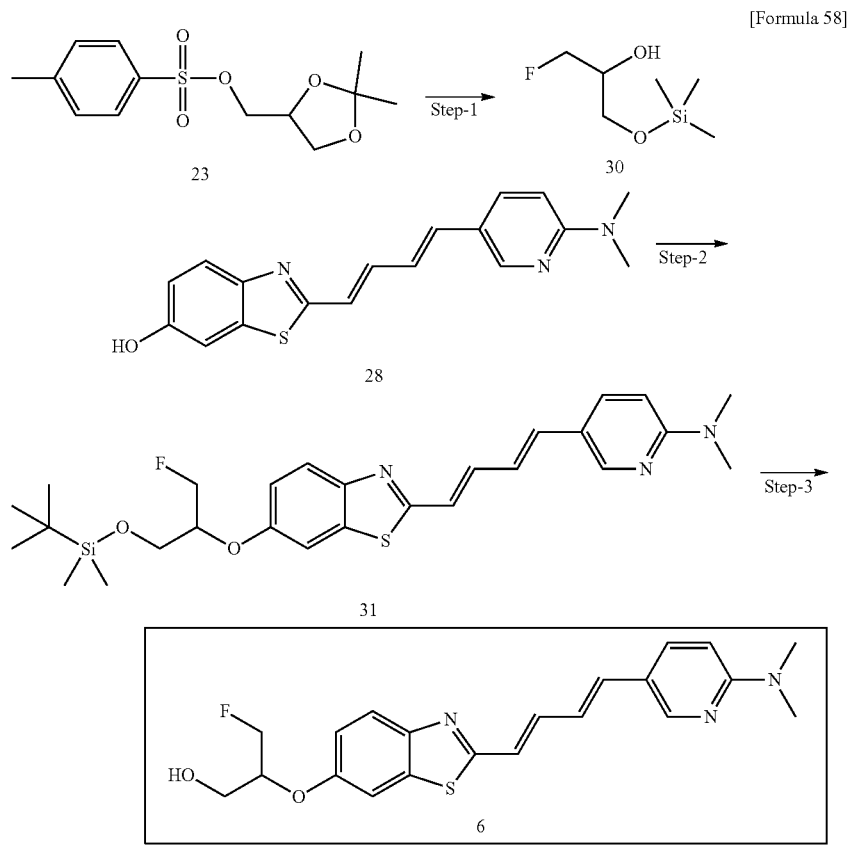

[Formula 58]

Step 1: Synthesis of Compound (30)

Under an argon atmosphere, tetrabutylammoniumfluorid (1.0M tetrahydrofuran solution, 3.15 mL, 3.15 mmol) was added to the compound (23) (819 mg, 2.86 mmol), and the resultant mixture was heated to reflux. The reaction liquid was cooled down to room temperature, added water, and extracted with diethyl ether. After the organic layer was washed with water and dried with anhydrous sodium sulphate, diethyl ether was distillated under reduced pressure. Methanol (4.3 mL) was added to the residue and the resultant mixture was cooled with ice, and, after 4N hydrochloric acid/dioxane (1.4 mL) was added thereto and the temperature was raised to room temperature, the resultant mixture was stirred all night. The reaction liquid was distillated under reduced pressure, tetrahydrofuran (4.0 mL) and imidazole (131 mg, 1.92 mmol) were added in reaction liquid, and the resultant liquid was cooled with ice. After t-butyldimethylchlorosilane (247 mg, 1.64 mmol) was added in the reaction liquid and the reaction liquid was heated to room temperature, the reaction liquid was stirred all night. The reaction liquid was added water and extracted with ethyl acetate. After the organic layer was washed with water and saturated saline water and dried with anhydrous sodium sulphate, the solvent was distillated under reduced pressure. By refining the residue by column chromatography (developing solvent: heptane/ethyl acetate=20/1→10/1), 199 mg of the title compound (30) was obtained.

Step 2: Synthesis of Compound (31)

Under an argon atmosphere, the compound (30) (180 mg, 0.86 mmol) and triphenylphosphine (226 mg, 0.86 mmol) were added in a tetrahydrofuran solution (4.3 mL) of the compound (28) (140 mg, 0.43 mmol), and the resultant solution was cooled with ice. Diisopropyl azodicarboxylate (174 mg, 0.86 mmol) was added dropwise to the reaction liquid. The reaction liquid was heated to room temperature, and, after having been stirred all night, the reaction liquid was distillated under reduced pressure. By refining the residue by column chromatography (developing solvent: heptane/ethyl acetate=5/1→1/1), 200 mg of the title compound (31) was obtained.

Step 3: Synthesis of Compound (6)

4N hydrochloric acid/dioxane (1.9 mL) was added in a tetrahydrofuran solution (5.7 mL) of the compound (31) (196 mg, 0.38 mmol), and the resultant solution was stirred. After the disappearance of the raw material, the reaction liquid was cooled with ice, and, after having been neutralized with a sodium hydrogen carbonate aqueous solution, the reaction liquid was extracted with ethyl acetate. After the organic layer was washed with water and saturated saline water and dried with anhydrous sodium sulphate, the solvent was distillated under reduced pressure. By refining the residue by column chromatography (developing solvent: heptane/ethyl acetate=2/1→1/4), 117 mg of the title compound (6) was obtained.

Compound (6): $^1$H NMR (400 MHz, DMSO-$d_6$) δ ppm: 8.20 (d, J=2.29 Hz, 1H), 7.80 (dd, J=9.16 Hz, 1.83 Hz, 2H), 7.72 (d, J=2.29 Hz, 1H), 7.30 (dd, J=15.57 Hz, 10.08 Hz, 1H), 7.14 (dd, J=8.70 Hz, 2.29 Hz, 1H), 7.01 (dd, J=15.11 Hz, 10.53 Hz, 1H), 6.91 (d, J=15.57 Hz, 1H), 6.88 (d, J=15.57 Hz, 1H), 6.70 (d, J=9.16 Hz, 1H), 5.07 (t, J=5.50 Hz, 1H), 4.55-4.85 (m, 3H), 3.63-3.68 (m, 2H), 3.07 (s, 6H).

Synthesis Embodiment 20-2

Synthesis of 1-fluoro-3-(2-((1E,3E)-4-(6-(methylamino)pyridine-3-yl)buta-1,3-dienyl)benz[d]thiazole-6-yloxy)propan-2-ol (F0-PBB3)

This can be synthesized by the same method as that of synthesis example 20-1 above.

Synthesis Embodiment 21

Synthesis of (E)-1-fluoro-3-(2-(4-(6-(methylamino)pyridine-3-yl)buta-1-en ynyl)benz[d]thiazole-6-yloxy)propan-2-ol (F0-PBB3.2)

This can be synthesized by the same method as that of synthesis example 20-1 above.

Synthesis Embodiment 22

Synthesis of 2-((1E,3E)-4-(2-fluoro-6-(methylamino)pyridine-3-yl)buta-1,3-dienyl)benz[d]thiazole-6-ol (F1-PBB3)

This can be synthesized by a similar method to that of synthesis example 20-1 above.

Synthesis Embodiment 23

Synthesis of (E)-2-(4-(2-fluoro-6-(methylamino)pyridine-3-yl)buta-1-en-3-ynyl)benz[d]thiazole-6-ol (F1-PBB3.2)

This can be synthesized by a similar method to that of synthesis example 20-1 above.

Synthesis Embodiment 24

Synthesis of 2-((1E,3E)-4-(2-fluoro-6-(methylamino)pyridine-3-yl)buta-1,3-dienyl)benzofuran-5-ol (F1-PBBf3)

This can be synthesized by a similar method to that of synthesis example 20-1 above.

Synthesis Embodiment 25

Synthesis of (E)-2-(4-(2-fluoro-6-(methylamino)pyridine-3-yl)buta-1-en-3-ynyl)benzofuran-5-ol (F1-PBBf3.2)

This can be synthesized by a similar method to that of synthesis example 20-1 above.

Synthesis Embodiment 26

Synthesis of 2-((1E,3E)-4-(6-(dimethylamino)pyridine-3-yl)buta-1,3-dienyl)quinoline-6-ol (PBQ3.0)

PBQ3.0 was synthesized according to the following synthesis scheme:

Synthesis Scheme

[Formula 59]

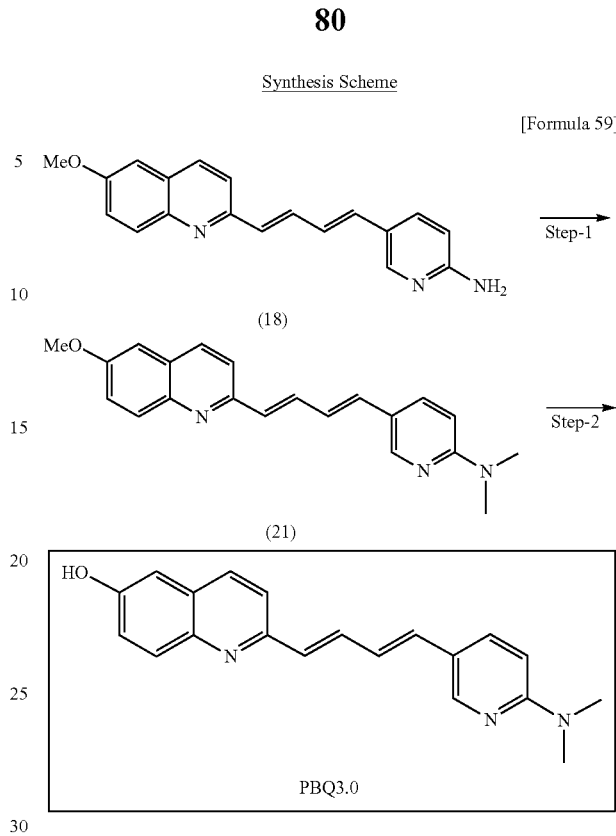

Step 1: Synthesis of Compound (21)

Under an argon atmosphere, after a tetrahydrofuran solution (80 mL) of the compound (18) (1213 mg, 4.00 mmol) was cooled with ice, sodium hydride (60% oil, 960 mg, 24.00 mmol) was added. After the reaction liquid was heated to room temperature and stirred for 30 minutes, methyl iodide (3407 mg, 24.00 mmol) was added. The reaction liquid was added in water and stirred, and extracted with chloroform. After the organic layer was washed with saturated saline water and dried with anhydrous sodium sulphate, the solvent was distillated under reduced pressure. By refining the residue by column chromatography (developing solvent: chloroform→chloroform/methanol=97/3), 804 mg of the title compound (21) was obtained.

Step 2: Synthesis of PBQ3.0

Under an argon atmosphere, after a dichloromethane solution (80 mL) of the compound (21) (800 mg, 2.41 mmol) was cooled down to −40° C., boron tribromide (1.0 M dichloromethane solution, 12.1 mL, 12.10 mmol) was added dropwise. The reaction liquid was heated to 5° C., and stirred all night. After the reaction liquid was neutralized by adding a sodium hydroxide aqueous solution under ice cold conditions, the organic layer was extracted with chloroform. After the organic layer was washed with water and saturated saline water and dried with anhydrous sodium sulphate, the solvent was distillated under reduced pressure. The residue was refined by column chromatography (developing solvent: chloroform→chloroform/methanol=19/1). Methanol was added to the refined product, the refined product was suspended and washed, and the precipitate was filtered. The cake was dried under reduced pressure, and 110 mg of PBQ3.0 was obtained.

PBQ3.0: $^1$H NMR (400 MHz, DMSO-d$_6$) δ ppm: 9.96 (s, 1H), 8.19 (d, J=2.29 Hz, 1H), 8.05 (d, J=8.69 Hz, 1H), 7.79 (dd, J=9.15 Hz, 2.29 Hz, 1H), 7.77 (d, J=9.15 Hz, 1H), 7.62 (d, J=8.69 Hz, 1H), 7.47 (dd, J=15.10 Hz, 10.52 Hz, 1H), 7.26 (dd, J=9.15 Hz, 2.75 Hz, 1H), 7.09 (d, J=2.29 Hz, 1H), 6.99 (dd, J=15.10 Hz, 10.52 Hz, 1H), 6.78 (d, J=15.55 Hz, 1H), 6.77 (d, J=15.10 Hz, 1H), 6.68 (d, J=8.69 Hz, 1H), 3.06 (s, 6H).
Synthesis Embodiment 27
Synthesis of 2-((1E,3E)-4-(6-(methylamino)pyridine-3-yl)buta-1,3-dienyl)quinoline-6-ol (PBQ3)
PBQ3 was synthesized according to the following synthesis scheme:
Synthesis Scheme
[Formula 60]
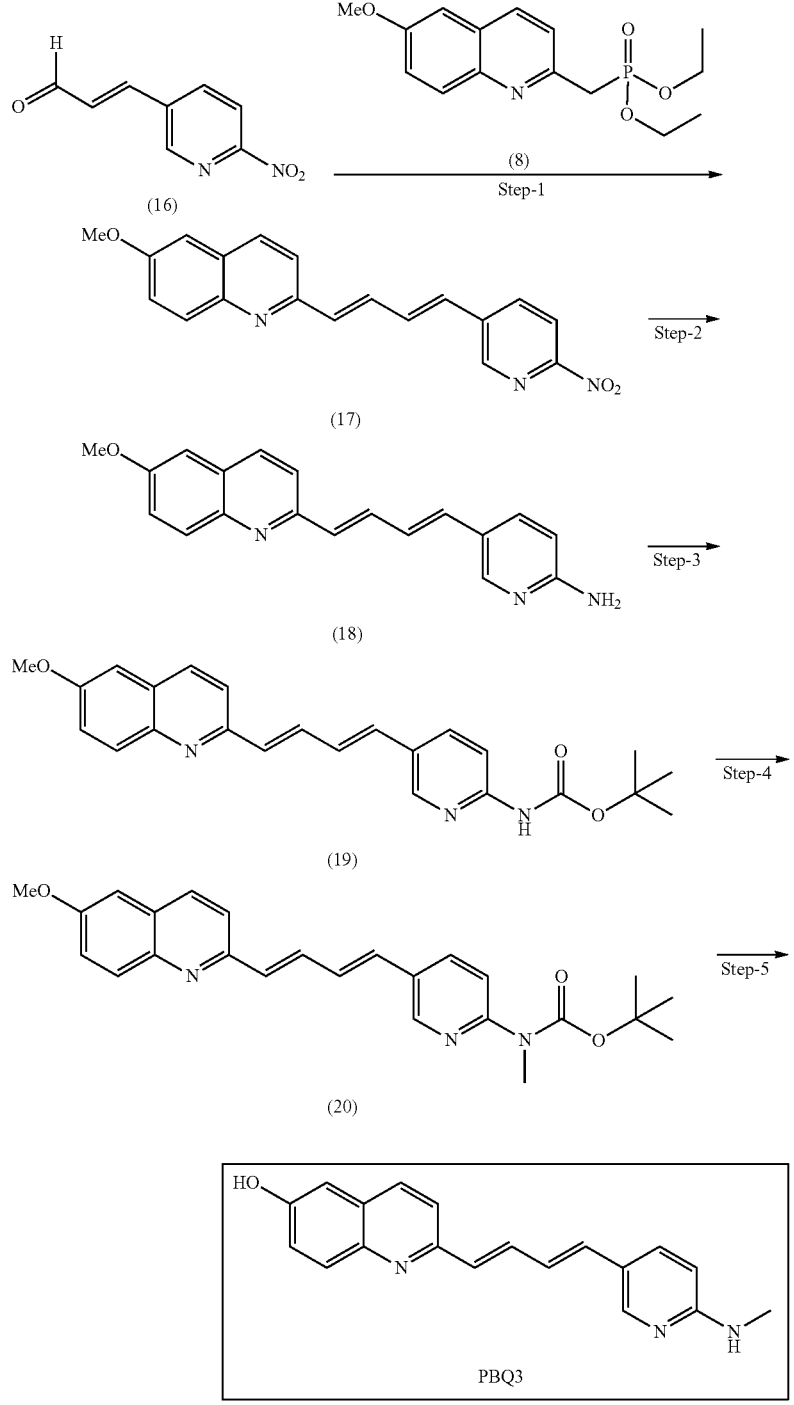

Step 1: Synthesis of Compound (17)

Under an argon atmosphere, after a tetrahydrofuran solution (200 mL) of the compound (8) (17.60 g, 56.9 mmol) was cooled with ice, tert-butyllithium (1.61M hexane solution, 38.9 mL, 62.6 mmol) was added dropwise. After the reaction liquid was stirred for 60 minutes, a tetrahydrofuran solution (100 mL) of the compound (16) (10.14 g, 56.9 mmol) was added dropwise. The reaction liquid was heated to room temperature, and, after the disappearance of the raw material, the reaction liquid was added water, and extracted with chloroform. After the organic layer was washed with water and saturated saline water and dried with anhydrous sodium sulphate, the solvent was distillated under reduced pressure. By refining the residue by column chromatography (developing solvent: chloroform→chloroform/ethyl acetate=19/1), 5.60 g of the title compound (17) was obtained.

Step 2: Synthesis of Compound (18)

Acetic acid (250 mL), iron (3.94 g, 70.5 mmol) and 12N hydrochloric acid (21 mL) were added in an ethanol solution (500 mL) of the compound (17) (5.00 g, 15.00 mmol). The reaction liquid was heated to 70° C., and, after the disappearance of the raw material was confirmed, cooled with ice. After a sodium hydroxide aqueous solution was added dropwise to the reaction liquid and chloroform was added thereto, the reaction liquid was filtered through celite. The filtrate was extracted with chloroform, and the organic layer was distillated under reduced pressure. By refining the residue by column chromatography (developing solvent: chloroform→chloroform/methanol=50/1), 3.01 g of the title compound (18) was obtained.

Step 3: Synthesis of Compound (19)

t-butyl alcohol (200 mL) and di-tert-butyl dicarbonate (1109 mg, 5.08 mmol) were added in a tetrahydrofuran solution (40 mL) of the compound (18) (1402 mg, 4.62 mmol), and the resultant solution was heated to 35° C. and stirred all night. By distillating the reaction liquid under reduced pressure and refining the residue by column chromatography (developing solvent: chloroform→chloroform/methanol=24/1), 1078 mg of the title compound (19) was obtained.

Step 4: Synthesis of Compound (20)

Under an argon atmosphere, a tetrahydrofuran solution (133 mL) of the compound (19) (1074 mg, 2.66 mmol) was cooled with ice, and sodium hydride (60% oil, 319 mg, 7.99 mmol) was added thereto. After the reaction liquid was heated to room temperature and stirred for 30 minutes, methyl iodide (1133 mg, 7.99 mmol) was added. The reaction liquid was added in water and stirred, and was extracted with chloroform. After the organic layer was washed with saturated saline water and dried with anhydrous sodium sulphate, the solvent was distillated under reduced pressure. By refining the residue by column chromatography (developing solvent: chloroform→chloroform/methanol=97/3), 701 mg of the title compound (20) was obtained.

Step 5: Synthesis of PBQ3

Under an argon atmosphere, after a dichloromethane solution (60 mL) of the compound (20) (670 mg, 1.60 mmol) was cooled down to −40° C. boron tribromide (1.0 M dichloromethane solution, 8.02 mL, 8.02 mmol) was added dropwise. The reaction liquid was heated to 0° C. and stirred all night. The reaction liquid was heated to 10° C. and stirred for 60 minutes. After the reaction liquid was neutralized by adding methanol and sodium hydrogen carbonate under ice cold conditions, the organic layer was extracted with dichloromethane. After the organic layer was washed with water and saturated saline water and dried with anhydrous sodium sulphate, the solvent was distillated under reduced pressure. The residue was refined by column chromatography (developing solvent: chloroform/methanol=99/1→9/1). Methanol was added to the refined product, the refined product was suspended and washed, and the precipitate was filtered. By drying the cake under reduced pressure, 120 mg of PBQ3 was obtained.

PBQ3: $^1$H NMR (400 MHz, DMSO-$d_6$) δ ppm: 9.95 (s, 1H), 8.08 (d, J=2.29 Hz, 1H), 8.04 (d, J=8.69 Hz, 1H), 7.77 (d, J=9.15 Hz, 1H), 7.69 (dd, J=8.69 Hz, 2.29 Hz, 1H), 7.62 (d, J=8.69 Hz, 1H), 7.46 (dd, J=15.56 Hz, 10.98 Hz, 1H), 7.26 (dd, J=9.15 Hz, 2.75 Hz, 1H), 7.08 (d, J=2.75 Hz, 1H), 6.92 (dd, J=15.56 Hz, 10.98 Hz, 1H), 6.81 (q, J=5.03 Hz, 1H), 6.75 (d, J=15.55 Hz, 1H), 6.74 (d, J=15.10 Hz, 1H), 6.47 (d, J=9.15 Hz, 1H), 2.80 (d, J=5.03 Hz, 3H).

Synthesis Embodiment 28

Synthesis of (E)-2-(4-(6-(dimethylamino)pyridine-3-yl)buta-1-en-3-ynyl)quinoline-6-ol (PBQ3.1)

PBQ3.1 was synthesized according to the following synthesis scheme:

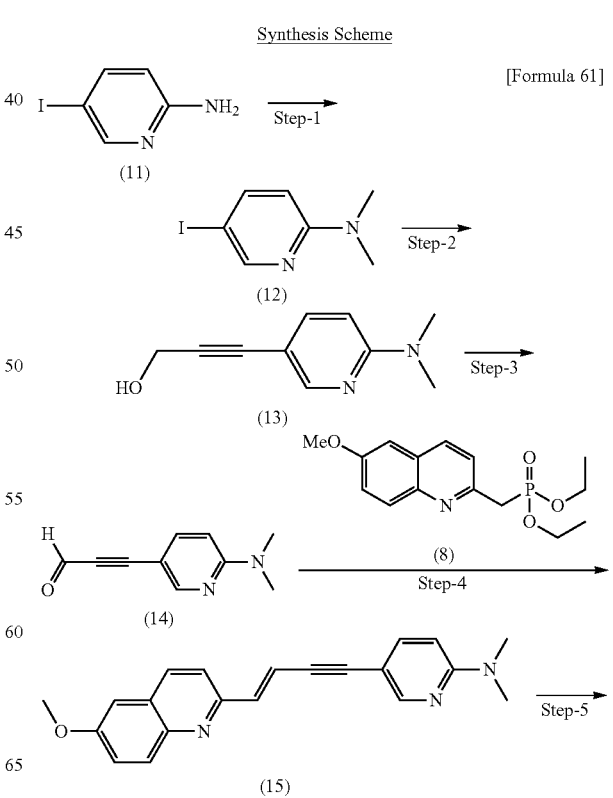

Synthesis Scheme

[Formula 61]

-continued

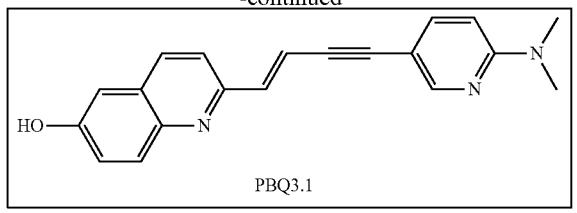
PBQ3.1

Step 1: Synthesis of Compound (12)

Under an argon atmosphere, after a N,N-dimethylformamide solution (20 mL) of 5-iodo-2-aminopyridine (11) (2200 mg, 10.0 mmol) was cooled with ice, sodium hydride (60% oil, 1200 mg, 30.0 mmol) was added thereto. The reaction liquid was heated to room temperature, and stirred for 30 minutes. The reaction liquid was cooled with ice, and, after methyl iodide (4258 mg, 30.0 mmol) was added thereto, the reaction liquid was heated to room temperature. After the disappearance of the raw material, the reaction liquid was added in water and stirred, and the organic layer was extracted with ethyl acetate. After the organic layer was washed with water and saturated saline water and dried with anhydrous sodium sulphate, the solvent was distilled under reduced pressure. By refining the residue by column chromatography (developing solvent: heptane/ethyl acetate=99/1→24/1), 2086 mg of the title compound (12) was obtained.

Step 2: Synthesis of Compound (13)

Under an argon atmosphere, copper iodide (191 mg, 1.00 mmol), 2-propyn-1-ol (939 mg, 16.75 mmol) and dichlorobis (triphenylphosphine) palladium (II) (118 mg, 0.17 mmol) were added in a triethylamine solution (8.17 mL, 58.61 mmol) of the compound (12) (2077 mg, 8.37 mmol), and the resultant solution was stirred. After the disappearance of the raw material was confirmed, the reaction liquid was filtered, and the solvent was distilled under reduced pressure. By refining the residue by column chromatography (developing solvent: heptane/ethyl acetate=19/1→1/1), 1340 mg of the title compound (13) was obtained.

Step 3: Synthesis of Compound (14)

Under an argon atmosphere, triethylamine (2534 mg, 25.04 mmol) and a pyridine sulfur trioxide complex (3623 mg, 22.76 mmol) were added in a dimethylsulfoxide solution (37.9 mL) of the compound (13) (1337 mg, 7.59 mmol), and the resultant solution was stirred. After the disappearance of the raw material was confirmed, water was added in the reaction liquid, and the organic layer was extracted using ethyl acetate. After the organic layer was washed with water and saturated saline water and dried with anhydrous sodium sulphate, the solvent was distilled under reduced pressure. By refining the residue by column chromatography (developing solvent: heptane/ethyl acetate=24/1→5/1), 849 mg of the title compound (14) was obtained.

Step 4: Synthesis of Compound (15)

Under an argon atmosphere, after a tetrahydrofuran solution (30 mL) of the compound (8) (928 mg, 3.00 mmol) was cooled with ice, sodium hydride (60% oil, 144 mg, 3.60 mmol) was added thereto. After the reaction liquid was heated to room temperature and stirred for 30 minutes, the compound (14) (784 mg, 4.50 mmol) was added thereto. After the reaction liquid was heated to 40° C. and the raw material disappeared, water was added in the reaction liquid, and the organic layer was extracted using ethyl acetate. After the organic layer was washed with water and saturated saline water and dried with anhydrous sodium sulphate, the solvent was distillated under reduced pressure. The residue was refined by column chromatography (developing solvent: chloroform→chloroform/methanol=50/1). Methanol was added to the refined product, the refined product was suspended and washed, and the precipitate was filtered. By drying the cake under reduced pressure, 583 mg of the title compound (15) was obtained.

Step 5: Synthesis of PBQ3.1

Under an argon atmosphere, after a dichloromethane solution (5.0 mL) of the compound (15) (329 mg, 1.00 mmol) was cooled down to −40° C., boron tribromide (1.0 M dichloromethane solution, 5.00 mL, 5.00 mmol) was added dropwise. The reaction liquid was heated to 5° C., and stirred all night. After the reaction liquid was neutralized by adding a 1N sodium hydroxide aqueous solution and sodium hydrogen carbonate under ice cold conditions, the organic layer was extracted with ethyl acetate. After the organic layer was washed with water and saturated saline water and dried with anhydrous sodium sulphate, the solvent was distillated under reduced pressure. The residue was refined by column chromatography (developing solvent: chloroform/methanol=99/1→17/1). Methanol was added to the refined product, the refined product was suspended and washed, and the precipitate was filtered. By drying the cake under reduced pressure, 147 mg of PBQ3.1 was obtained.

PBQ3.1: $^1$H NMR (400 MHz, DMSO-$d_6$) δ ppm: 10.09 (s, 1H), 8.26 (d, J=1.83 Hz, 1H), 8.12 (d, J=8.70 Hz, 1H), 7.82 (d, J=9.16 Hz, 1H), 7.66 (d, J=8.70 Hz, 1H), 7.61 (dd, J=9.16 Hz, 2.29 Hz, 1H), 7.30 (dd, J=9.16 Hz, 2.75 Hz, 1H), 7.13 (d, J=16.03 Hz, 1H), 7.12 (d, J=2.75 Hz, 1H), 7.05 (d, J=16.03 Hz, 1H), 6.67 (d, J=8.70 Hz, 1H), 3.07 (s, 6H).

Synthesis Embodiment 29

Synthesis of (E)-2-(4-(6-(methylamino)pyridine-3-yl)buta-1-en-3-ynyl)quinoline-6-ol (PBQ3.2)

PBQ3.2 was synthesized according to the following synthesis scheme:

Synthesis Scheme

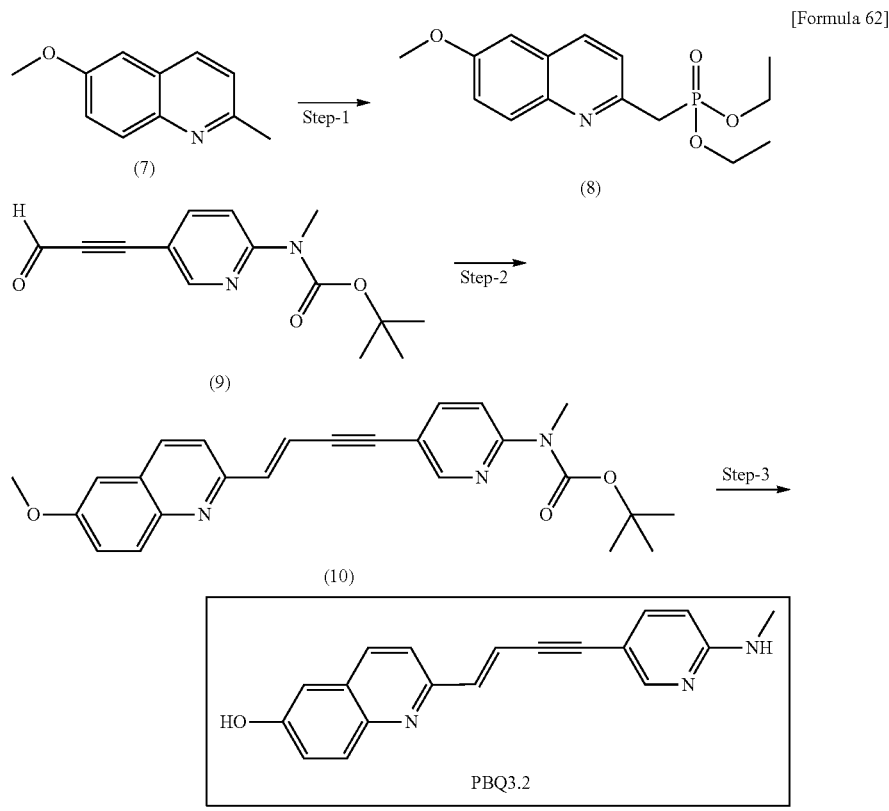

[Formula 62]

Step 1: Synthesis of Compound (8)

Under an argon atmosphere, after a tetrahydrofuran solution (600 mL) of 6-methoxy-2-methylquinoline (7) (43.0 g, 248 mmol) was cooled down to −70'C, tert-butyllithium (1.61M hexane solution, 200 mL, 322 mmol) was added dropwise. The reaction liquid was stirred for 1 hour, and diethyl chlorophosphate (59.9 g, 347 mmol) was added dropwise. The reaction liquid was stirred for 1 hour, and, after water was added and the reaction liquid was stirred all night, the reaction liquid was extracted with ethyl acetate. After the organic layer was washed with saturated saline water and dried with anhydrous sodium sulphate, the solvent was distillated under reduced pressure. By refining the residue by column chromatography (developing solvent: ethyl acetate→ethyl acetate/methanol=19/1), 27.2 g of the title compound (8) was obtained.

Step 2: Synthesis of Compound (10)

Under an argon atmosphere, after a tetrahydrofuran solution (30 mL) of the compound (8) (928 mg, 3.00 mmol) was cooled with ice, sodium hydride (60% oil, 144 mg, 3.60 mmol) was added thereto. After the reaction liquid was heated to room temperature and stirring for 30 minutes, the compound (9) (937 mg, 3.60 mmol) was added. After the reaction liquid was heated to 40° C. and the raw material disappeared, water was added in the reaction liquid, and the reaction liquid was extracted with ethyl acetate. After the organic layer was washed with water and saturated saline water and dried with anhydrous sodium sulphate, the solvent was distillated under reduced pressure. By refining the residue by column chromatography (developing solvent: heptane/ethyl acetate=7/1→3/1), 580 mg of the title compound (10) was obtained.

Step 3: Synthesis of PBQ3.2

Under an argon atmosphere, after a dichloromethane solution (7.0 mL) of the compound (10) (575 mg, 1.38 mmol) was cooled down to −40° C., boron tribromide (1.0 M dichloromethane solution, 11.1 mL, 11.1 mmol) was added dropwise. The reaction liquid was heated to 5° C., and stirred all night. After the reaction liquid was neutralized by adding a 1N sodium hydroxide aqueous solution and a sodium hydrogen carbonate solution under ice cold conditions, the precipitate was filtered. The cake was refined by column chromatography (developing solvent: chloroform/methanol=99/1→19/1). Methanol was added to the refined product, the refined product was suspended and washed, and the precipitate was filtered. By drying the cake under reduced pressure, 110 mg of PBQ3.2 was obtained.

PBQ3.2: $^1$H NMR (400 MHz, DMSO-$d_6$) δ ppm: 10.09 (s, 1H), 8.18 (d, J=2.29 Hz, 1H), 8.11 (d, J=8.70 Hz, 1H), 7.82 (d, J=9.16 Hz, 1H), 7.66 (d, J=8.70 Hz, 1H), 7.48 (dd, J=8.70 Hz, 2.29 Hz, 1H), 7.30 (dd, J=9.16 Hz, 2.75 Hz, 1H), 7.12 (d, J=2.75 Hz, 1H), 7.11 (d, J=16.03 Hz, 1H), 7.02-7.07 (m, 1H), 7.04 (d, J=16.03 Hz, 1H), 6.47 (d, J=8.70 Hz, 1H), 2.80 (d, J=4.58 Hz, 3H).

Synthesis Embodiment 30

Synthesis of 2-((1E,3E)-4-(4-aminophenyl)buta-1,3-dienyl)benz[d]thiazole-6-ol (pre2)

pre2 was synthesized according to the following synthesis scheme:

Synthesis Scheme

[Formula 63]

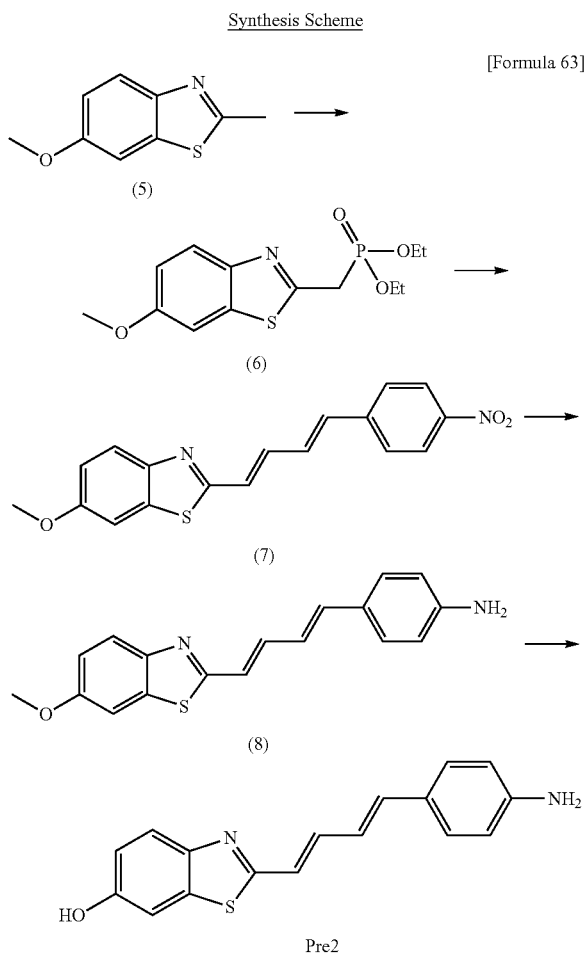

Step 1: Synthesis of Compound (6)

Under an argon atmosphere, after a tetrahydrofuran solution (75 mL) of diisopropylamine (5.06 g, 50.0 mmol) was cooled down to −50° C., n-butyllithium (1.6 M hexane solution, 31.2 mL, 50.0 mmol) was added dropwise. The reaction liquid was cooled down to −65° C., and a tetrahydrofuran solution (25 mL) of 6-methoxy-2-methylbenzothiazole (5)(4.48 g, 25.0 mmol) was added dropwise. Diethyl chlorophosphate (4.31 g, 25.0 mmol) was added dropwise to the reaction liquid. After the disappearance of the raw material, the reaction liquid was added in 100 mL of a 1M hydrogen chloride solution, and the organic layer was extracted with chloroform. The organic layer was dried with anhydrous sodium sulphate, and the solvent was distillated under reduced pressure. By refining the residue by column chromatography (developing solvent: chloroform), 6.30 g of the title compound (6) was obtained.

Step 2: Synthesis of Compound (7)

Under an argon atmosphere, after a tetrahydrofuran solution (10 mL) of the compound (6) (380 mg, 1.21 mmol) was cooled with ice, sodium hydride (60% oil, 48 mg, 1.20 mmol) was added thereto. After the reaction liquid was heated to room temperature and stirred for 30 minutes, 4-nitrocinnamaldehyde (180 mg, 1.02 mmol) was added. After the disappearance of the raw material, the reaction liquid was added in water and stirred, and the precipitate was filtered. Toluene was added to the cake, and the solvent was distillated under reduced pressure, and suspended and washed with chloroform. By filtering and drying under reduced pressure the precipitate, 275 mg of the title compound (7) was obtained.

Step 3: Synthesis of Compound (8)

Acetic acid (5.1 mL), iron (212 mg, 3.80 mmol) and 12N hydrochloric acid (1.1 mL) were added in an ethanol solution (5.1 mL) of the compound (7) (271 mg, 0.80 mmol), and the resultant solution was stirred all night. The reaction liquid was added dropwise in a sodium hydroxide aqueous solution under ice cold conditions, and, after chloroform was added, the reaction liquid was filtered. After the filtrate was extracted with chloroform and the organic layer was dried with anhydrous sodium sulphate, the solvent was distillated under reduced pressure. By refining the residue by column chromatography (developing solvent: chloroform), 165 mg of the title compound (8) was obtained.

Step 4: Synthesis of 2-((1E,3E)-4-(4-aminophenyl)buta-1,3-dienyabenz[d]thiazole-6-01 (pre2)

Under an argon atmosphere, after a dichloromethane solution (2.6 mL) of the compound (8) (160 mg, 0.52 mmol) was cooled down to −78° C., boron tribromide (1.0M dichloromethane solution, 2.60 mL, 2.60 mmol) was added dropwise. The reaction liquid was heated to room temperature, and stirred all night. After the reaction liquid was made alkaline by adding a 1N sodium hydroxide aqueous solution under ice cold conditions, the resultant liquid was filtered. The filtrate was neutralized by adding 1N hydrochloric acid and sodium hydrogen carbonate, and the precipitate was filtered. Chloroform was added to the cake, the resultant mixture was suspended and washed, and the precipitate was filtered. Methanol was added to the cake, the resultant mixture was suspended and washed, and the precipitate was filtered. By drying the cake under reduced pressure, 120 mg of the title compound was obtained.

pre2: $^1$H NMR (400 MHz, DMSO-$d_6$) δ ppm: 9.80 (s, 1H), 7.69 (d, J=8.70 Hz, 1H), 7.31 (d, J=2.29 Hz, 1H), 7.25 (d, J=8.70 Hz, 2H), 7.20 (dd, J=16.03 Hz, 9.16 Hz, 1H), 6.92 (dd, J=8.70 Hz, 2.29 Hz, 1H), 6.81-6.91 (m, 2H), 6.81 (d, J=16.03 Hz, 1H), 6.56 (d, J=8.70 Hz, 2H), 5.52 (s, 2H)

Synthesis Embodiment 31

Synthesis of 5-((1E,3E)-4-(6-(tert-butyldimethylsilyloxy)benz[d]thiazole-2-yl)buta-1,3-dienyl)pyridine-2-amine (pre3)

pre3 was synthesized according to the following synthesis scheme:

Synthesis Scheme

[Formula 64]

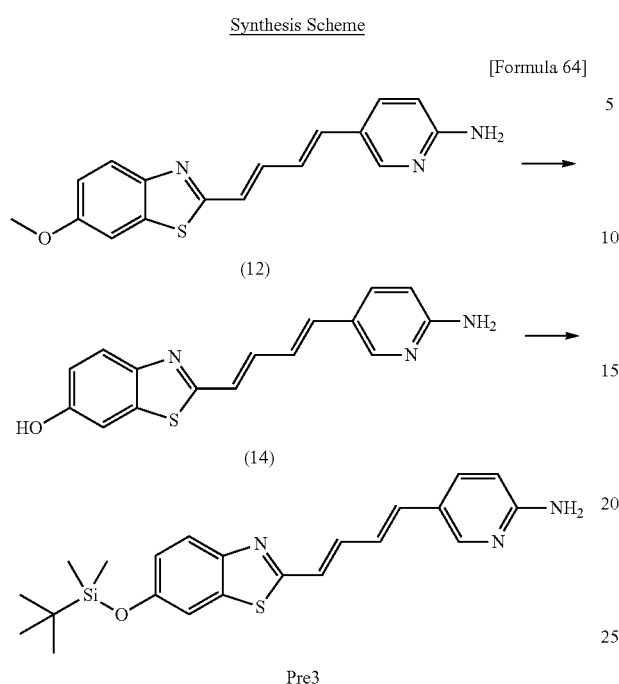

Step 1: Synthesis of Compound (14)

Under an argon atmosphere, after a dichloromethane solution (2.9 mL) of the compound (12) (184 mg, 0.57 mmol) was cooled down to −78° C., boron tribromide (1.0M dichloromethane solution, 2.85 mL, 2.85 mmol) was added dropwise. The reaction liquid was heated to room temperature, and stirred all night. The reaction liquid was neutralized by adding a 1N sodium hydroxide aqueous solution and sodium hydrogen carbonate under ice cold conditions, and the solvent was distillated under reduced pressure. The residue was suspended and washed with water. The precipitate was filtered and dried under reduced pressure, thereby giving 154 mg of the title compound (14).

Step 2: Synthesis of 5-((1E,3E)-4-(6-(tert-butyldimethylsilyloxy)benz[d]thiazole-2-yl)buta-1,3-dienyl) pyridine-2-amine (pre3)

Under an argon atmosphere, imidazole (72.6 mg, 1.066 mmol) and t-butyldimethylchlorosilane (73.5 mg, 0.489 mmol) were added in a dimethylsulfoxide solution (2.58 mL) of the compound (14) (90.0 mg, 0.305 mmol), and the resultant solution was stirred all night. Water was added in the reaction liquid, and the reaction liquid was extracted with ethyl acetate. After the organic layer was washed with saturated saline water and dried with anhydrous sodium sulphate, the solvent was distillated under reduced pressure. By refining the residue by column chromatography (developing solvent: chloroform→chloroform/methanol=100/7), 52 mg of the title compound was obtained.

pre3: $^1$H NMR (400 MHz, DMSO-d$_6$) δ ppm: 8.04 (d, J=2.29 Hz, 1H), 7.77 (d, J=8.07 Hz, 1H), 7.68 (dd, J=8.70 Hz, 2.29 Hz, 1H), 7.53 (d, J=2.29 Hz, 1H), 7.28 (dd, J=15.57 Hz, 10.08 Hz, 1H), 6.99 (dd, J=8.70 Hz, 2.75 Hz, 1H), 6.88-6.96 (m, 1H), 6.86 (d, J=15.57 Hz, 1H), 6.85 (d, J=15.57 Hz, 1H), 6.47 (d, J=8.70 Hz, 1H), 6.35 (s, 2H), 0.98 (s, 9H), 0.23 (s, 6H)

Synthesis Embodiment 32

Synthesis of 2-((1E,3E)-4-(4-(dimethylamino)phenyl)buta-1,3-dienyl)-3-ethyl-6-hydroxy-benz[d]thiazole-3-ium (pre6)

The synthesis was performed in a method similar to the synthesis methods of synthesis example 5 and PBB5 above.

Synthesis Embodiment 33

Synthesis of (E)-5-(4-(6-(tert-butyldimethylsilyloxy)benz[d]thiazole-2-yl)buta-3-en-1-ynyl) pyridine-2-amine (pre11)

pre11 was synthesized according to the following synthesis scheme:

Synthesis Scheme

[Formula 65]

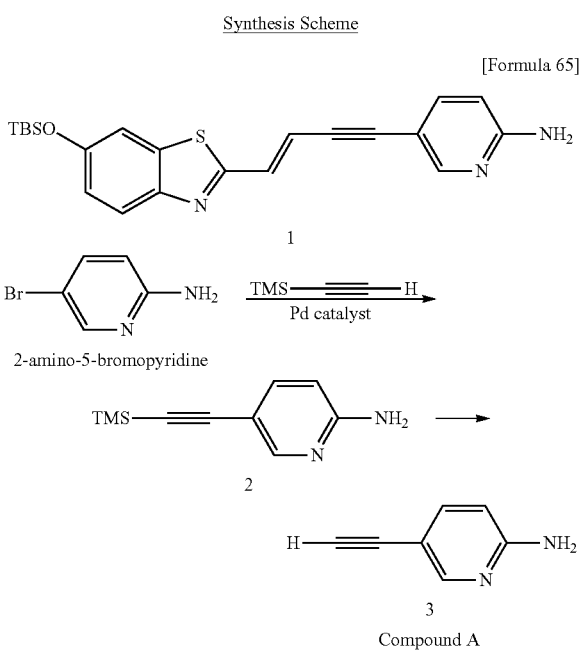

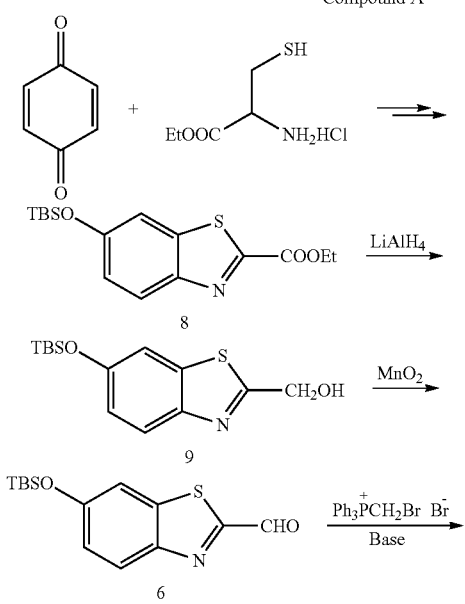

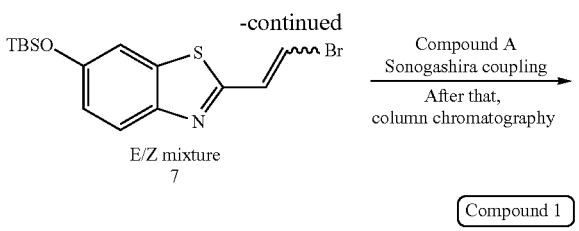

-continued

Compound A
Sonogashira coupling
After that,
column chromatography

E/Z mixture
7

Compound 1

Step 1: Synthesis of 6-(t-butyldimethylsilyloxy) benzothiazole-2-carboxylic acid ethyl (8)

A DMF solution (3 mL) of t-butyldimethylchlorosilane (0.94 g, 6.2 mmol) was added in a DMF solution (10 mL) of 6-hydroxy-benzothiazole-2-carboxylic acid ethyl (1.27 g, 5.69 mmol) and imidazole (0.5 g, 7.34 mmol), and, after the resultant solution was stirred at room temperature for 16 hours, water was added, and the resultant liquid was extracted with ethyl acetate. After the extracted liquid was washed with water, the resultant liquid was dried with anhydrous sodium sulphate, and the solvent was distilled at reduced pressure. The resulting residue was refined by silica gel column chromatography, and 6-(t-butyldimethylsilyloxy)benzothiazole-2-carboxylic acid ethyl was obtained as a brown liquid (0.97 g, 2.9 mmol).

$^1$H-NMR (400 MHz, CDCl$_3$) δ ppm: 8.09 (d, J=8.8 Hz, 1H), 7.35 (d, J=2.4 Hz, 1H), 7.09 (dd, J=8.8 Hz, 2.4 Hz), 4.54 (q, J=7.2 Hz, 2H), 1.48 (t, J=7.2 Hz, 3H), 1.01 (s, 9H) (s, 6H)

Step 2: Synthesis of [6-(t-butyldimethylsilyloxy) benzothiazole-2-yl]methanol (9)

A THF solution (20 mL) of lithium aluminium hydride (87 mg, 2.3 mmol) was cooled down to −15° C., and a THF solution (10 mL) of 6-(t-butyldimethylsilyloxy)benzothiazole-2-carboxylic acid ethyl (0.77 g, 2.3 mmol) was added dropwise. After the resultant solution was stirred at the same temperature for 1 hour, lithium aluminium hydride (72.5 mg, 1.91 mmol) was added thereto, and the resultant solution was stirred for 30 more minutes. Water (0.16 mL) was added in the resultant solution, and, after stirring for a while, a 5M sodium hydroxide aqueous solution (0.16 mL) was added in the solution, followed by water (0.48 mL), and, after stirring, the insoluble matter was filtered using celite. The filtrate was condensed under reduced pressure, the residue was refined by silica gel column chromatography, and [6-(t-butyldimethylsilyloxy)benzothiazole-2-yl] methanol was obtained as a brown liquid (0.22 g, 0.74 mmol).

$^1$H-NMR (400 MHz, CDCl$_3$) δ ppm: 7.84 (d, J=8.8 Hz, 1H), 7.33 (d, J=2.4 Hz, 1H), 7.01 (dd, J=8.8 Hz, 2.4 Hz), 5.05 (br s, 2H) 2.78 (br s, 1H), 1.03 (s, 9H), 0.25 (s, 6H)

Step 3: Synthesis of 6-(t-butyldimethylsilyloxy) benzothiazole-2-carboxaldehyde (6)

A manganese dioxide powder (1.2 g) was added in a dichloromethane solution (30 mL) of [6-(t-butyldimethylsilyloxy)benzothiazole-2-yl]methanol (0.22 g, 0.74 mmol), and the resultant solution was stirred for 2.5 hours at 40° C. and for 16 hours at room temperature. The insoluble matter was filtered using celite, and the filtrate was condensed under reduced pressure. The resulting residue was refined by silica gel column chromatography, and 6-(t-butyldimethylsilyloxy)benzothiazole-2-carboxaldehyde was obtained as a brown liquid (71.0 mg, 0.242 mmol).

$^1$H-NMR (400 MHz, CDCl$_3$) δ ppm: 10.11 (s, 1H), 8.09 (d, J=8.8 Hz, 1H), 7.37 (d, J=2.4 Hz, 1H), 7.13 (dd, J=8.8 Hz, 2.4 Hz), 1.01 (s, 9H), 0.27 (s, 6H)

Step 4: Synthesis of 2-[(E)-2-bromoethenyl]-6-(t-butyldimethylsilyloxy) benzothiazole (7)

(Bromodifluormethyl) triphenylphosphonium bromide (48.2 mg, 0.11 mmol) was suspended in THF (including THF as a stabilizer, 3 mL), the resultant mixture was cooled down to −78° C., n-butyllithium (1.6M hexane solution, 0.15 mL) was added thereto, and the resultant mixture was stirred for 1 hour. Next, a THF solution (2 mL) of 6-(t-butyldimethylsilyloxy)benzothiazole-2-carboxaldehyde (20.2 mg, 0.0688 mmol) was added, and the resultant mixture was stirred at for approximately 30 minutes at −78° C., and for approximately 1.5 hours at 0° C. A saturated ammonium chloride aqueous solution was added in the reaction liquid (3 mL), and the resultant liquid was stirred for 10 minutes, and, after water and ethyl acetate were added, the resultant liquid was separated. After the organic layer was washed with saturated saline water, dried with anhydrous sodium sulphate, and condensed under reduced pressure, the resultant product was refined by silica gel column chromatography, and a mixture of 2-RE)-2-bromoetheny11-6-(t-butyldimethylsilyloxy)benzothiazole and BHT was obtained as a yellow liquid (7.0 mg). When the content of BHT and the title compound is to be calculated from the intensity ratio of 11-1-NMR signal, it is estimated that approximately 5.5 mg (0.015 mmol) of the title compound is contained.

$^1$H-NMR (400 MHz, CDCl$_3$) δ ppm: 7.84 (d, J=8.8 Hz, 1H), 7.35 (d, J=14.0 Hz, 1H), 7.29 (d, J=14.0 Hz, 1H), 7.25 (d, J=2.4 Hz, 1H), 7.00 (dd, J=8.8 Hz, 2.4 Hz), 1.00 (s, 9H), 0.26 (s, 6H)

Step 5: Synthesis of (E)-5-(4-(6-(t-butyldimethylsilyloxy)benzothiazole-2-yl)-3-butene-1-ynyl)pyridine-2-amine (1)

A mixture of 2-[(E)-2-bromoethenyl]-6-(t-butyldimethylsilyloxy)benzothiazole and BHT (18.1 mg, including 13.5 mg of 2-[(E)-2-bromoethenyl]-6-(t-butyldimethylsilyloxy) benzothiazole), 2-amino-5-ethynylpyridine (8.7 mg, 0.074 mmol), cuprous iodide (0.7 mg), and dichlorobis (triphenylphosphine) palladium (2 mg) were added in a liquid mixture of THF (1 mL) and triethylamine (1 mL), and the resultant mixture was stirred at 70° C. for 4 hours. After ethyl acetate was added, the insoluble matter was filtered, and, after the filtrate was condensed under reduced pressure and refined by silica gel column chromatography, a mixture of the title compound and its (Z)-isomer was obtained as a yellow-brown amorphous solid (9.4 mg). E/Z= approximately 85/15 ($^1$H-NMR).

pre11: $^1$H-NMR (400 MHz, CDCl$_3$) δ ppm: 8.24 (br d, J=2.0 Hz, 1H), 7.84 (d, J=8.8 Hz, 1H), 7.53 (dd, J=8.4 Hz, 2.0 Hz), 7.26 (d, J=2.4 Hz, 1H), 7.16 (d, J=16.0 Hz, 1H), 6.98 (dd, J=8.8 Hz, 2.4 Hz), 6.73 (d, J=16.0 Hz, 1H), 6.47 (dd, J=8.4 Hz, 0.4 Hz), 4.70 (s, 2H), 1.01 (s, 9H), 0.23 (s, 6H)

Synthesis Embodiment 34

Synthesis of (E)-tert-butyl(2-(4-(6-aminopyridine-3-yl)buta-1-en-3-ynyl)benz[d]thiazole-6-yl)methylcarbamate (pre12)

pre12 was synthesized according to the following synthesis scheme:

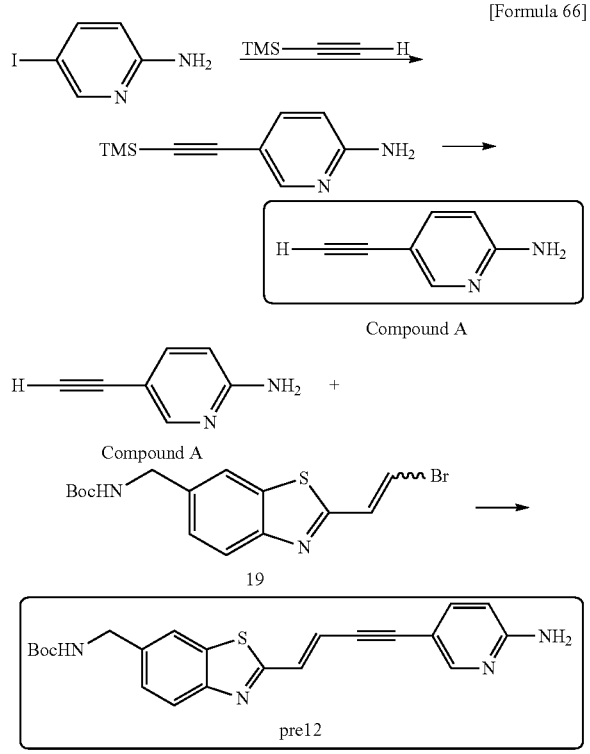

[Formula 66]

2-amino-5-ethynylpyridine (compound A) was synthesized from 2-amino iodopyridine, as shown in the above scheme.

From 2-amino-5-ethynylpyridine (compound A) (0.14 g, 1.2 mmol) and 2-((E)-2-bromoetheny0-6-((tert-butoxycarbonylamino)methyl)benzothiazole (0.22 g, 0.60 mmol), the title compound was obtained in the same procedures as in step 5 of synthesis example 33 above (181.7 mg, 0.447 mmol).

Pre12: $^1$H-NMR (400 MHz, CDCl$_3$) δ ppm: 8.25 (d, J=1.6 Hz, 1H), 7.94 (d, J=8.4 Hz, 1H), 7.77 (br s, 1H), 7.53 (dd, J=8.8 Hz, 2.4 Hz, 1H), 7.39 (br d, J=8.4 Hz, 1H), 7.17 (d, J=16.0 Hz, 1H), 6.83 (d, J=16.0 Hz, 1H), 6.47 (dd, J=8.8 Hz, 0.8 Hz, 1H), 4.9 (br, 1H), 4.66 (s, 2H), 4.44 (br d, J=6.4 Hz, 2H), 1.47 (s, 9H)

Synthesis Embodiment 35-1

Synthesis of 2-(2-((1E, 3E)-4-(6-(methylamino)pyridine-3-yl)buta-1,3-dienyl)benz[d]thiazol e-6-yloxy)-2-hydroxymethyl-ethyl 4-methylbenzenesulfonate (analog of pre21)

An analog of pre21 was synthesized according to the following synthesis scheme:

Synthesis Scheme

[Formula 67]

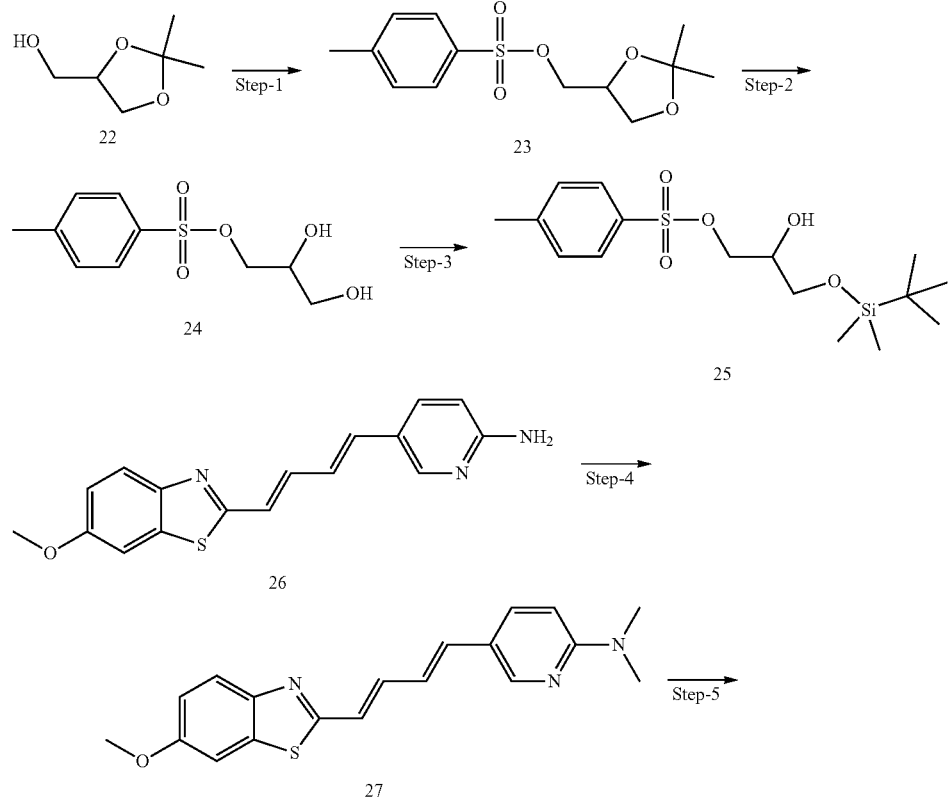

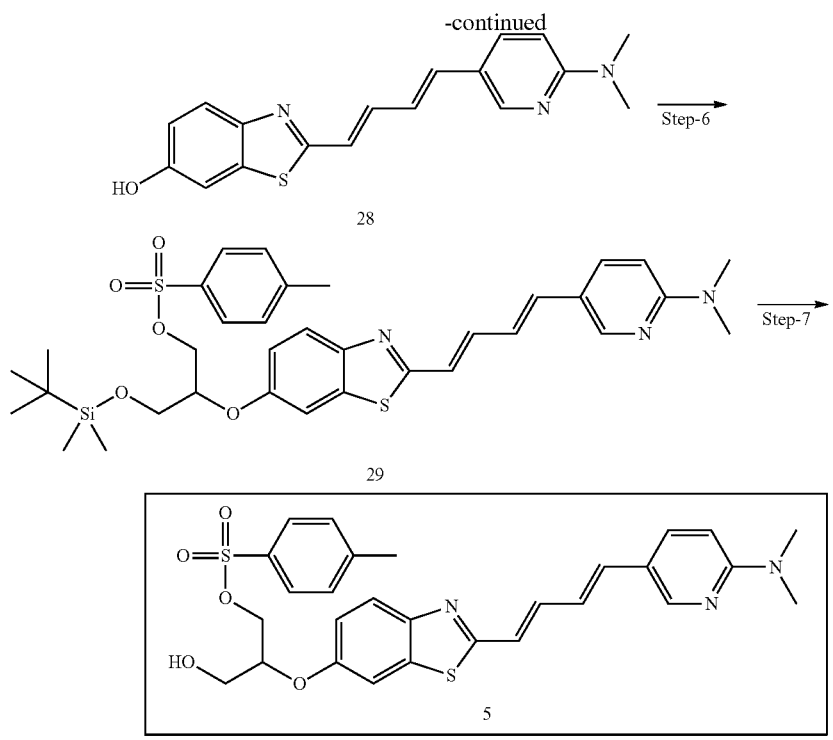

Step 1: Synthesis of Compound (23)

Under an argon atmosphere, after pyridine (7910 mg, 100.0 mmol) was added in a dichloromethane solution (10 mL) of 2,2-dimethyl-1,3-dioxolane-4-methanol (22) (1322 mg, 10.0 mmol) and the resultant solution was cooled with ice, p-oluenesulfonylchloride (2860 mg, 15.0 mmol) and N,N-dimethylaminopyridine (12 mg, 0.10 mmol) were added, and the resultant solution was stirred. After the disappearance of the raw material, water was added in the reaction liquid, and the reaction liquid was extracted using ethyl acetate. After the organic layer was washed with a hydrochloric acid aqueous solution, a sodium hydrogen carbonate aqueous solution and saturated saline water and dried with anhydrous sodium sulphate, the solvent was distillated under reduced pressure, and 2560 mg of the title compound (23) was obtained.

Step 2: Synthesis of Compound (24)

4N hydrochloric acid/dioxane (2.5 mL) was added in a methanol solution (7.5 mL) of the compound (23) (1432 mg, 5.00 mmol), and the resultant solution was stirred. After the disappearance of the raw material, the reaction liquid was distillated under reduced pressure, and, by refining the residue by column chromatography (developing solvent: heptane/ethyl acetate=1/4-4 ethyl acetate), 1027 mg of the title compound (24) was obtained.

Step 3: Synthesis of Compound (25)

Under an argon atmosphere, imidazole (272 mg, 4.00 mmol) was added in a tetrahydrofuran solution (4.0 mL) of the compound (24) (985 mg, 4.00 mmol), and the resultant solution was cooled with ice. A tetrahydrofuran solution (4.0 mL) of t-butyldimethylchlorosilane (603 mg, 4.00 mmol) was added dropwise to the reaction liquid. After the disappearance of the raw material, water was added in the reaction liquid, and the organic layer was extracted with ethyl acetate. After the organic layer was washed with water and saturated saline water and dried with anhydrous sodium sulphate, the solvent was distillated under reduced pressure. By refining the residue by column chromatography (developing solvent: heptane/ethyl acetate=7/1→4/1), 1182 mg of the title compound (25) was obtained.

Step 4: Synthesis of Compound (27)

Under an argon atmosphere, after a N,N-dimethylformamide solution (11 mL) of the compound (26) (which had been synthesized in the previous test preparation report) (696 mg, 2.25 mmol) was cooled with ice, sodium hydride (60% oil, 360 mg, 9.00 mmol) was added in the resultant solution. The reaction liquid was heated to room temperature and stirred for 30 minutes. After the reaction liquid was cooled with ice and methyl iodide (1277 mg, 9.00 mmol) was added thereto, the reaction liquid was heated to room temperature. After the disappearance of the raw material, the reaction liquid was added in water and stirred, and the precipitate was filtered. By refining the cake by column chromatography (developing solvent: chloroform→chloroform/methanol=99/1), 554 mg of the title compound (27) was obtained.

Step 5: Synthesis of Compound (28)

Under an argon atmosphere, after a dichloromethane solution (13 mL) of the compound (27) (550 mg, 1.63 mmol) was cooled down to −70° C., boron tribromide (1.0M dichloromethane solution, 16.3 mL, 16.30 mmol) was added dropwise. The reaction liquid was heated to 9° C., and stirred all night. After the reaction liquid was cooled with ice and neutralized by adding sodium hydroxide aqueous solution, the organic layer was distillated under reduced pressure. The precipitate was filtered, washed with water, and dried under reduced pressure, and 484 mg of the title compound (28) was obtained.

Step 6: Synthesis of Compound (29)

Under an argon atmosphere, the compound (25) (721 mg, 2.00 mmol) and triphenylphosphine (525 mg, 2.00 mmol) were added in a tetrahydrofuran solution (10.0 mL) of the compound (28) (323 mg, 1.00 mmol), and the resultant solution was cooled with ice. Diisopropyl azodicarboxylate (404 mg, 2.00 mmol) was added dropwise to the reaction liquid. After the reaction liquid was heated to room temperature and stirred all night, the reaction liquid was distillated under reduced pressure. By refining the residue by column chromatography (developing solvent: heptane/ethyl acetate=3/1→1/2), 270 mg of the title compound (29) was obtained.

Step 7: Synthesis of Compound (5)

4N hydrochloric acid/dioxane (1.5 mL) was added in a tetrahydrofuran solution (4.5 mL) of the compound (29) (200 mg, 0.30 mmol), and the resultant solution was stirred. After the disappearance of the raw material, the reaction liquid was cooled with ice and neutralized with a sodium hydrogen carbonate aqueous solution, and then the reaction liquid was extracted with ethyl acetate. After the organic layer was washed with water and saturated saline water and dried with anhydrous sodium sulphate, the solvent was distillated under reduced pressure. By refining the residue by column chromatography (developing solvent: heptane/ethyl acetate=1/1→1/4), 134 mg of the title compound (5) was obtained.

Compound (5): $^1$H NMR (400 MHz, DMSO-$d_6$) δ ppm: 8.21 (d, J=2.29 Hz, 1H), 7.79 (dd, J=9.16 Hz, 2.29 Hz, 1H), 7.75 (d, J=9.16 Hz, 1H), 7.73 (d, J=8.24 Hz, 2H), 7.52 (d, J=2.75 Hz, 1H), 7.39 (d, J=8.24 Hz, 2H), 7.31 (dd, J=14.78 Hz, 10.08 Hz, 1H), 6.85-7.06 (m, 4H), 6.70 (d, J=9.16 Hz, 1H), 5.07 (t, J=5.50 Hz, 1H), 4.53-4.60 (m, 1H), 4.20-4.35 (m, 2H), 3.52-3.63 (m, 2H), 3.07 (s, 6H), 2.35 (s, 3H).

Synthesis Embodiment 35-2

Synthesis of 3-(2-((1E,3E)-4-(6-(methylamino)pyridine-3-yl)buta-1,3-dienyl)benz[d]thiazol e-6-yloxy)-2-(tetrahydro-2H-pyran-2-yloxy)propyl 4-methyl-benzenesulfonate (pre21)

pre21 can be synthesized by the same method as that of synthesis example 35-1 above.

Synthesis Embodiment 36

Synthesis of (E)-3-(2-(4-(6-(methylamino)pyridine-3-yl)buta-1-en-3-ynyl)benz[d]thiazole-6-yloxy)-2-(tetrahydro-2H-pyran-2-yloxy)propyl 4-methylbenzenesulfonate (pre22)

pre22 can be synthesized by a similar method to those of synthesis examples 22 to 25 above.

Synthesis Embodiment 37

Synthesis of tert-butyl 5-((1E,3E)-4-(6-(ethoxymethoxy)benz[d]thiazole-2-yl)buta-1,3-dienyl)-6-nitro pyridine-2-yl(methyl)carbamate (pre23)

pre23 can be synthesized by a similar method to those of synthesis examples 22 to 25 above.

Synthesis Embodiment 38

Synthesis of (E)-tert-butyl 5-(4-(6-(ethoxymethoxy) benz[d]thiazole-2-yl)buta-3-en-1-ynyl)-6-nitropyridin e-2-yl(methyl)carbamate (pre24)

pre24 can be synthesized by a similar method to those of synthesis examples 22 to 25 above.

Synthesis Embodiment 39

Synthesis of tert-butyl 5-((1E,3E)-4-(5-(ethoxymethoxy)benzofuran-2-yl)buta-1,3-dienyl)-6-nitropyridine-2-yl(methyl)carbamate (pre25)

pre25 can be synthesized by a similar method to those of synthesis examples 22 to 25 above.

Synthesis Embodiment 40

Synthesis of (E)-tert-butyl 5-(4-(5-(ethoxymethoxy) benzofuran-2-yl)buta-3-en-1-ynyl) nitropyridine-2-yl(methyl)carbamate (pre26)

pre26 can be synthesized by a similar method to those of synthesis examples 22 to 25 above.

Synthesis of Radioisotope-Labeled Compound

Synthesis Embodiment 41

Synthesis of 4-((1E,3E)-4-(benz[d]thiazole-2-yl) buta-1,3-dienyl)-N-[$^{11}$C]methyl-N-methylaniline ([$^{11}$C]PBB1)

[$^{11}$C]PBB1 was synthesized according to the same method as the methods shown in following synthesis examples 42 and 43.

Synthesis Embodiment 42

Synthesis of 2-((1E,3E)-4-(4-([$^{11}$C]methylamino) phenyl)buta-1,3-dienyl)benz[d]thiazole-6-ol ([$^{11}$C] PBB2)

Synthesis Scheme

[Formula 68]

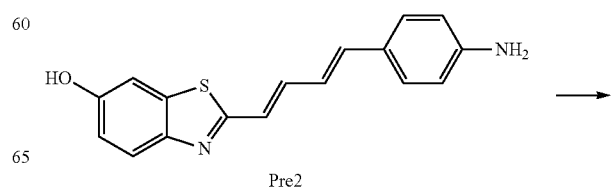

Pre2

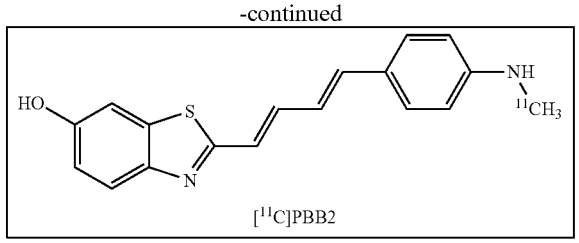

[11C]methyltriflate was added in an acetone solution (500 mL), contained 2-((1E,3E)-4-(4-aminophenyl)buta-1,3-dienyl)benz[d]thiazole-6-ol (pre2) (0.5 to 0.8 mg), at room temperature. Under a nitrogen atmosphere, acetone was removed at 80° C., and a 70% acetonitrile aqueous solution (800 μL) was added. The liquid mixture was moved to a HPLC purifying container (HPLC: CAPCELL PAK C18 column, 10 mm×250 mm, SHISEIDO; mobile phase, acetonitrile/water/triethylamine=700/300/1, 6 mL/minute). The fractions to match [$^{11}$C]PBB2 were collected in a flask, which contained, in ethanol (300 μL), 25% ascorbic acid (100 μL) and Tween80 (75 μL), and the solvent was distillated under reduced pressure. The residue was dissolved in a physiological saline water (3 mL, pH 7.4), and [$^{11}$C]PBB2 (640-1340 GBq) was obtained as an injection solution.

Synthesis Embodiment 43

Synthesis of 2-((1E,3E)-4-(6-([$^{11}$C]methylamino) pyridine-3-yl)buta-1,3-dienyl)benz[d]thiazole-6-ol ([$^{11}$C]PBB3)

Synthesis Scheme

[Formula 69]

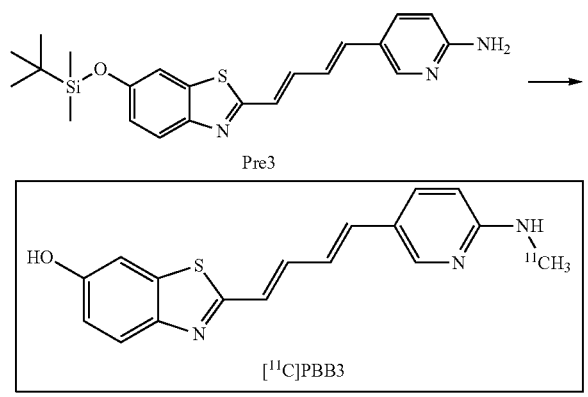

Iodo [$^{11}$C]methane was added, at room temperature, in a DMSO solution (300 μL), which contained 5-((1E,3E)-4-(6-(tert-butyldimethylsilyloxy)benz[d]thiazole-2-yl)buta-1,3-dienyl)pyridine-2-amine (pre3) (1.5 to 2 mg) and potassium hydroxide (10 mg). The reaction liquid mixture was heated to 125° C. and maintained for 5 minutes. After the reaction container was cooled down, an aqueous solution (600 μL) of a tetra-n-butylammoniumfluoride hydrate (5 mg) μ was added, and the protecting group was removed. After that, a HPLC solvent (500 μL) was added. The liquid mixture was moved to an HPLC purifying container (HPLC: CAPCELL PAK C18 column, 10 mm×250 mm, acetonitrile/50 mM ammonium formate=4/6, 6 mL/minute). The fractions to match [$^{H}$C]PBB3 were collected in a flask, which contained, in ethanol (300 μL), 25% ascorbic acid (100 μL) and Tween80 (75 μL), and the solvent was distillated under reduced pressure. The residue was dissolved in physiological saline water (3 mL, pH 7.4), and [$^{11}$C]PBB3 (970-1990 GBq) was obtained as an injection solution.

Synthesis Embodiment 44

Synthesis of 2-((1E,3E)-4-(6-([$^{11}$C] methylamino) pyridine-3-yl)buta-1,3-dienyl)benz[d]thiazole-5,6-diol ([$^{11}$C]PBB4)

[$^{11}$C]PBB4 was synthesized according to the same method as the methods shown in synthesis examples 42 and 43 above.

Synthesis Embodiment 45

Synthesis of 2-((1E, 3E)-4-(4-(dimethylamino)phenyl)buta-1, 3-dienyl)-3-ethyl-6-[$^{11}$C] methoxybenzo[d]thiazole-3-ium ([$^{11}$C] mPBB5)

Synthesis Scheme

[Formula 70]

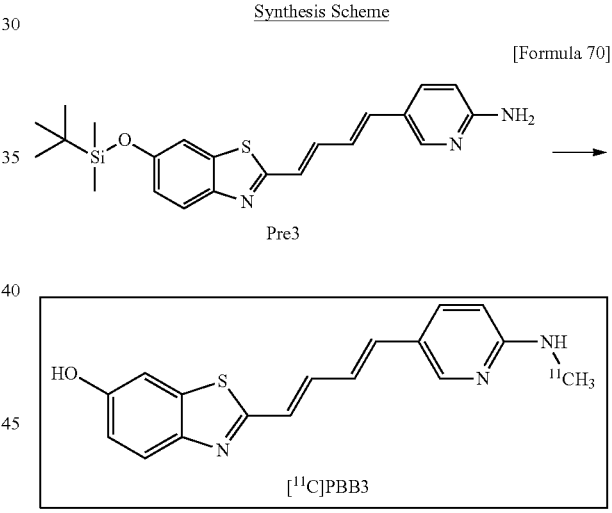

Iodo[$^{11}$C]methane was added, at −15° C., in a DMF (300 μL) solution, which contained 2-((1E,3E)-4-(4-(dimethylamino)phenyl)buta-1,3-dienyl)-3-ethyl-6-hydroxy-benz[d]thiazole-3-ium (pre6) (0.8 to 0.9 mg) and sodium hydride (0.3 mg). The reaction liquid mixture was heated to 80° C., and maintained for 5 minutes. A 60% methanol aqueous solution (800 μL) was added, and the resultant mixture was moved to a HPLC purifying container (HPLC: CAPCELL PAK C18 column, 10 mm×250 mm, mobile phase, methanol/water/trifluoroacetic acid=600/400/0.1, 4 mL/minute). The fractions to match [$^{11}$C]mPBB5 were collected in a flask, which contained, in ethanol (300 μL), 25% ascorbic acid (100 μL) and Tween80 (75 μL), and the solvent was distillated under reduced pressure. The residue was dissolved in physiological saline water (3 mL, pH 7.4), and [$^{11}$C]mPBB5 (300-560 GBq) was obtained as an injection solution.

Synthesis Embodiment 46

Synthesis of (E)-2-(4-(4-(N-[$^{11}$C]methyl-N-methyl-amino)phenyl)buta-1-en-3-ynyl)benz[d]thiazole-6-ol ([$^{11}$C]PBB2.1)

[$^{11}$C]PBB2.1 was synthesized from pre7 by the same method as the methods shown in synthesis examples 42 and 43 above.

Synthesis Embodiment 47

Synthesis of (E)-2-(4-(4-([$^{11}$C]methylamino)phenyl (buta-1-en-3-ynyl)benz[d]thiazole-6-ol ([$^{11}$C]PBB2.2)

[$^{11}$C]PBB2.2 was synthesized from pre8 by the same method as the methods shown in synthesis examples 42 and 43 above.

Synthesis Embodiment 48

Synthesis of (E)-2-(4-(6-(N-[$^{11}$C]methyl-N-methyl-amino)pyridine-3-yl)buta-1-en-3-ynyl)benz[d]thiazole-6-ol ([$^{11}$C]PBB3.1)

[$^{11}$C]PBB3.1 was synthesized by the same method as the methods shown in synthesis examples 42 and 43 above.

Synthesis Embodiment 49

Synthesis of (E)-2-(4-(6-([$^{11}$C]methylamino)pyridine-3-yl)buta-1-en-3-ynyl)benz[d]thiazole-6-ol ([$^{11}$C]PBB3.2)

[$^{11}$C]PBB3.2 was synthesized from pre11 by the same method as the methods shown in synthesis examples 42 and 43 above.

Synthesis Embodiment 50

Synthesis of (E)-5-(4-(6-(aminomethyl)benz[d]thiazole-2-yl)buta-3-en-1-ynyl)-N-[$^{11}$C]meth ylpyridine-2-amine ([$^{11}$C]PBB3.2N)

[$^{11}$C]PBB3.2N was synthesized from pre12 by the same method as the methods shown in synthesis examples 42 and 43 above.

Synthesis Embodiment 51

Synthesis of (2-((1E,3E)-4-(4-aminophenyl)buta-1,3-dienyl)-6-[$^{11}$C]methoxybenzo[d]thiazole-5-ol ([$^{11}$C]Core1-4)

[$^{11}$C]Core1-4 was synthesized by the same method as the method shown in synthesis example 45 above.

Synthesis Embodiment 52

Synthesis of N-(4-((1E,3E)-4-(5-methoxy-6-[$^{11}$C]methoxybenzo[d]thiazole-2-yl)buta-1,3-dienyl)phenyl)acetamide ([$^{11}$C]Core1-5)

[$^{11}$C]Core1-5 was synthesized by the same method as the method shown in synthesis example 45 above.

Synthesis Embodiment 53

Synthesis of (3-(4-(1E,3E)-4-(5-methoxy-6-[$^{11}$C]methoxybenzo[d]thiazole-2-yl)buta-1,3-dienyl)phenylamino)propan-1-ol ([$^{11}$C]Core1-11)

[$^{11}$C]Core1-11 was synthesized by the same method as the method shown in synthesis example 45 above.

Synthesis Embodiment 54

(Synthesis of 4-((1E,3E)-4-(5-methoxy-6-[$^{11}$C]methoxybenzo[d]thiazole-2-yl)buta-1,3-dienyl)-N-isopropylaniline ([$^{11}$C]Core1-15)

[$^{11}$C]Core1-15 was synthesized by the same method as the method shown in synthesis example 45 above.

Synthesis Embodiment 55

Synthesis of 4-((1E,3E)-4-(5-methoxy-6-[$^{11}$C]methoxybenzo[d]thiazole-2-yl(buta-1,3-dienyl)-N-(hepta-1,6-diene-4-ypaniline ([$^{11}$C]Core1-20)

[$^{11}$C]Core1-20 was synthesized by the same method as the method shown in synthesis example 45 above.

Synthesis Embodiment 56

Synthesis of N-(5-((1E,3E)-4-(5-methoxy-6-[$^{11}$C]methoxybenzo[d]thiazole-2-yl)buta-1,3-dienyl)pyridine-2-yl)acetamide ([$^{11}$C]Core2-9)

[$^{11}$C]Core2-9 was synthesized by the same method as the method shown in synthesis example 45 above.

Synthesis Embodiment 57

Synthesis of 3-(5-((1E,3E)-4-(5-methoxy-6-[$^{11}$C]methoxybenzo[d]thiazole-2-yl)buta-1,3-dienyl)pyridine-2-ylamino)propan-1-ol ([$^{11}$C]Core2-10)

[$^{11}$C]Core2-10 was synthesized by the same method as the method shown in synthesis example 45 above.

Synthesis Embodiment 58

Synthesis of N,N-diallyl-5-((1E,3E)-4-(5-methoxy-6-[$^{11}$C]methoxybenzo[d]thiazole-2-yl)buta-1,3-dienyl)pyridine-2-amine ([$^{11}$C]Core2-14)

[$^{11}$C]Core2-14 was synthesized by the same method as the method shown in synthesis example 45 above.

Synthesis Embodiment 59-1

Synthesis of 1-[$^{18}$F]fluoro-2-(24(1E,3E)-4-(6-(dimethylamino)pyridine-3-yl)buta-1,3-dienyl)benz[d]thiazole-6-yloxy)-hydroxymethyl-ethane (Analog of [$^{18}$F]F0-PBB3)

A [$^{18}$F]F0-PBB3 analog could be synthesized from a synthetic intermediate of a F0-PBB3 analog (see Table 2).

Synthesis Embodiment 59-2

Synthesis of 1-[$^{18}$F]fluoro-3-(2-((1E,3E)-4-(6-(methylamino)pyridine-3-yl)buta-1,3-dienyl)benz[d]thiazole-6-yloxy)propan-2-ol ([$^{18}$F]F0-PBB3)

[$^{18}$F]F0-PBB3 can be synthesized from pre21.

Synthesis Embodiment 60

Synthesis of (E)-1-[$^{18}$F]fluoro-3-(2-(4-(6-(methylamino)pyridine-3-yl)buta-1-en-3-ynyl)benz[d]thiazole-6-yloxy)propan-2-ol ([$^{18}$F]F0-PBB3.2)

[$^{18}$F]F0-PBB3.2 can be synthesized from pre22.

Synthesis Embodiment 61

Synthesis of 2-((1E,3E-4-(2-[$^{18}$F]fluoro-6-(methylamino)pyridine-3-yl)buta-1,3-dienyl)benz[d]thiazole-6-ol ([$^{18}$F]F1-PBB3)

[$^{18}$F]F0-PBB3.2 can be synthesized from pre23.

Synthesis Embodiment 62

Synthesis of (0-2-(4-(2-[$^{18}$F]fluoro-6-(methylamino)pyridine-3-yl(buta-1-en-3-ynyl)benz[d]thiazole-6-ol ([$^{18}$F]F1-PBS3.2)

[$^{18}$F]F1-PBB3.2 can be synthesized from pre24.

Synthesis Embodiment 63

Synthesis of 2-((1E,3E)-4-(2-[$^{18}$F]fluoro-6-(methylamino)pyridine-3-yl)buta-1,3-dienyl)benzofuran-5-ol ([$^{18}$F]F1-PBBf3)

[$^{18}$F]F1-PBBf3 can be synthesized from pre25.

Synthesis Embodiment 64

Synthesis of (E)-2-(4-(2-[$^{18}$F]fluoro-6-(methylamino)pyridine-3-yl(buta-1-en-3-ynyl(benzofuran-5-ol ([$^{18}$F]F1-PBBf3.2)

[$^{18}$F]F1-PBBf3.2 can be synthesized from pre26.

Synthesis Embodiment 65

Synthesis of 2-4(1E,3E)-4-(6-(N-[$^{11}$C]methyl-N-methylamino)pyridine-3-yl(buta-1,3-dienyl)quinoline-6-ol ([$^{11}$C]PBQ3.0)

[$^{11}$C]PBQ3.0 was synthesized by the same method as the methods shown in synthesis examples 42 and 43 above.

Synthesis Embodiment 66

Synthesis of 24(1E,3E)-4-(6-([$^{11}$C]methylamino)pyridine-3-yl)buta-1,3-dienyl)quinoline-6-ol ([$^{11}$C]PBQ3)

[$^{11}$C]H3Q3 was synthesized by the same method as the methods shown in synthesis examples 42 and 43 above.

Synthesis Embodiment 67

Synthesis of (E)-2-(4-(6-(N-[$^{11}$C]methyl-N-methylamino)pyridine-3-yl)buta-1-en-3-ynyl)quinoline-6-ol ([$^{11}$C]PBQ3.1)

[$^{11}$C]PBQ3.1 was synthesized by the same method as the methods shown in synthesis examples 42 and 43 above.

Synthesis Embodiment 68

Synthesis of (E)-2-(4-(6-([$^{11}$C]methylamino)pyridine-3-yl(buta-1-en-3-ynyl)quinoline-6-ol ([$^{11}$C]PBQ3.2)

[$^{11}$C]PBQ3.2 was synthesized by the same method as the methods shown in synthesis examples 42 and 43 above.

Biological Embodiments (Compounds and Reagents)

BSB and FSB were purchased from Doujindo. PIS and FDDNP were purchased from ABX. Dimethylamino-styryl-benzothiazole and thioflavine-T were purchased from Sigma-Aldrich. Thioflavine-S was purchased from Waldeck. BF-227, BF-158, THK523, and BF-189 (N-methyl-4-[6-(quinoline-2-yl)hexa-1,3,5-trienyl]aniline) were provided from Tohoku University. Another β-sheet binding compound, which contained PBB5, BTA-1, BF-170, and curcumin, was purchased from Sigma-Aldrich. A potential amyloid ligand which contained cyanine, pyridine, pyridinium, benzothiazole, oxazine, thionine, and polyphenol, was purchased commercially. Dimethylsulfoxide (DMSO) was purchased from Sigma-Aldrich. Other chemical reagents were purchased commercially.

(Animal Models)

Human T34 (4-repeat tau isoform having one N-terminal insertion) hetero Tg mice (also referred to as "PS19 mice"), which were driven by a mouse prion protein promoter (PrP) and which had a FTDP-17 P301S mutation were provided from the University of Pennsylvania. The PS19 mice were backcrossed to a C57BL/6 background. Regarding the PS19 mice, reference may be made to Yoshiyama, Y. et al. Synapse loss and microglial activation precede tangles in a P301S tauopathy mouse model. Neuron 53, 337-351 (2007). All the mice were managed and handled in accordance with "National Research Council's Guide for the Care and Use of Laboratory Animals" and the facility guidelines of the present inventors. This animal experiment protocol has been authorized by the Animal Ethics Committees of the National Institute of Radiological Sciences.

(Dissected Brain Tissues)

Postmortem human brains were obtained from autopsies performed on an Alzheimer's disease (AD) patient, a Pick's disease patient, a progressive supranuclear palsy patient, a corticobasal degeneration patient, and a frontotemporal lobar degeneration patient having ubiquitin-positive and tau-negative inclusions. Tissues were fixed in 10% neutral buffered formalin, and embedded in paraffin blocks. Also, brains were sampled from the mice, and fixed in a phosphate buffer solution containing 4% paraformaldehyde. The tissue samples were cryo-preserved with a phosphate buffer solution containing 30% sucrose, and sliced inside a cryostat (HM560; Carl Zeiss).

Biological Embodiment 1

(In Vitro Fluorometric Binding Assay)

Aβ40 fibrils were obtained by incubating synthetic peptides (Peptide Institute) at 37° C. for 72 hours. Recombinant T40 proteins were fiberized by incubating at 37° C. for 72 hours with 0.1 mg/ml of heparin. Synthetic Aβ peptides (Peptide Institute) were dissolved in phosphate buffered physiological saline water (PBS; pH 7.4) such that the final concentration would become 100 μM, and the resultant solution was incubated at 37° C. for 72 hours. The resulting solution was diluted to 50 μM, and an equivalent amount of compound (PBS containing 0 to 0.5 mM of 1% DMSO) was added. After reacting at 37° C. for 1 hour, the samples were evaluated using a microplate spectrometer (Safire; Tecan). Human T40 was expressed in *Escherichia coli* DE3, refined, and dialyzed against a 30 mM Tris-HCl buffer solution (pH 7.5). Recombinant tau proteins (1 mg/ml) that were separated by reverse-phase HPLC were self-polymerized in a 30 mM Tris-HCl buffer solution containing heparin (0.1 mg/ml), at 37° C., for 72 hours. After that, the tau fibrils (1 μM) were reacted with an equivalent amount of compounds according to the present invention, and the resultant mixture was evaluated in the same way as the analysis of binding to Aβ40. Regarding the fluorometric data, the binding saturation curve was created and the parameter estimation method was conducted using Prism software (GraphPad).

(Result)

The high affinity of PBB1 and PBB5 to tau pathologies was made clear by a fluorometric analysis using Aβ and tau filaments formed in a test tube.

TABLE 3

Table: Fluorescence and binding properties to synthetic Aβ peptides and recombinant protein associations

| Compound | $\lambda_{ex}$ & $\lambda_{em}$ (nm) | | $EC_{50}$ (nM) | | $EC_{50}$ (Aβ)/ $EC_{50}$ (Tau) |
|---|---|---|---|---|---|
| | Aβ40 | T40 | Aβ40 | T40 | |
| Thioflavin-T | 445 & 495 | 445 & 485 | 1,463 ± 459 | 818 ± 231 | 1.8 |
| PBB5 | 635 & 685 | 630 & 685 | 1,217 ± 850 | 126 ± 67 | 9.7 |
| PBB1 | 440 & 565 | 515 & 565 | 4,109 ± 764 | 402 ± 352 | 10.2 |

In this table, $\lambda_{ex}$ and $\lambda_{em}$ are respectively the optimal excitation wavelength and the detection wavelength in fluorescence microscopy measurement of compounds that are bound to Aβ40 and T40 (the longest tau isoform formed with 441 amino acid residues) polymers. $EC_{50}$ (average±SE) is the effective concentration of the compounds, at which the maximum fluorescence intensity at the saturation point decreases by half. The ratio of the $EC_{50}$ of the Aβ40 fibrils to the $EC_{50}$ of the T40 fibrils is shown in the rightmost column in the table.

Biological Embodiment 2

(In Vitro and Ex Vivo Fluorescence Microscopy Measurement, and Ex Vivo Multi-Photon Imaging)

6 μm paraffin sections from patients' brains, and 20 μm frozen sections from mouse brains were stained with 10% compounds (PIB, BF-158, FDDNP, BF-227, PBB1, PBB2, PBB3, PBB4, PBB5, curcumin, FSB, thioflavin-S, and BF-189) dissolved in 50% ethanol, at room temperature, for 1 hour. Images of fluorescence signals from these compounds were picked up using a non-laser microscope (BZ-9000; Keyence Japan) and a confocal laser microscope (FV-1000; Olympus). In confocal imaging, the excitation/emission wavelengths (nm) for each compound were optimized as follows: 405/420-520 (PBB3, FSB, PIB, BF-227, BF-158, FDDNP, thioflavin-S), 488/520-580 (PBB2, PBB4), 515/530-630 (PBB1, curcumin), and 635/645-720 (PBB5, BF-189, DM-POTEB). Following this, test samples and neighboring sections were processed by an autoclave for antigen activation, immuno-stained with AT8 (Endogen) and an anti-Aβ N3 (pE) (pyroglutamylated Aβ3-x) polyclonal antibody, and analyzed using the microscopes. For ex vivo imaging, PS19 mice and non-Tg WT mice, 10 to 12-month old, were anesthetized with 1.5% (v/v) isoflurane, and 1 mg/kg of PBB1 to PBB4, 0.1 mg/kg of PBB5, or 10 mg/kg of FSB were administered in the caudal vein. 60 minutes after the administration, the mice were decapitated. Brain and spinal cord tissues were sampled, and cut into thin sections that were 10 μm thick, in a cryostat (HM560). The sections were imaged using the microscopes, labeled with FSB or AT8, and images were obtained again by the microscopes.

Ex vivo multi-photon imaging was performed as follows. The PS19 mice were given an intravenous injection of 1 mg/kg of PBB2 and PBB4, dissolved in 100 μl of physiological saline water containing 20% DMSO, and, 60 minutes after the administration, the brain and spinal cord were extracted. After that, using a multi-photon laser light-receiving imaging system, a spinal cord sample was tested using 2-photon fluorescence that was generated from a pulse laser (Mai Tai; Spectra-Physics) in 800-nm excitation. The detection wavelength was made 540 to 590 nm.

(Result)

FIGS. 1A-1B and FIG. 2 show fluorescence images of sections of an AD brain having senile plaques and tau pathologies and a non-AD tauopathy brain characterized by tau aggregations but lacking senile plaques. In the AD brain, PBB1 to PBB5 strongly labeled NFTs, neuropil threads, and plaque neurites around senile plaques (FIG. 1), and furthermore strongly labeled Pick bodies in Pick's disease, and tau aggregates in non-AD tauopathies such as neurological and glial fibrous lesions in progressive supranuclear palsy (PSP) and corticobasal degeneration (CBD) (FIG. 2). On the other hand, the compounds other than PBB1 to PBB5 provided insufficient labeling of these (FIGS. 1A-1B and FIG. 2). Note that conventional amyloid stain thioflavin-S and FSB are known to have difficulty passing the blood brain barrier (literature by Zhuang, Z. P. et al., Radioiodinated styrylbenzenes and thioflavins as probes for amyloid aggregates. J. Med. Chem. 44, 1905-1914 (2001).).

Figure 3A:
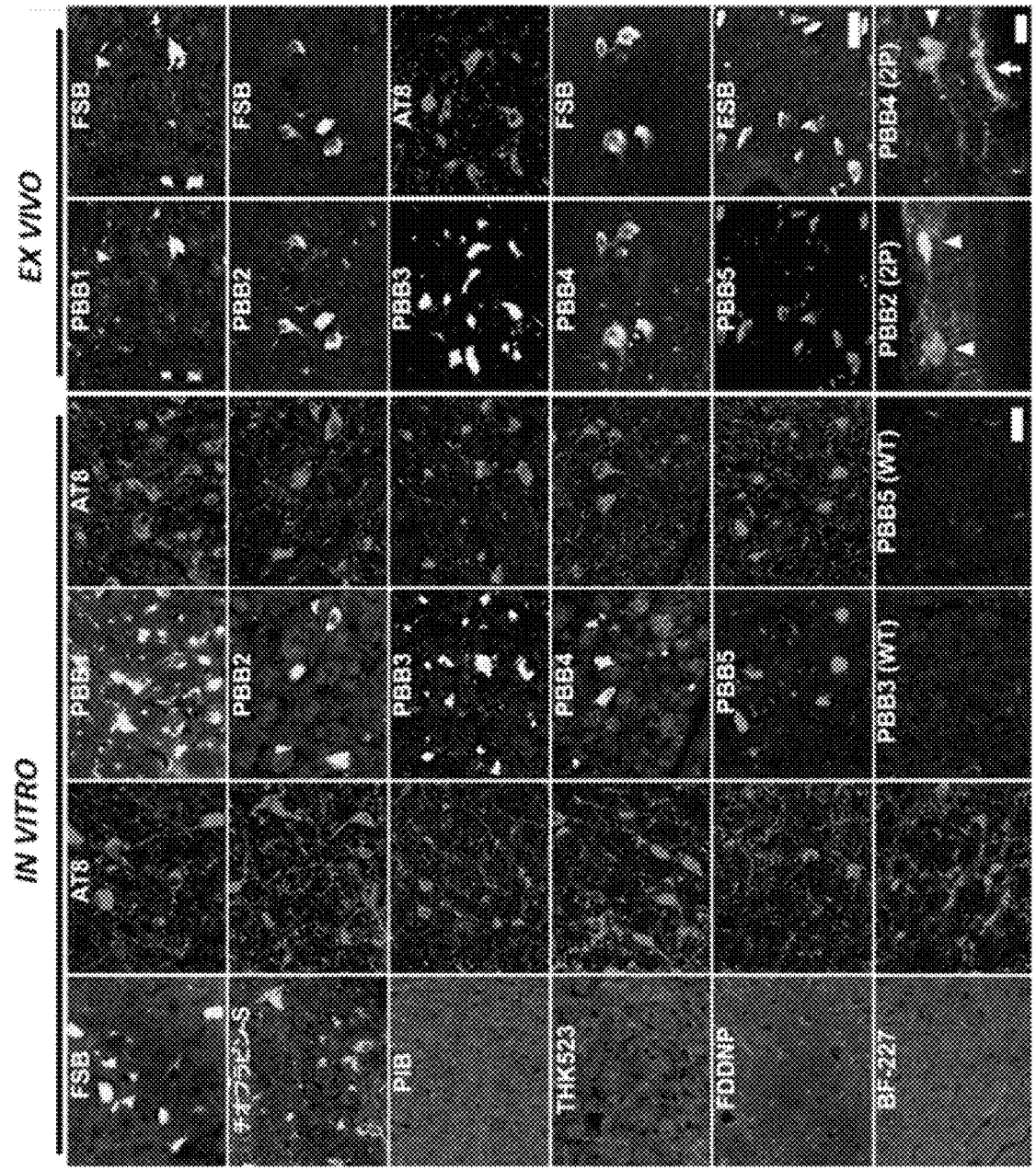
FIG. 3A shows the results of in vitro and ex vivo labeling of NFT-like tau inclusions in PS19 mice using PBB1 to PBB5.
Figure 5A:
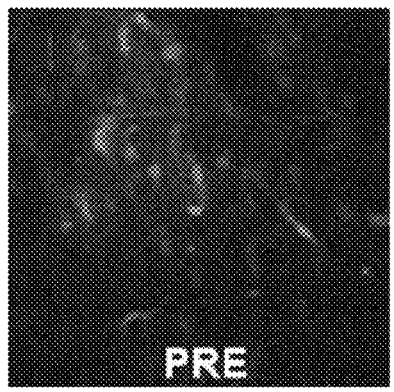
FIGS. 5A, 5B, 5C, 5D, 5E, 5F, 5G, 5H, and 5I show real-time 2-photon laser scanning images of PBB3 distribution at 0, 5, 20, 40, 80, 150, 300 and 600 seconds after injection, respectively.
Figure 5B:
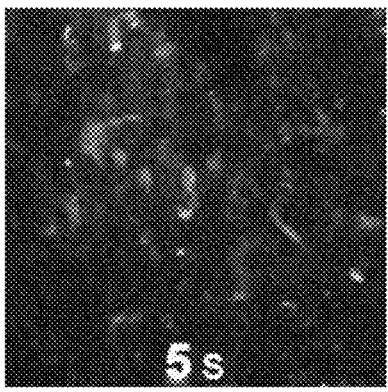
Figure 5C:
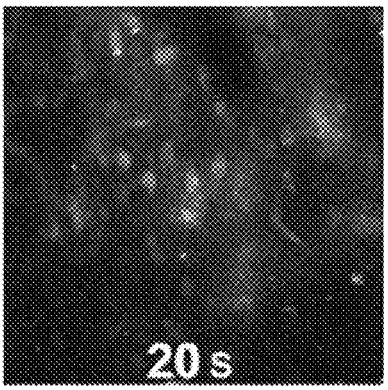
Figure 5D:
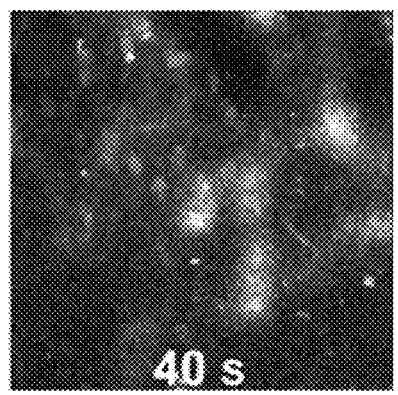
Figure 5E:
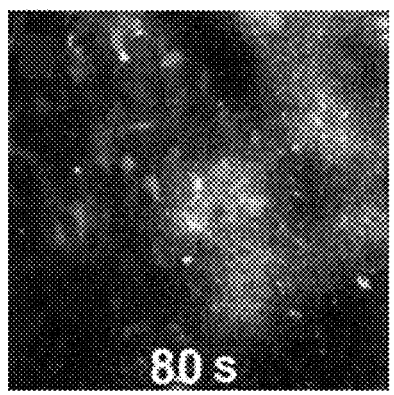
Figure 5F:
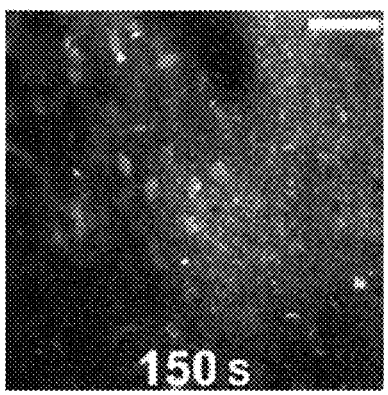
Figure 5G:
Figure 5H:
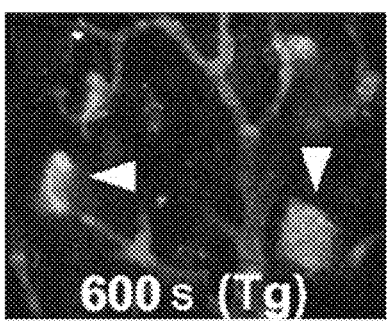
Figure 5I:
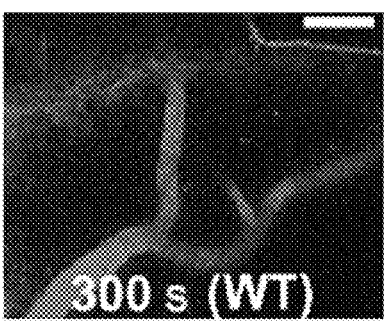

FIG. 3A shows in vitro and ex vivo labeling results of NFT-like tau inclusions in the PS19 mice using PBB1 to PBB5. Similar to the fluorescent labeling result of tau pathologies in the non-AD tauopathy brain, although the NFT-like inclusions in the brain stems and spinal cords of the PS19 mice were clearly identified with PBB1 to PBB5, these were not identified by other compounds that have been used in PET imaging heretofore ("in vitro" in FIG. 3A). In ex vivo labeling, although FSB was found to bind to tau accumulations in the PS19 mice ("in vivo" in FIG. 3A), a large amount of administration was necessary for this. To match these observation results, the 2-photon laser scanning fluorescence microscopic examination results of the ex vivo sample showed that the spinal cord block of the PS19 mice was labelled with PBB2 and PBB4 (the lowermost row in "in vivo" of FIG. 3A). These results shown above indicate that the PBB compounds are sufficiently capable of passing the blood brain barrier and cell membranes. As for the other compounds, in vitro experiments, which were the same as the above-described experiments performed on PBB1 to PBB5, were conducted, and the same results were achieved. These results are shown in FIG. 3B.

Biological Embodiment 3

(Non-Invasive Near Infrared Fluorescence Imaging of Tau Accumulations in Living Mouse Bodies)

(In Vivo and Ex Vivo Pulse Laser Scanning Imaging)

Non-invasive scanning of 12-month-old non-Tg WT mice and tau Tg mice, anesthetized with isoflurane, was performed using a small animal-dedicated optical imager (eXplore Optix; ART). Fluorescence was generated from a 635-nm pulse laser diode (laser output, 25 to 125 mW, adjusted in each experiment; laser repetition rate, 80 MHz; pulse width, up to 100 ps) and detected with a 650-nm long pass filter and a fast response photomultiplier tube. In each experiment, the distance between the top of the head and the detector was maintained constant by the high-precision vertical motion of the base and the side cameras. The mice were given an intravenous injection of 0.1 mg/kg of PBB5, dissolved in 100 µl of physiological saline water containing 20% DMSO, and the head parts of the mice were scanned, in a step width of 1.0 mm, and in a TPSF integration time of 0.1 to 0.3 seconds (optimized on a per scan basis) per scan position. Dynamic imaging was performed over 240 minutes, comprised of the baseline scan (before the administration), and a plurality of scans performed 5, 10, 15, 30, 45, 60, 90, 120, 180, 240, 300, and 360 minutes after the injection. The fluorescence intensity was standardized between scans in accordance with the laser output and the integration time. For each scan position, a TPSF curve was determined, and the time constant to match the exponential curve was estimated. Also, an ROI-based analysis was performed in parts of the head corresponding to the frontal lobe, the brain stem, and the cervical cord. The brains of these animals were extracted after in vivo assay and fixed with 4% paraformaldehyde, and 20 µm-thick frozen sections were stained with FSB and AT8.

(Result)

FIG. 4A shows a reference autofluorescent signal (center panel) laid over a visible light image (left panel) of the shaved head part of non-Tg WT mice. Elliptically-shaped regions of interest (ROIs) were set in the positions of the frontal cortex (FC), the brain stem (BS), and the cervical cord (SC) (right panel). FIG. 4B shows fluorescence intensity maps of PBB5 (0.1 mg/kg) in 12-month-old WT mice (upper part) and PS19 mice (lower part), before and 30 minutes and 240 minutes after the intravenous administration. The intensity maps were standardized based on the FC ROI values 30 minutes after the injection of PBB5. Near infrared fluorescence increased significantly immediately after the PBB5 was administered, and, in 30 minutes, the fluorescence intensity in the brain stem and spinal cord ROIs in the PS19 mice exceed the intensity in the WT mice. Also, even 240 minutes later, PBB5 signals were observed in the brain stems and spinal cords of the PS19 mice.

FIGS. 4C to 4E show the ratios of fluorescence intensity in the BS (c) and SC (d) ROIs, to the FC ROI, in the WT mice (white: n=7) and the PS19 mice (black: n=7). These ratios were significantly bigger in the WT mice than in the PS19 mice (FIG. 4C and FIG. 4D: 2-way, repeated-measures ANOVA (time, $F_{(11, 132)}=17.6$, $p<0.001$; region, $F_{(1, 12)}=29.9$, $p<0.001$; genotype, $F_{(1, 12)}=23.6$, $p<0.001$; FIG. 4E:*, $p<0.05$; **, $p<0.01$; Bonferroni's post hoc analysis). FIG. 4F shows a distribution diagram of the ratios of SC and BS to FC 240 minutes later, against the number of FSB-positive NFT-like pathologies per unit area of 20-µm tissue sections of the tau Tg mice. The ratio of SC to FC in the PS19 mice 240 minutes later showed a significant correlation with NFT-like tau pathologies in the brain evaluated by FSB staining (FIG. 4F). This formed the basis of the applicability of this ratio to optical measurement as an in vivo indicator of tau accumulations.

FIG. 4G shows the fluorescence intensity (left) and the fluorescence duration (right) in 11-month-old WT mice (upper part) and PS19 mice (lower part) 120 minutes after the intravenous injection of PPB5. The BS and SC ROIs of the tau Tg mice showed extended durations of fluorescence compared to the WT mice (see the arrows). In the FC ROIs of the WT and Tg mice, the fluorescence intensity increased remarkably, but the fluorescence duration thereof did not change much. FIG. 4H shows TPSF curve of SC and FC spots 120 minutes after injection in 11 month-old WT mice and Tg mice. Compared to the WT data, an obvious delay of fluorescence decay was observed in Tg SC.

FIG. 4I shows average durations of fluorescence (*: $p<0.05$; 2-way repeated-measures ANOVA with Bonferroni's post hoc analysis) in the FC, BS, and SC ROIs in the WT mice (white; n=7) and Tg mice (black; n=7) 120 minutes after the injection. FIG. 4J shows a distribution diagram of the fluorescence duration periods in the BS and SC ROIs 120 minutes after the injection, against the number of FSB-positive NFT-like pathologies per unit area in 20 µm-thick tissue sections of the Tg mice. The average fluorescence duration periods in the brain stems and the spinal cords of the PS19 mice increased significantly compared to those of the non-Tg WT mice, and had a significant correlation with the number of NFT pathologies in the BS and SC ROIs. A TPSF curve can be considered to be formed with signals from compounds that are not bound or are bound non-specifically, and that have short fluorescence duration, and tau pathology-binding compounds that have extended fluorescence duration depending on the growth of fibrils, so that the time constant that is determined by fitting this curve to the exponential function is effective as a reasonable reliable indicator of the amount of accumulation of tau aggregates.

Biological Embodiment 4

(In Vivo 2-Photon Laser Scanning Fluorescence Microscopic Examination)

12-month-old WT mice and PS19 mice were anesthetized with 1.5% (v/v) isoflurane, and their thoracic vertebrae were laminectomized. Cover glass was placed over spinal cord tissues, and the vertebral columns were fixed with a Narishige STS-A spinal cord clamp and a MA-6N head-fixing adaptor. 12 mg/kg of sulforhodamine 101 (MP Biomedicals) was administered intraperitoneally, and, 15 minutes later, 1 mg/kg of PBB3 was administered intravenously, and biological 2-photon fluorescence imaging was performed. The detection wavelengths for PBB3 and sulforhodamine 101 were made 500 to 550 nm and 573 to 648 nm, respectively.

(Result)

FIGS. 5A through 5I show real-time 2-photon laser scanning images. Within 3 seconds after the injection of PBB3, PBB3 signals appeared in blood vessels that had been labeled in advance with sulforhodamine 101, and, in the next 5 minutes, the signals spread from the blood vessels to spinal cord tissues (FIG. 5A to FIG. 5F). After that, although PBB3 that was not bound was discharged from the spinal cord tissues, at the same time, clear binding to tau inclusions (FIG. 5G and FIG. 5H, cuneiform symbols) was shown. On the other hand, in the WT mice, such signals to originate from binding compounds were not observed. This result indicates that PBB3 passes the blood brain barrier and quickly labels the tau deposits in the brain.

Biological Embodiment 5

(Autoradiography and PET Imaging of Tau Pathologies in PS19 Mice by Radio-Labeled Compounds)
(In Vitro Autoradiography)

12 to 15-month-old non-Tg WT mice and PS19 mice were decapitated, and their brains were frozen and sliced into 20 μm-thick sections in a cryostat (HM560). The sections were placed on slide glass (Matsunami Glass), and kept at −80° C., until an analysis. Similarly, sections of the cerebral cortex were obtained from an AD patient. Tissue sections were incubated for at room temperature for 60 minutes, in a 250 mM Tris-HCl buffer solution (pH 7.4), containing 20% ethanol and [$^{11}$C]PBB2, or 10% ethanol and [$^{11}$C]PBB3 (37 MBq/L, up to 1 nM). Non-specific bonding was detected in the presence of a 10 μMV non-radioactive ligand. Samples were reacted with [$^{11}$C]PBB2 or [$^{11}$C]PBB3, and were each washed twice, for 2 minutes, with an ice-cool Tris-HCl buffer solution containing 20% or 10% ethanol, and immersed in ice water for 10 seconds. After that, the sections were dried with warm air, and placed on imaging plates (Fuji Film). The imaging plates were scanned by a BAS500 system (Fuji Film), and autoradiograms were obtained (FIG. 6A).

(Ex Vivo Autoradiography)

Under anesthesia with a 1 to 1.5% (v/v) isoflurane mixture (flow rate 2 mL/minute), [$^{11}$C]PBB2 or [$^{11}$C]PBB3 (up to 37 MBq) was injected in the caudal veins of 12 to 15 month-old non-Tg WT mice and PS19 mice. 45 minutes after the injection, the mice were decapitated, and their brains were quickly extracted and frozen with powder dry ice. The frozen brain tissues were cut into 20 μm-thick sections with a cryotome. After that, autoradiograms were obtained (FIG. 6B). Also, the brain sections of the PS19 mice after autoradiography were stained with FBS.

(In Vivo PET (Positron Emission Tomography) Imaging of Mice)

PET scanning was performed using a micro PET focus 220 animal scanner (Siemens Medical Solutions), which provided 95 slices that were 0.851 mm-thick (between centers), a 19.0-cm axial field of view (FOV) and a 7.6-cm cross-sectional FOV. Before scanning, 9 to 15-month-old PS19 mice and non-Tg WT mice were anesthetized with 1.5% (v/v) isoflurane. An emission scan was performed immediately after the intravenous injection of [$^{11}$C]PBB2 (28.3±10.3 MBq), [$^{11}$C]pBB3 (29.7±9.3 MBq), or [$^{11}$C]mPBB5 (32.8±5.9 MBq), for 90 minutes, in 3D list mode, with an energy window 350-750 keV. The injection of the radioactive compound and scanning were conducted under dim light so as to avoid photoracemization of the compound. The entire list mode data was sorted into 3D sinograms, and, after that, converted into 2D sinograms by Fourier-rebining (frame: 10×1, 6×5, and 5×10 minutes). Arithmetic mean images from 30 to 60 minutes and 60 to 90 minutes after the injection of the radioactive compound were obtained by maximum a posteriori reconstruction. Also, dynamic images were reconstructed by filtered back projection, using a 0.5-mm Hanning filter. The volume of interest (VOI) was set in a plurality of anatomical structures, including the brain stem and the striatum, using PMOD image analysis software (PMOD Technologies), with reference to an MRI template.

With a subgroup of 12 month-old PS19 Tg mice that were subjected to [$^{11}$C]PBB3-PET scanning, TSPO dynamic PET imaging was performed over 90 minutes after an intravenous injection of [$^{11}$C]Ac5216 (34.6±8.8 MBq). [$^{11}$C]Ac5216-PET scanning was performed within one week after the [$^{11}$C]PBB3-PET scanning (FIG. 6C).

(Result)

FIG. 6A shows in vitro autoradiograms of the cerebellar brain stem parts and the AD frontal cortexes of the PS19 and non-Tg WT mice. With [$^{11}$C]PBB2 and [$^{11}$C]PBB3, fibrous aggregate pathologies in the brain stems and AD grey matters of the mice were strongly radio-labeled. Also, binding of [$^{11}$C]PBB3 was blocked by addition of non-radioactive PPB3 (10 μM). FIG. 6B shows ex vivo autoradiogram of the PS19 and non-Tg WT mice, and FBS stain image diagrams of the PS19 brain slice. The arrows indicate the brain stems containing many tau inclusions. With [$^{11}$C]PBB2 and [$^{11}$C]PBB3, tau inclusions contained in the brain stem and spinal cord of the PS19 mice were radio-labeled. [$^{11}$C]PBB3 radio-labeled tau inclusions more selectively.

FIG. 6C shows sagittal-plane and coronal-plane PET images and MRI images, obtained by averaging the dynamic scan data from 60 to 90 minutes after the intravenous administration of [$^{11}$C]PBB3. The arrows and the asterisks show the brain stem and the striatum, respectively, and the cuneiform symbol shows strong radiolabeling in the inner brain stem of the PS19 mice. FIGS. 6A and 6B show sagittal section PET images obtained by averaging dynamic scan data 60 to 90 minutes after the administration of [$^{11}$C]PBB2. Tau pathologies of the PS19 mice were successfully visualized in vivo.

FIG. 6D shows FSB stain images of a brain section extracted from the PS19 mice after PET scanning (a sagittal plane image (left panel) and a coronal plane image (center panel), and a high-magnification image (right panel)) of fibrous tau inclusions. It is shown that the topographies of PET signals and NFT-like tau inclusions match in the PS19 mice.

FIG. 6E shows the time-activity curves (left panel) in the striatums (ST) and brain stem (BS) of the PS19 mice and WT mice, and, the BS-to-ST ratios of radioactivity (right panel) (in each, n=5). After the intravenous injection, [$^{11}$C]PBB3 passed the blood brain barrier quickly, and [$^{11}$C]PBB3 that was not bound and that was non-specifically bound was immediately removed from the brains at a half-life of approximately 10 minutes. Also, the [$^{11}$C]PBB3 signal in the brain stems of 12-month-old PS19 mice was maintained over the imaging period (90 minutes), and this was significantly different from the result of non-Tg WT mice of the same month age (FIG. 6E, the left panel). The striatum (ST) lacking tau pathologies was used as a reference region, and the ratio of the target brain stem (BS) to that reference region marked the maximum value in approximately 70 minutes (right panel, FIG. 6E). On the other hand, in the WT mice, this kept decreasing over 60 minutes. Compared to 12-month-old WT mice, the average ratio over 45 to 90 minutes increased by 40% in PS19 mice of the same month age.

FIGS. 6H and 6I show ex vivo autoradiography images of the mice shown in FIGS. 6F and 6G. The arrows in the drawings show an increase of radiolabeling in PS19 mice. FIGS. 6J and 6K show FSB stain images, using the same samples as the samples from which the autoradiography images are obtained. FIG. 6L shows time-activity curves in a plurality of brain tissues of WT mice. FIG. 6M shows the ratios of radioactivity in the brain stem to the striatum, in PS19 mice (1 in the drawing) and WT mice (2 in the drawing) (n=5), over the imaging period.

FIG. 7 shows coronal-plane PET images in the brains of the WT mice (left panel) and the PS19 Tg mice (right panel) given an injection of [$^{11}$C]mPBB5. These images were laid over an MRI template by averaging the dynamic data from 30 to 90 minutes after the injection. The PET images show that a lot of [$^{11}$C]mPBB5 was held in the brain stems of the PS mice, compared to the WT mice.

Biological Embodiment 6

(In Vitro Autoradiography of AD Brains Including Human Hippocampal Formations)

In order to compare the binding of [$^{11}$C]PBB3 and [$^{11}$C]PIB to areas inside the human brain where there were plenty of tau pathologies, in vitro autoradiograms were obtained using AD brain slices including the hippocampal formation.

(In Vivo PET Imaging of Humans)

2 subjects with normal cognitive function (72 years old and 75 years old; average 73.5 years old), and 3 AD patients (64 years old, 75 years old and 77 years old; average 72 years old) were employed for this study. All the subjects were males, and all the AD patients were diagnosed in accordance with the standards of the National Institute of Neurological and Communicative Diseases and Stroke/Alzheimer's Disease and Related Disorders Association (NINCDS-ADRDA). The clinical dementia rating scale was 0 for both normal subjects, and ranged from 1 to 2 with the AD patients. Their cognitive function was evaluated by a mini-mental state examination (MMSE). No subject showed MRI-based brain abnormalities. On the other hand, the AD patients exhibited atrophy of the neocortex and the hippocampus. This clinical study had been authorized by the Ethics and Radiation Safety Standards Committee of the National Institute of Radiological Sciences. Informed consent had been obtained from the subjects or from their family. PET assay was performed using a Siemens ECAT EXACT HR+ scanner (CTI PET Systems) with an axial FOV of 155 mm, 63 consecutive 2.46 mm-thick slices, and an axial resolution of 5.4 mm with a tangential resolution of 5.6 mm. In order to measure tissue attenuation, a transmission scan was performed for 10 minutes, and dynamic emission scan data was collected in 3D mode, over 70 minutes immediately after an intravenous injection of [$^{11}$C] PIB (350±50 MBq). A plurality of image frames (3×20, and 3×40 seconds, and 1×1, 2×3, 5×6, and 3×10 minutes) were obtained from that dynamic scan. Similarly, with the same individuals, a second PET session using [$^{11}$C]PBB3 was performed approximately 2.5 hours after [$^{11}$C]PIB-PET was finished. [$^{11}$C]PBB3 (370±50 MBq) was injected in the vein over 60 seconds, and emission data was obtained in 70 minutes (frames: 3×20, and 3×40 seconds, and 1×1, 2×3, 5×6, and 3×10 minutes). During the [$^{11}$C]PBB-PET scanning, artery blood samples are obtained 10, 20, 30, 40, 50, 60, 70, 80, 90, 100, and 110 seconds after the injection, and 2, 2.5, 3, 4, 5, 6, 7, 8, 9, 10, 12, 15, 20, 25, 30, 40, 50, 60 and 70 minutes after the injection, and the amount of radioactivity in the plasma was measured. The radioactivity to match [$^{11}$C]PBB3 in unmetabolized plasma was measured by HPLC using the samples from 3, 10, 20, 30 and 60 minutes after the injection (Waters mBondapak C18 column, 7.8 mm×300 mm; acetonitrile/ammonium formate mobile phase, gradient elution=40/60 (0 minutes), 52/48 (6 minutes), 80/20 (7 minutes), 80/20 (8 minutes), 40/60 (9 minutes) and 40/60 (15 minutes); flow rate, 6 mL/minute). The injection of the radioactive compound and the following scan, and the plasma assay were performed under dim light so as to avoid photoracemization of the compound.

Individual MRI data was recorded simultaneously with PET images, using PMOD software package (PMOD Technologies). VOIs were set in the MR images recorded simultaneously, and moved to the PET images. The VOIs were defined in the cerebellar cortex, the middle temporal area including the parahippocampal gyrus and the hippocampus, the basal part side of the frontal cortex, the precuneus part of the parietal cortex, and the centrum semiovale. Each VOI included three neighboring slices, and, by combining the data, an average radioactivity concentration of all VOIs was obtained. A standardized uptake value (SUV) was calculated from the time-integrated regional radioactivity concentration standardized by the injection dose/weight. The integration interval was set on the data of 30 to 70 minutes. The cerebellum could be used as a reference brain region, so that the SUV ratio (SUVR) of the cerebellum was measured for each target VOI, as an indicator of senile plaques or tau depositions.

(Result)

Figure 8A:
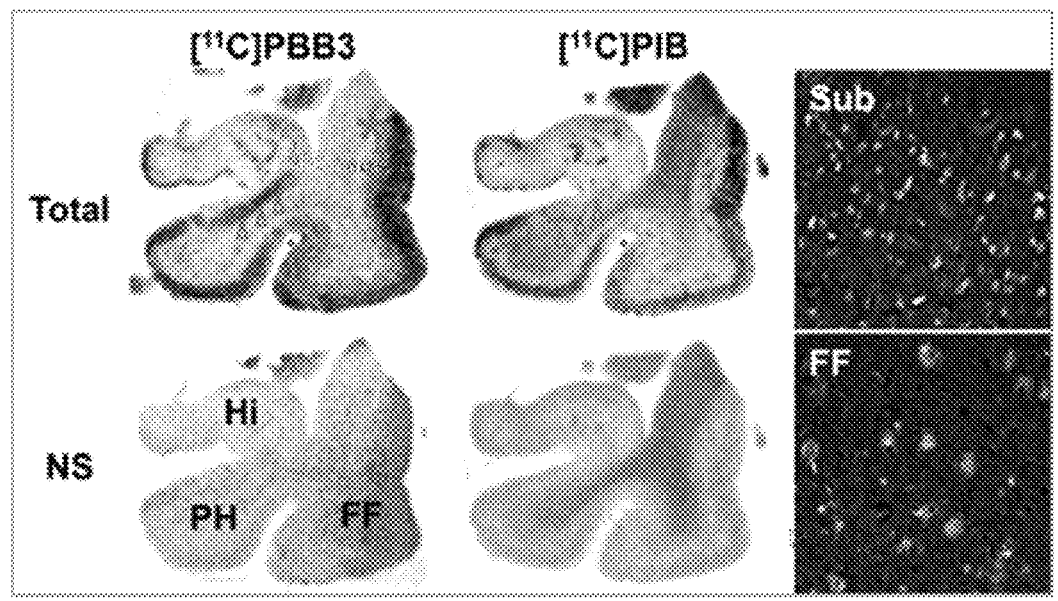
FIG. 8 shows autoradiography images (FIG. 8A) and PET images (FIG. 8B) of brain slices of AD patients using [$^{11}$C]PBB3 and [$^{11}$C]PIB.

FIG. 8A shows autoradiography of an AD patient's brain slice using 10 nM of [$^{11}$C]PBB3 (left) and [$^{11}$C]PIB (center). This section includes the hippocampus (Hi), the parahippocampal gyms (PH), the fusiform gyms (FF), and the white matter (asterisk). Total binding of [$^{11}$C]PBB3 and [$^{11}$C]PIB was clearly discarded, except for the white matter that was labeled with [$^{11}$C]PIB, by addition of non-radioactive PBB5 (100 μM) and thioflavin-S (10 μM) (NS). Strong [$^{11}$C]PBB3 signals were observed in the hippocampus CAI region and the pes hippocampi, but no [$^{11}$C]PIB signal was observed. Also, there was more binding of [$^{11}$C]PBB3 in the cortex region (black dot) in the side of the collateral sulcus, compared to the binding of [$^{11}$C]PIB. The FSB stain of amyloid fibrils in this section showed that there were many NFT pathologies in the CAI and the subiculum (Sub), and that there were many senile plaques in the fusiform gyms (FF) (right panels). This suggests strong reactivity of [$^{11}$C]PBB3 to NFTs in AD brains.

Figure 8B:
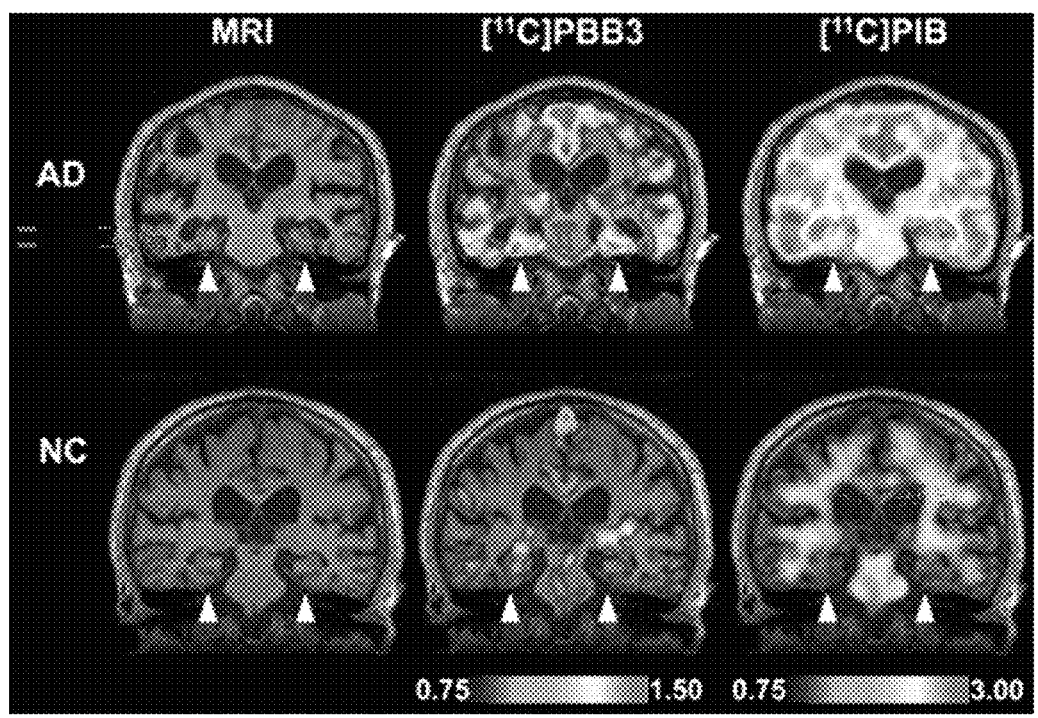

FIG. 8B shows MRI images (left) and PET images using [$^{11}$C]PBB3 (center) and [$^{11}$C]PIB (right), taken from the same AD (upper part) and normal control (NC; lower part) subjects. The coronal section images include the hippocampal formation (cuneiform symbols). Compared to the NC, although the [$^{11}$C]PBB3 signal increased in the hippocampal formation of the AD patient, the [$^{11}$C]PIB signal did not change much. This indicated that, unlike [$^{11}$C]PIB, [$^{11}$C]PBB3 bound strongly with NFTs in the AD patient's hippocampus.

Abbreviations

AD: Alzheimer's disease
AIBN: azobisisobutyronitrile
ATB: anti-phospho-tau antibody
BF-158: 2-[(4-methylamino)phenyl]quinoline
BF-170: 2-(4-aminophenyl)quinoline
BF-189: N-methyl-4-[6-(quinoline-2-yl)hexa-1,3,5-trienyl] aniline
BF-227: 2-(2-[2-dimethylaminothiazole-5-yl]ethenyl)-6-(2-[fluoro]ethoxy)benzoxazole)
BSB: (E,E)-1-bromo-2,5-bis(3-hydroxycarbonyl-4-hydroxy)styrylbenzene
BTA-1: 2-(4-methylaminophenyl)benzothiazole
DM-POTEB: 2-[8-(4-dimethylaminophenyl)octa-1,3,5,7-tetraenyl]-3-ethylbenzothiazole-3-ium FDDNP: 2-(1-{6-[(2-fluoroethyl) (methyl)aminol-2-naphthyl}ethylidyne)malononitrile
FSB: (E,E)-1-fluoro-2,5-bis(3-hydroxycarbonyl-4-hydroxy)styrylbenzene
FTDP-17: frontotemporal dementia linked to chromosome 17 with Parkinsonism
MRI: magnetic resonance imaging
NFT: neurofibrillary tangle
NBS: N-bromosuccinimide
PET: positron emission tomography
PIB: Pittsburgh Compound B
T40: the longest tau isoform formed with 441 amino acid residues
TBDMSC1: tert-butyldimethylchlorosilane
Tg: transgenic
THK523: 2-(4-aminophenyl)-6-(2-fluoroethoxy)quinoline
TSPO: translocator protein
WT: wild type

INDUSTRIAL APPLICABILITY

The compounds of the present invention can be used to clarify the mechanism by which tau proteins to accumulate in the brains of patients of diseases such as Alzheimer's disease, frontotemporal lobar degeneration, dementia, and other neurodegenerative tauopathies are produced. Also, by using the compounds of the present invention, it is possible to diagnose the above diseases, predict future episodes, and perform screening of candidate compounds for treatment of the above diseases. Furthermore, by using the compounds of the present invention, it is possible to plan strategies for treatment of the above diseases.

The invention claimed is:

1. A method for imaging tau proteins that accumulate in the brain, the method comprising the steps of:
   (a) administering to a mammal an effective amount of a compound of the Formula (I), or a pharmaceutically acceptable salt or a solvate thereof, and
   (b) imaging the brain of the mammal,
   wherein the compound of Formula (I) is:

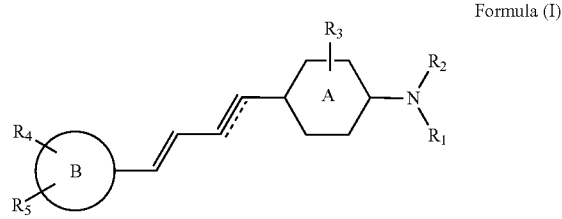

Formula (I)

wherein:
   $R_1$ and $R_2$ are each independently selected from the group consisting of hydrogen, alkyl, alkenyl, acyl, and hydroxyalkyl;
   $R_3$ is hydrogen or halogen;
   ring A is a benzene ring or a pyridine ring;
   ring B is selected from the group consisting of the following formulae (i), (ii), (iii), and (iv):

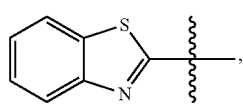

(i)

-continued

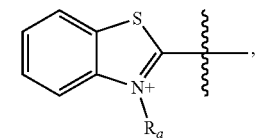

(ii)

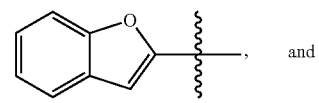

(iii)

and

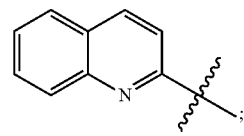

(iv)

in the formula (ii), $R_a$ is alkyl;
$R_4$ and $R_5$ are each independently selected from the group consisting of hydrogen, hydroxy, alkoxy, haloalkoxy, halohydroxyalkoxy, and aminoalkyl; and

===== represents a double bona or a triple bond,
wherein the compound of Formula (I) is not:

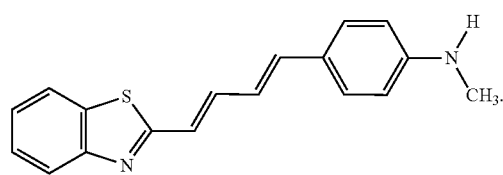 [SMILES: CNc1ccc(/C=C/C=C/c2nc3ccccc3s2)cc1]

2. The method of claim 1, wherein, in the compound, one or more atoms are a radioisotope of the atom or atoms.

3. The method of claim 1, wherein ring B is of formula (i) or (ii).

4. The method of claim 3, wherein the compound is according to Formula

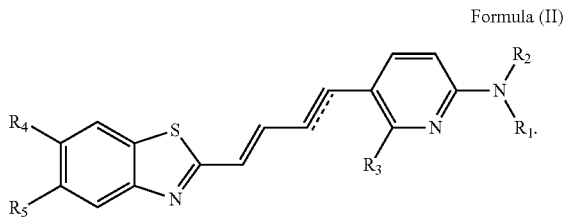

Formula (II)

5. The method of claim 4, wherein, in the compound,

===== represents the double bond.

6. The method of claim 4, wherein, in the compound,

===== represents the triple bond.

7. The method of claim 3, wherein the compound is according to Formula (III):

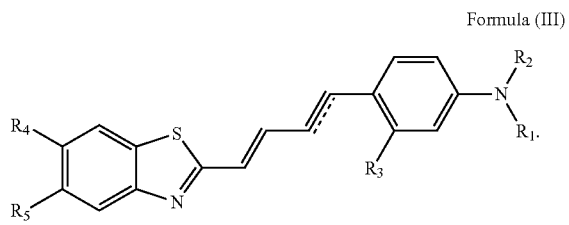

Formula (III)

8. The method of claim 7, wherein, in the compound,

===== represents a double bond.

9. The method of claim 7, wherein, in the compound,

===== represents a triple bond.

10. The method of claim 3, wherein the compound is according to Formula (IV):

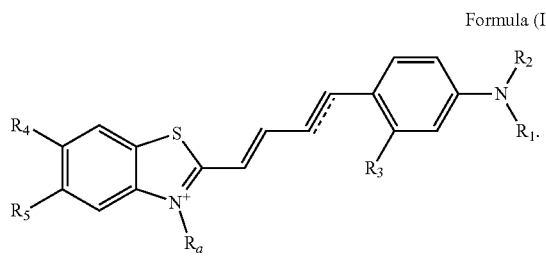

Formula (IV)

11. The method of claim 10, wherein, in the compound,

===== represents a double bond.

12. The method of claim 10, wherein, in the compound,

===== represents a triple bond.

13. The method of claim 1, wherein ring B is of formula (iii).

14. The method of claim 13, wherein the compound is according to Formula (V):

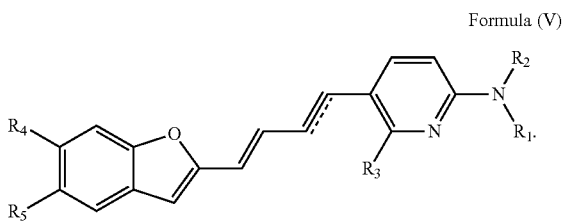

Formula (V)

15. The method of claim 14, wherein, in the compound,

===== represents a double bond.

16. The method of claim 14, wherein, in the compound,

===== represents a triple bond.

17. The method of claim 1, wherein ring B is of formula (iv).

18. The method of claim 17, wherein the compound is according to Formula (VI):

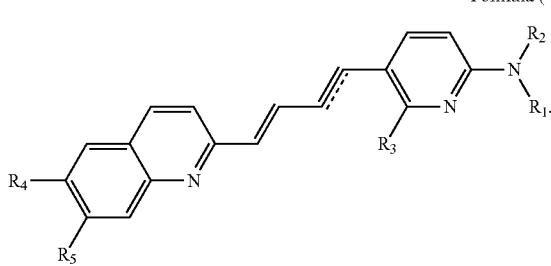

Formula (VI)

19. The method of claim 18, wherein, in the compound,

===== represents a double bond.

20. The method of claim 18, wherein, in the compound,

===== represents a triple bond.

21. The method of claim 1, wherein the compound is selected from the following structural formulae:
| Name | Structural Formula |
|---|---|
| PBB1 | 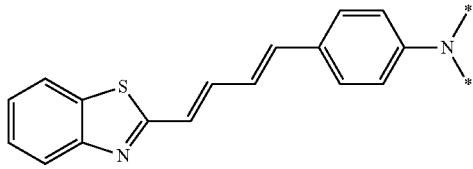 [SMILES: *N(*)c1ccc(/C=C/C=C/c2nc3ccccc3s2)cc1] |
| PBB2 | 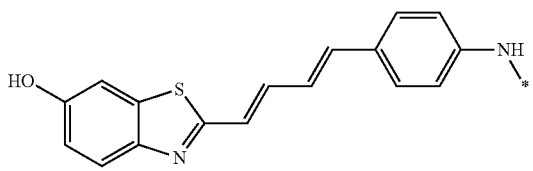 |
| PBB3 | 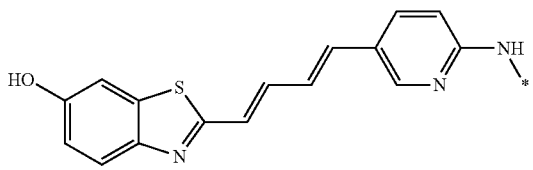 |
| PBB4 | 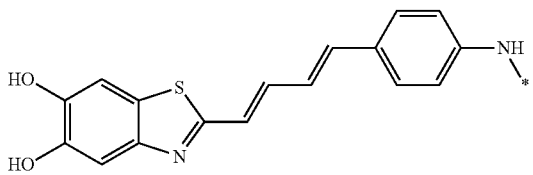 [SMILES: *Nc1ccc(/C=C/C=C/c2nc3cc(O)c(O)cc3s2)cc1] |
| PBB5 | 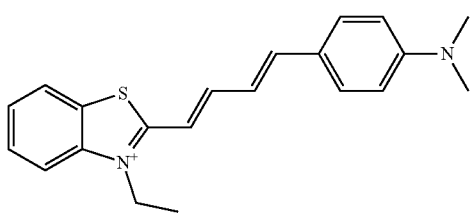 [SMILES: CC[n+]1c(/C=C/C=C/c2ccc(N(C)C)cc2)sc2ccccc21] |
| mPBB5 | 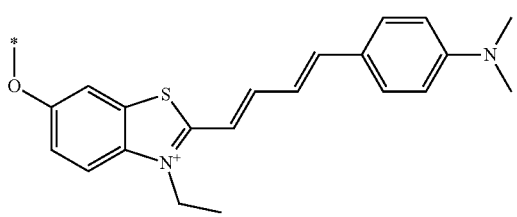 |
| PBB2.1 | 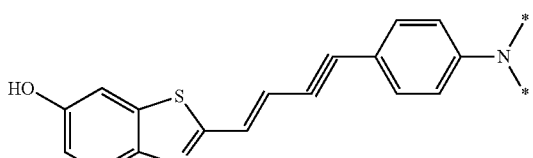 |
| PBB2.2 | 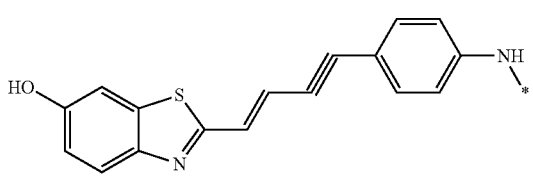 [SMILES: Nc1ccc(C#C/C=C/c2nc3ccc(O)cc3s2)cc1] |

-continued

| Name | Structural Formula |
|---|---|
| PBB2.3 | |
| PBB3.1 | |
| PBB3.2 | |
| PBB3.2N | |
| Core1-4 | |
| Core1-5 | |
| Core1-11 | |
| Core1-15 | |

| Name | Structural Formula |
|---|---|
| Core1-20 | 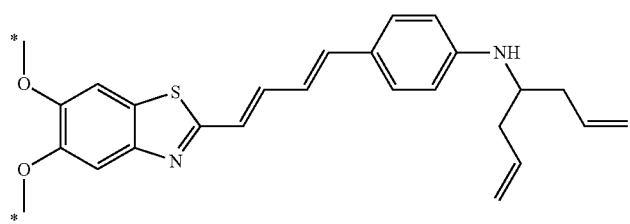 [SMILES: C=CCC(CC=C)Nc1ccc(/C=C/C=C/c2nc3cc(OC)c(OC)cc3s2)cc1] |
| Core2-9 | 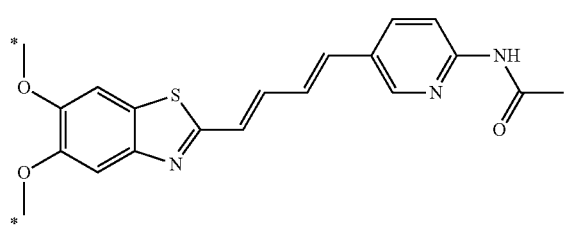 |
| Core2-10 | 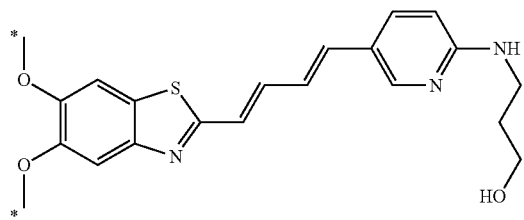 [SMILES: COc1cc2nc(/C=C/C=C/c3ccc(NCCCO)nc3)sc2cc1OC] |
| Core2-14 | 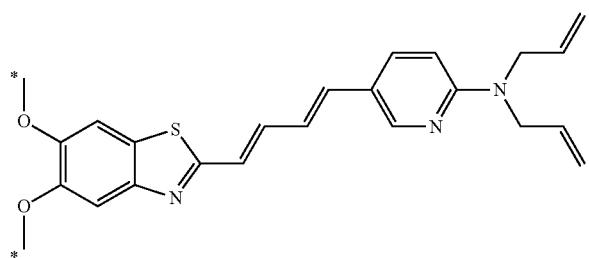 |
| F0-PBB3 analogue | 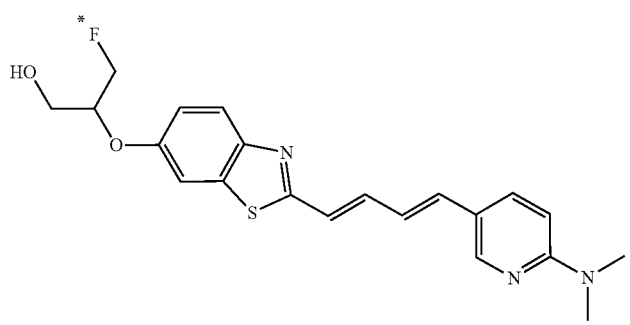 [SMILES: CN(C)c1ccc(/C=C/C=C/c2nc3ccc(OC(CO)CF)cc3s2)cn1] |

-continued
| Name | Structural Formula |
|---|---|
| F0-PBB3 | 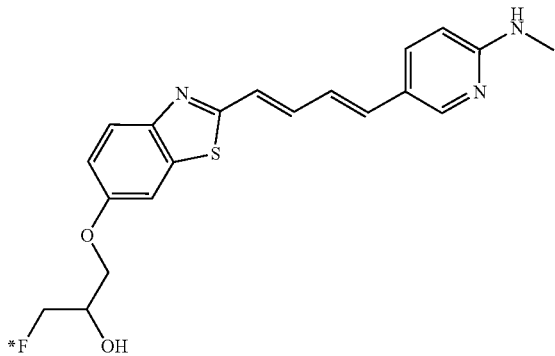 [SMILES: CNc1ccc(/C=C/C=C/c2nc3ccc(OCC(O)CF)cc3s2)cn1] |
| F0-PBB3.2 | 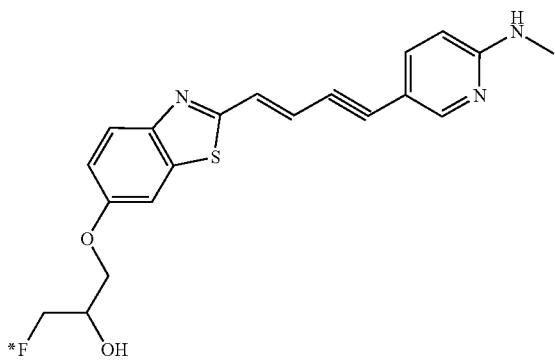 [SMILES: CNc1ccc(C#C/C=C/c2nc3ccc(OCC(O)CF)cc3s2)cn1] |
| F1-PBB3 | 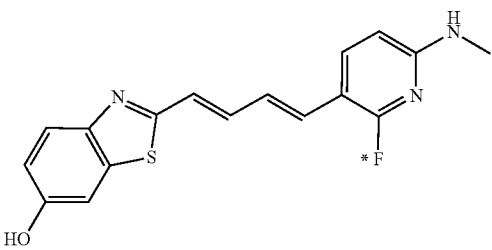 [SMILES: CNc1ccc(/C=C/C=C/c2nc3ccc(O)cc3s2)c(F)n1] |
| F1-PBB3.2 | 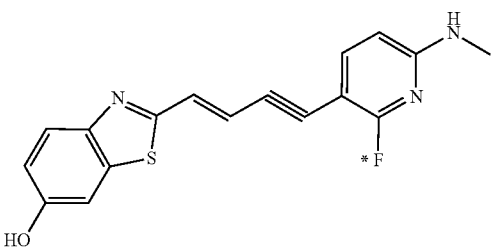 [SMILES: CNc1ccc(C#C/C=C/c2nc3ccc(O)cc3s2)c(F)n1] |
| F1-PBBf3 | 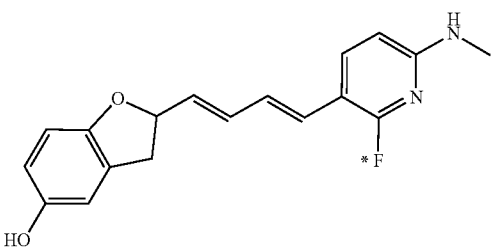 [SMILES: CNc1ccc(/C=C/C=C/C2Cc3cc(O)ccc3O2)c(F)n1] |

-continued

| Name | Structural Formula |
|---|---|
| F1-PBBf3.2 | |
| PBQ3.0 | |
| PBQ3 | |
| PBQ3.1 | |
| PBQ3.2 | | or a radioisotopically labeled analog thereof, wherein an atom with a "*" symbol is the radioisotope of the atom, and wherein if there are two "*" symbols in the compound, then one or both are radioisotopes of the atom.

22. The method of claim 21, wherein, in the compound, one or more atoms are a radioisotope of the atom or atoms.

23. The method of claim 21, wherein, in the compound, a carbon atom on nitrogen bound to a benzene ring or a pyridine ring is the radioisotope $^{11}C$.

24. The method of claim 21, wherein, in the compound, F in the compound is the radioisotope $^{18}F$.

25. The method of claim 21, wherein, in the compound, a carbon atom of a methoxy group bound to a benzothiazole ring is the radioisotope $^{11}C$.

26. The method of claim 21, wherein the compound is the radioisotopically labeled analog thereof.

* * * * *